United States Patent

Yang et al.

[11] Patent Number: 6,025,372
[45] Date of Patent: Feb. 15, 2000

[54] SOMATOSTATIN AGONISTS

[75] Inventors: Lihu Yang, Edison; Arthur A. Patchett, Westfield; Alexander Pasternak, Princeton; Kevin Chapman, Scotch Plains; James R. Tata, Westfield; Liangqin Guo, Edison, all of N.J.

[73] Assignee: Merck & Co., Inc., Rahway, N.J.

[21] Appl. No.: 09/053,373

[22] Filed: Apr. 1, 1998

Related U.S. Application Data

[60] Provisional application No. 60/042,920, Apr. 4, 1997, and provisional application No. 60/064,380, Nov. 6, 1997.

[51] Int. Cl.⁷ ........................ A61K 31/445; C07D 40/10; C07D 401/12
[52] U.S. Cl. ........................ 514/316; 514/235.5; 514/255; 514/318; 514/322; 544/129; 544/364; 546/187; 546/194; 546/199
[58] Field of Search ...................................... 546/187, 194, 546/199; 544/364, 129; 514/255, 316, 318, 322, 235.5

[56] References Cited

U.S. PATENT DOCUMENTS 5,710,155  1/1998  Schnorrenberg et al. .............. 514/255
5,869,489  2/1999  Shah et al. ............................ 514/253

FOREIGN PATENT DOCUMENTS

WO 98/11128  3/1998  WIPO .

OTHER PUBLICATIONS

Rudolf, K., et al., Chemical Abstracts, vol. 128, p. 604, 1998.
Bhattacharjee "A quantum chemical study of some model anti–inflammatory compounds" CA 117:39826, 1990.

*Primary Examiner*—Ceila Chang
*Attorney, Agent, or Firm*—James L. McGinnis; David L. Rose; Richard C. Billups

[57] ABSTRACT

Somatostatin agonist compounds of formula I are disclosed:

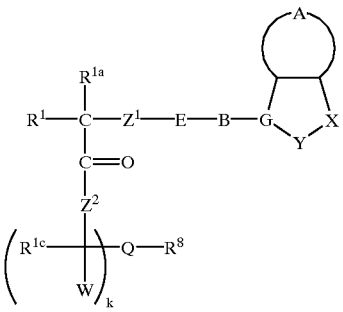

including pharmaceutically acceptable salts and hydrates thereof These compounds are useful in the treatment of diabetes, cancer, acromegaly, restenosis, depression, irritable bowel syndrome and pain. The compounds are potent with high selectivity toward the receptor subtype 2.

Pharmaceutical compositions and methods of treatment are also included.

19 Claims, No Drawings

SOMATOSTATIN AGONISTS

This application claims benefit of Provisional Applns. 60/042,920 filed Apr. 14, 1997 and 60/064,380 filed Nov. 6, 1997.

BACKGROUND OF THE INVENTION

Somatostatin (SST) is a widely distributed peptide occurring in two forms SST-14 (with 14 amino acids) and SST-28 (with 28 amino acids). SST has multiple functions including modulation of secretion of growth hormone, insulin, glucagon, pancreatic enzymes and gastric acid, in addition to having potent anti-proliferative effects.

The mechanism of action of somatostatin is mediated via high affinity membrane associated receptors. Five somatostatin receptors (SSTR1–5) are known (Reisine, T.; Bell, G.I. *Endocrine Reviews* 1995, 16, 427–442). All five receptors are heterogeneously distributed and pharmacologically distinct. Structure-function studies with a large number of peptidal analogs have shown that the Trp-Lys dipeptide of somatostatin is important for high-affinity binding. The availability of these receptors now makes it possible to design selectively active ligands for the subtypes to determine their physiological functions and to guide potential clinical applications. For example, studies utilizing subtype selective peptides have provided evidence that somatostatin subtype 2 receptors (SSTR2) mediates the inhibition of growth hormone release from the anterior pituitary and glucagon release from the pancreas, whereas SSTR5 selective agonists inhibit insulin release. These results imply the usefulness of SSTR2 selective analogs in the treatment of diabetes and many of the compounds of this invention have that selectivity.

In addition, the novel compounds described herein are useful in the therapy of a variety of conditions which include acromegaly, retinal neovascularization, neuropathic and visceral pain, irritable bowel syndrome, chronic atrophic gastritis, Crohn's disease, rheumatoid arthritis and sarcoidosis. The instant compounds inhibit cell proliferation and cause the regression of certain tumors including breast and pancreatic cancer. They are useful in preventing restenosis after angioplasty, they prevent non-steroid antiinflammatory drug (NSAID) induced ulcers, they are useful in treating colitis and to inhibit cystoid macular edema. Their central activities include promotion of REM sleep and an increase in cognitive function. They also have analgesic activities and can be used, for example, to treat cancer pain, cluster headache and post operative pain and they are useful in the prevention and treatment of migraine attacks and depression. The compounds described herein may be used in combination with other therapies, for example, with rapamycin to treat cancers, restenosis and atherosclerosis and with angiotensin converting enzyme inhibitors and insulin in the treatment of diabetes. The compounds of this invention are also remarkably reduced in size in comparison with the natural hormone and its peptide analogs such as octreotide and seglitide, which allows ease of formulation. Many of the instant compounds show activity following oral administration.

This invention relates to compounds which are agonists of somatostatin and selective toward somatostatin receptor subtype SSTR2. The compounds have a number of clinical uses including in the treatment and prevention of diabetes, cancer, acromegaly, depression, chronic atrophic gastritis, Crohn's disease, ulcerative colitis, retinopathy, arthritis, pain both viseral and neuropathic and to prevent restenosis.

SUMMARY OF THE INVENTION

The present invention relates to compounds represented by formula I:

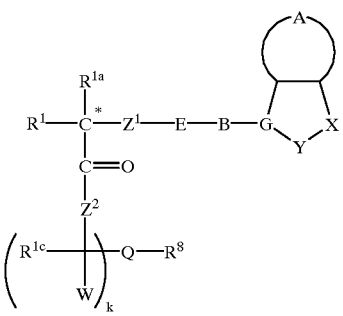

as well as pharmaceutically acceptable salts and hydrates thereof, wherein:

$R^1$ is selected from the group consisting of: $C_{1-10}$alkyl, aryl, aryl($C_{1-6}$alkyl)—, $C_{3-7}$cycloalkyl($C_{1-6}$alkyl)—, $C_{1-5}$alkyl-K-($C_1$–$C_5$ alkyl)—, aryl($C_{0-5}$ alkyl)-K-($C_{1-5}$alkyl)—, and $C_{3-7}$cycloalkyl($C_{0-5}$alkyl)-K-($C_{1-5}$alkyl)—, wherein K is —O—, —S(O)$_m$—, —N($R^2$)C(O)—, —C(O)N($R^2$)—, —$CR^2$=$CR^2$— or —C≡C—, the alkyl portions of which being optionally substituted with by 1 to 5 halogen groups, $S(O)_m R^{2a}$, 1 to 3 of $OR^{2a}$ groups or $C(O)OR^{2a}$, and wherein aryl is selected from the group consisting of: phenyl, naphthyl, biphenyl, quinolinyl, isoquinolinyl, indolyl, azaindolyl, pyridyl, benzothienyl, benzofuranyl, thiazolyl and benzimidazolyl, said aryl groups being unsubstituted or substituted with 1 to 3 $C_{1-6}$ alkyl or halo groups, 1 to 2 —$OR^2$ groups, methylenedioxy, —$S(O)_m R^2$, 1 to 2 —$CF_3$ groups, —$OCF_3$, —$NO_2$, —$N(R^2)C(O)(R^2)$, —$C(O)OR^2$, —$C(O)N(R^2)_2$, 1H-tetrazol-5-yl, —$SO_2N(R^2)(R^2)$, —$N(R^2)SO_2$ phenyl, or —$N(R^2)SO_2R^2$;

$R^2$ is selected from the group consisting of: H, $C_{1-8}$alkyl, —$(CH_2)_t$-aryl and $C_{3-7}$cycloalkyl, and where two $R^2$ groups are present, they optionally are joined to form a $C_3$–$C_8$ ring, optionally interrupted by O, S or $NR^{3a}$, in which $R^{3a}$ is H or $C_{1-6}$alky optionally substituted by OH;

t is an integer from 0 to 3;

and when $R^2$ is other than H, $R^2$ is optionally substituted with 1 to 5 halogen groups, $S(O)_m R^{2a}$, 1 to 3 of $OR^{2a}$ groups or $C(O)OR^{2a}$, $R^{2a}$ is H or $C_{1-3}$ alkyl optionally substituted by OH;

m is 0, 1 or 2;

$R^{1a}$ is H or $C_{1-3}$alkyl;

$Z^1$ is selected from the group consisting of —O—, —$CH_2$— and $NR^{2a}$;

E is selected from the group consisting of —$SO_2$—, —C(O)—, —CO(C($R^2)_2)_n$—, —C(=N—CN)—, —C(=N—$NO_2$)— and —C(=N—$SO_2N(R^2)_2$)—;

n is an integer from 0 to 3;

B is selected from the group consisting of:

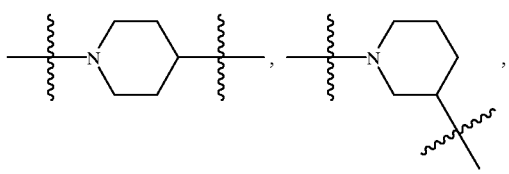

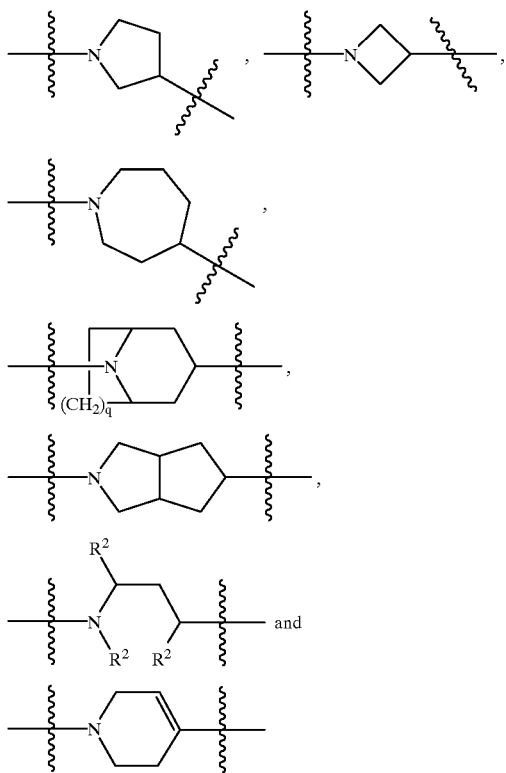

where attachment points are indicated by lines

and q is 0, 1, 2 or 3, said group being optionally substituted by $C_{1-6}$alkyl, and the $R^2$ and $(CH_2)_q$ groups are optionally substituted as described above;

represents an aromatic or non-aromatic 5–6 membered ring structure wherein:

G is N, CH or C;

Y is —C(O)—, —SO$_2$—, —C(OR$^{11}$)═, —C(SR$^{11}$)═, —C(NR$^{11}$)═, ═N—, —NR$^{11}$)—, ═NC(O)— or —C(R$^{11}$)$_2$—; and X is —N(R$^{11}$)—, ═N—, ═N—C(R$^{11}$)$_2$—, —N(R$^{11}$)C(R$^{11}$)$_2$—, —O—, —O—C(R$^{11}$)$_2$—, —S—, —S—C(R$^{11}$)$_2$— or C(R$^{11}$)$_2$;

$R^{11}$ is H, $C_{1-8}$alkyl, $CF_3$, $CH_2CF_3$, —(CH$_2$)$_p$OR$^2$, —(CH$_2$)$_p$N(R$^2$)$_2$, —(CH$_2$)$_p$N(R$^2$)C(O)N(R$^2$)$_2$, —(CH$_2$)$_p$N(R$^2$)C(O)R$^2$, —(CH$_2$)$_p$-heteroaryl, —(CH$_2$)$_p$N(R$^2$)SO$_2$C$_{1-4}$alky, —(CH$_2$)$_p$C(O)N(R$^2$)$_2$ or —(CH$_2$)$_p$C(O)OR$^2$, wherein heteroaryl is selected from tetrazolyl, oxadiazolyl, imidazolyl and triazolyl, said heteroaryl being optionally substituted with $R^2$, $OR^2$, $CF_3$ or $N(R^2)_2$ and where p is 0–3;

is a 5–10 membered fused aryl or heteroaryl group having 1–4 heteroatoms selected from O, S and N, or a 5–10 membered cycloall or heterocycloalkyl group having 1–3 heteroatoms selected from O, S and N, said aryl, heteroaryl, cycloalyl or heterocycloalkyl group being optionally substituted with 1–3 $C_{1-6}$alkyl or halo groups, —OR$^2$, N(R$^2$)$_2$, methylenedioxy, —S(O)$_m$R$^2$, —CF$_3$, —OCF$_3$, —NO$_2$, —N(R$^2$)C(O)(R$^2$), —C(O)OR$^2$, —C(O)N(R$^2$)$_2$, 1H-tetrazol-5-yl, —SO$_2$N(R$^2$)$_2$, —N(R$^2$)SO$_2$ phenyl, —N(R$^2$)C(O)N(R$^2$)$_2$ or —N(R$^2$)SO$_2$R$^2$;

$Z^2$ is selected from the group consisting of —O—, —CH$_2$—, —CHR$^{2b}$— and —NR$^{2b}$—, wherein $R^{2b}$ is selected from the group consisting of: H, $C_{1-8}$alkyl, —(CH$_2$)$_t$-aryl, —(CH$_2$)$_n$CO$_2$R$^2$, —(CH$_2$)$_n$CON(R$^2$)$_2$ and —(CH$_2$)$_n$OR$^2$, and when $Z^2$ is NR$^{2b}$ it can optionally be linked to $R^{1c}$, Q or W to form a C5–8 ring, which is optionally interrupted by O, S(O)$_m$ or NR$^{2a}$;

$R^{1c}$ is selected from the group consisting of: H, —(CH$_2$)$_q$R$^2$, —(CH$_2$)$_q$OR$^2$ and $C_{1-8}$alkyl;

W is selected from the group consisting of: H, $C_{1-8}$alkyl, (CH$_2$)$_t$-aryl, —(CH$_2$)$_q$C(O)OR$^2$, —(CH$_2$)$_q$OR$^2$, —(CH$_2$)$_q$OC(O)R$^2$, —(CH$_2$)$_q$C(O)R$^2$, —(CH$_2$)$_q$C(O)(CH$_2$)$_t$aryl, —(CH$_2$)$_q$C(O)N(R$^2$)$_2$, —(CH$_2$)$_q$N(R$^2$)C(O)R$^2$, —(CH$_2$)$_q$N(R$^2$)SO$_2$R$^2$, —(CH$_2$)$_q$N(R$^2$)C(O)N(R$^2$)$_2$, —(CH$_2$)$_q$OC(O)N(R$^2$)$_2$, —(CH$_2$)$_q$N(R$^2$)C(O)OR$^2$, —(CH$_2$)$_q$N(R$^2$)SO$_2$N(R$^2$)$_2$, —(CH$_2$)$_q$S(O)$_m$R$^2$ and —(CH$_2$)$_t$-heteroaryl, the heteroaryl portion of which is selected from: tetrazolyl, oxadiazolyl, thiadiazolyl, triazolyl and pyrazinyl, optionally substituted with $R^2$, N(R$^2$)$_2$ or OR$^2$, and when $R^2$ is other than H, said $R^2$, (CH$_2$)$_q$ and the (CH$_2$)$_t$ portions of W are optionally substituted with 1 to 2 $C_{1-4}$all4rl, OR$^{2a}$, C(O)OR$^{2a}$ or 1–3 halo groups, and the aryl and heteroaryl portions of W are optionally substituted with 1 to 3 halo groups, —OR$^2$, —CON(R$^2$)$_2$, —C(O)OR$^2$, $C_{1-4}$alkyl, —S(O)$_m$R$^2$ N(R$^2$)$_2$, $CF_3$ or 1H-tetrazol-5-yl;

k is 0 or 1, such that when k is 0, Q is attached directly to $Z^2$;

Q represents a member selected from the group consisting of:

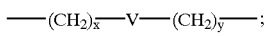

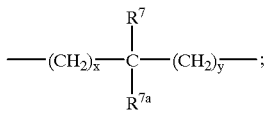

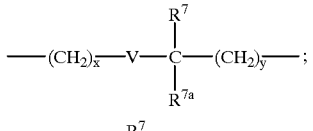

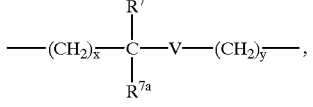

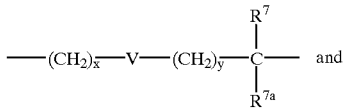

-continued

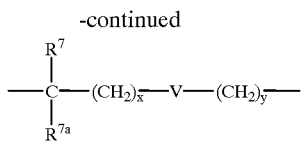

wherein x and y are independently 0, 1, 2, 3, 4, 5 or 6;

V is a $C_{3-10}$ saturated, partially saturated or aromatic mono- or bicyclic ring system, containing 1–4 N atoms and 0–2 O or S atoms, said ring system being optionally substituted with 1 to 3 halo groups, $-OR^2$, $-CON(R^2)_2$, $-C(O)OR^2$, $C_{1-4}$alkyl, $-S(O)_mR^2$, $(CH_2)_tN(R^2)_2$, $CF_3$ or 1H-tetrazol-5-yl;

$R^7$ and $R^{7a}$ are independently $CF_3$ or $R^2$;
$R^8$ is selected from the group consisting of H, $-NR^4R^5$, $-C(=NR^9)N(R^{10})_2$ and $-N^+R^4)_3$;

$R^4$ and $R^5$ are independently selected from the group consisting of: $R^2$, $-C(=NR^2)N(R^2)_2$, $-C(=NCN)N(R^2)_2$, $-C(=NC(O)R^2)N(R^2)_2$, $C(=NSO_2R^2)N(R^2)_2$, $C(=NNO_2)NR^2$, heteroaxyl, $-C(O)N(R^2)_2$, $-C(=S)N(R^2)_2$, $-C(O)R^2$, 2,2,2-trifluoroethyl, 3,3,3-trifluoropropyl and $-(CH_2)_t$-cyclopropyl, or $R^4$ and $R^5$ are taken together and represent $-(CH_2)_d-L_a(CH_2)_e-$ wherein $L_a$ is $-C(R^2)_2-$, $-O-$, $-S(O)_m-$ or $-N(R^2)-$, and d and e are independently 0 to 3 such that d plus e equals 2–6, and said heteroaryl and $R^2$ other than H being optionally substituted with 1–3 $C_{1-6}$alkyl groups, 1–7 halo groups, $N(R^2)_2$, $OR^2$, $N(R^2)C(O)R^2$, $C(O)N(R^2)$, $OC(O)R^2$, $S(O)_m^{-2}$, $CF_3$, $OCF_3$, $NO_2$, $N(R^2)C(O)(R^2)$, $N(R^2)C(O)N(R^2)_2$, $C(O)OR^2$, $C(O)N(R^2)_2$, $SO_2N(R^2)_2$, $N(R^2)SO_2R^2$ or methylenedioxy;

and $R^9$ and $R^{10}$ are independently H or $C_{1-8}$alkyl or may be taken together and represent a $C_{5-8}$ ring, optionally substituted by 1–5 halo groups, $OR^2$ or $S(O)_mR^2$.

Pharmaceutical compositions and methods of treatment are also included.

DETAIL DESCRIPTION OF THE INVENTION

One aspect of the invention that is of particular interest, relates to compounds of formula I wherein: Q is $-(CH_2)_{\overline{x}}-V-(CH_2)_{\overline{y}}-$ or

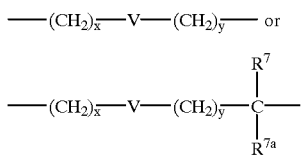

and x and y are independently 0, 1, 2 or 3. Within this subset, all other variables are as originally defined with respect to formula I.

Another aspect of the invention that is of particular interest relates to compounds of formula I wherein:

B is selected from the group consisting of a noncyclic or heterocyclic selected from the group consisting of

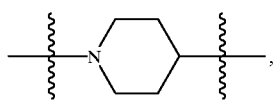

-continued

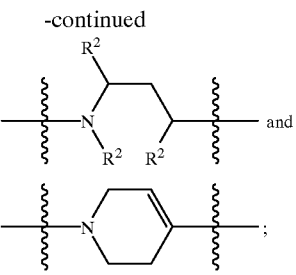

where attachment points are indicated by lines

external to the rings and to the open ring which are optionally substituted by $C_1-C_6$ alkyl and where $R^2$ and $(CH_2)_q$ are as originally described. Within this subset, all other variables are as originally defined with respect to formula I.

More particularly, another aspect of the invention that is of particular interest relates to compounds of formula I wherein:

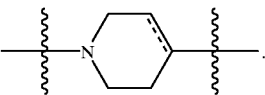

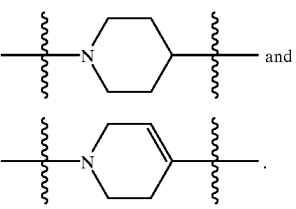

Even more particularly, another aspect of the invention that is of particular interest relates to compounds of formula I wherein B is

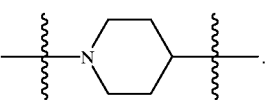

Within this subset, all other variables are as originally defined with respect to formula I.

Another aspect of the invention that is of particular interest relates to compounds of formula I wherein: V represents a member selected from the group consisting of:

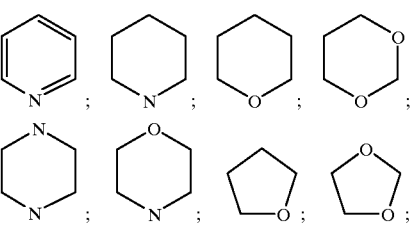

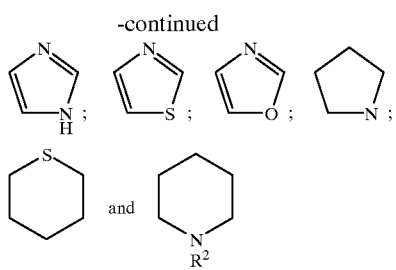

which can be optionally substituted with 1 to 3 halogen, —OR², —CON(R²)₂, —C(O)OR², $C_1$–$C_4$ alkyl, —S(O)$_m$², N(R²)₂, $CF_3$ or 1H-tetrazol-5-yl, and in the case where diastereo- or regioisomers are present, all are included. Within this subset, all other variables are as originally defined with respect to formula I.

Another aspect of the invention that is of particular interest relates to compounds of formula I wherein: $R^8$ represents H or —NR⁴R⁵. Within this subset, all other variables are as originally defined with respect to formula I.

More particularly, an aspect of the invention that is of interest relates to compounds of formula I wherein $R^8$ represents H or —NR⁴R⁵, and $R^4$ and $R^5$ are independently selected from the group consisting of R², 2,2,2-trifluoroethyl, 3,3,3-trifluoropropyl and (CH₂)$_t$-cyclopropyl wherein t=0 or 1. Within this subset, all other variables are as originally defined with respect to formula I.

Another aspect of the invention that is of interest relates to compounds of formula I wherein:

$R^1$ is selected from the group consisting of:

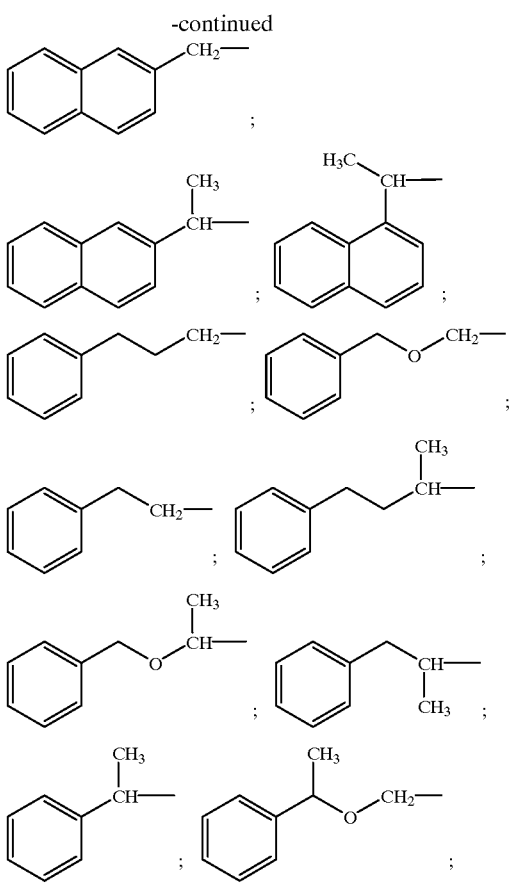

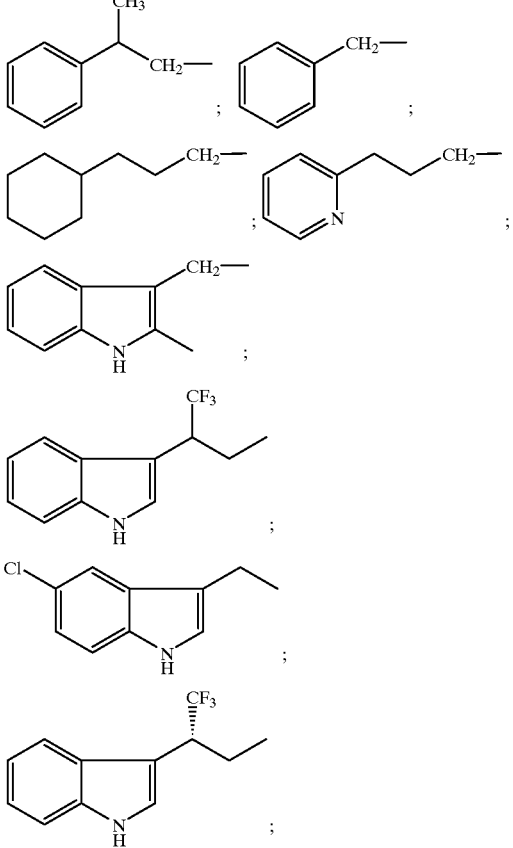

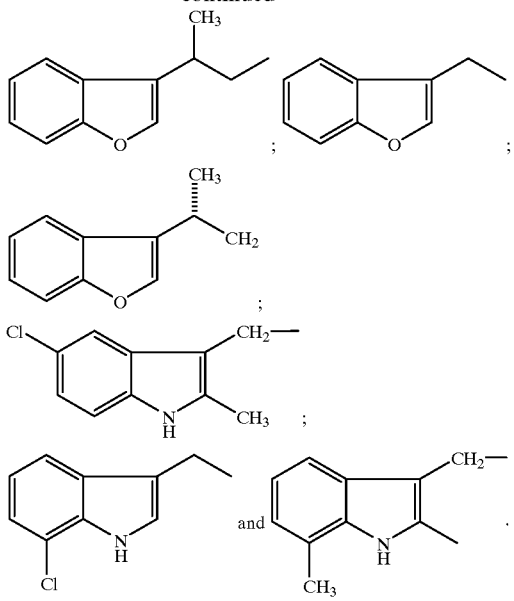

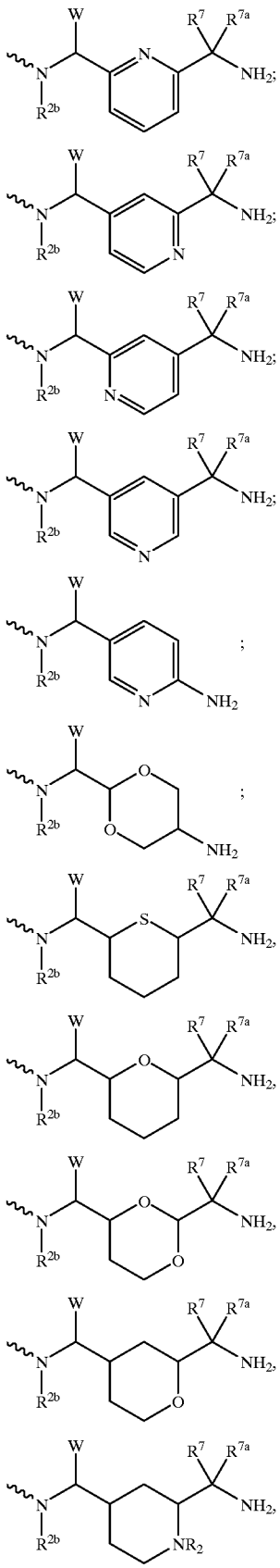

where the aryl portion is unsubstituted or substituted with: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO_2R^2$. Within this subset, all other variables are as originally defined with respect to formula I.

Another aspect of the invention that is of particular interest relates to compounds of formula I wherein:

$R^2$ is selected from: hydrogen, methyl, ethyl, propyl, isopropyl, butyl, isobutyl and t-butyl. Within this subset, all other variables are as originally defined with respect to formula I.

Another aspect of the invention that is of particular interest relates to compounds of formula I wherein:

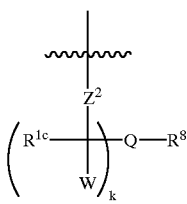

represents

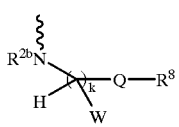

and is selected from the group consisting of:

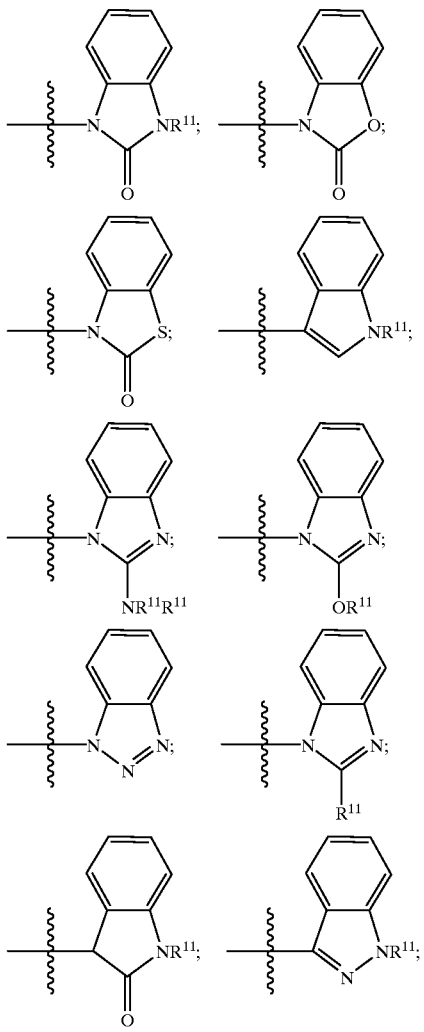

and the aromatic rings can be optionally substituted with 1 to 2 R2, 1 to 3 halogen, $-OR^2$, $-CON(R^2)_2$, $-C(O)OR^2$, $C_1-C_4$ alkyl, $-S(O)_mR^2$, $N(R^2)_2$, $CF_3$; and in the case where diastereo- or regioisomers are present, all are included; and x is an integer from 0 to 3. Within this subset, all other variables are as originally defined with respect to formula I.

Another aspect of the invention that is of particular interest relates to compounds of formula I wherein:

W is selected from the group consisting of: hydrogen, $C_1-C_4$ allyl, $(CH_2)_qC(O)OR^2$. Within this subset, all other variables are as originally defined with respect to formula I.

Another aspect of the invention that is of particular interest relates to compounds of formula I wherein:

E is selected from the group consisting of —CO—, —C(=N—CN)—, and —SO$_2$—. Within this subset, all other variables are as originally defined with respect to formula I.

Another aspect of the invention that is of particular interest relates to compounds of formula I wherein:

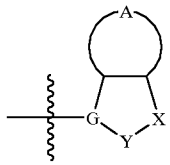

is selected from the group consisting of:

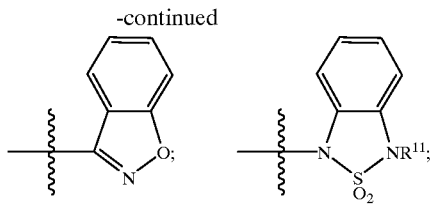

where the aromatic rings are optionally substituted with 1–3 groups of $C_1$–$C_6$ alkyl, halogen, —$OR^2_3$ $N(R^2)_2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, —1H-tetrazol-5-yl, —$SO_2N(R_2)_2$, —$N(R^2)SO_2$ phenyl, $N(R^2)C(O)N(R^2)$ or —$N(R^2)SO_2R^2$. Within this subset, all other variables are as originally defined with respect to formula I.

In one aspect of the invention the compounds and their pharmaceutically acceptable salts and hydrates thereof are of the formula:

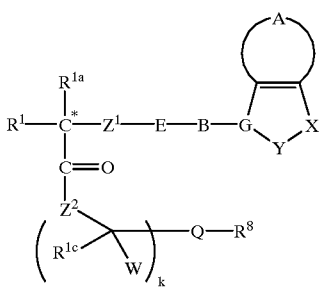

I' wherein:

$R^1$ is selected from the group consisting of: $C_1$–$C_{10}$ alkyl, aryl, aryl ($C_1$–$C_6$ alkyl), ($C_3$–$C_7$ cycloalkyl)($C_1$–$C_6$ alkyl)—, ($C_1$–$C_5$ alkyl)—K—($C_1$–$C_5$ alkyl)—, aryl($C_0$–$C_5$ alkyl)—K—($C_1$–$C_5$ alkyl)—, and ($C_3$–$C_7$ cycloalkyl)($C_0$–$C_5$ alkyl)—K—($C_1$–$C_5$ alkyl)—, where K is —O—, —$S(O)_m$—, —$N(R^2)C(O)$—, —$C(O)N(R^2)$—, —$CR^2$=$CR^2$—, or —C∫C—, where $R^2$ and alkyl may be further substituted by 1 to 5 halogen, $S(O)_mR^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofaranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO_2$ $R^2$;

$R^2$ is selected from: hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfiz or $NR^{3a}$, where $R^{3a}$ is hydrogen, or $C_1$–$C_6$ alkyl, optionally substituted by hydroxyl; Aryl is defined in the body of the case.

$R^{1a}$ is selected from the group consisting of hydrogen, and $C_1$–$C_3$ alkyl;

$R^{2a}$ is selected from the group consisting of hydrogen and $C_1$–$C_3$ alkyl, said alkyl optionally substituted by hydroxyl;

$R^{2b}$ is selected from hydrogen, $C_1$–$C_8$ alkyl, $(CH_2)_t$ aryl, —$(CH_2)_nCO_2R^2$, —$(CH_2)_nCON(R^2)_2$, —$(CH_2)_nOH$ or —$(CH_2)_nOR^2$;

$R^{1c}$ is selected from the group consisting of hydrogen, —$(CH_2)_qSR^2$, —$(CH_2)_qOR^2$ and $C_1$–$C_8$ alkyl;

$Z^1$ is selected from the group consisting of —O—, —CH2— and —$NR^{2a}$;

$Z^2$ is selected from the group consisting of —O—, —CH2—,—$CHR^{2b}$— and —$NR^{2b}$, when $Z^2$ is $NR^{2b}$ it can optionally be linked to $R^{1c}$, Q and/or W to form a C5–8 cyclic ring, which can optionally be interrupted by oxygen, $S(O)_m$ or $NR^{2a}$;

W is selected from the group consisting of: hydrogen, $C_1$–$C_8$ alkyl, (CH2), aryl, —$(CH_2)_qC(O)OR^2$, —$(CH_2)_qOR^2$, —$(CH_2)_qOC(O)R^2$, —$(CH_2)_qC(O)R^2$, —$(CH_2)_qC(O)(CH_2)_r$aryl, —$(CH_2)_qC(O)N(R^2)_2$, —$(CH_2)_qN(R^2)C(O)R^2$, —$(CH_2)_qN(R^2)SO_2R^2$, —$(CH_2)_qN(R^2)C(O)N(R^2)_2$, —$(CH_2)_qOC(O)N(R^2)_2$, —$(CH_2)_qN(R^2)C(O)OR^2$, —$(CH_2)_q N(R^2)SO_2N(R^2)_2$, —$(CH_2)_qS(O)_mR^2$, and $(CH_2)_t$ heteroaryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ are optionally substituted with 1 to 2 $C_1$–$C_4$ allyl, $OR^2$, $C(O)OR^2$, 1–3 halo and said aryl is optionally substituted with 1 to 3 halogen, —$OR^2$, —$CON(R^2)_2$, —$C(O)OR^2$, $C_1$–$C_4$ alkyl, —$S(O)_mR^2$, $N(R^2)_2$, $CF_3$ or 1H-tetrazol-5-yl;

Q is selected from the group consisting of:

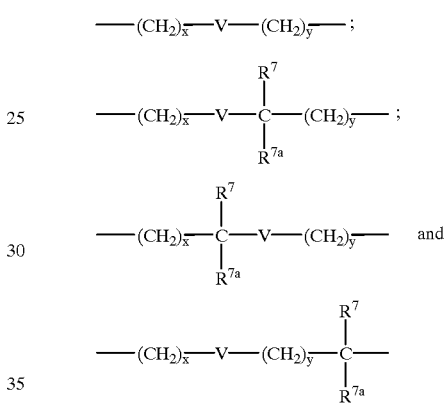

where x and y are independently 0, 1, 2, 3, 4, 5, 6;

V is a $C_{3-10}$ heterocyclic ring which may be a saturated, partially saturated or aromatic cyclic or bicyclic ring, including all regio- and diastereo- isomers, containing 1–4 of N or 1–2 of O or S and including the group consisting of furan, thiophene, imidazole, oxazole, thiazole, pyridine, pyrimidine, purine, indole, quinoline, isoquinoline, thiolane, tetrahydrofuran, tetrahydropyran, azetidine, pyrrolidine, piperidine, imidazoline, morpholine, piperazine, pyrazine, tetrahydrothiopyran, 1,3-dioxolane, 1,3-dioxane, said the heterocyclic ring can be optionally substituted with 1 to 3 halogen, —$OR^2$, —$CON(R^2)_2$, —$C(O)OR^2$, $C_1$–$C_4$ alkyl, —$S(O)_mR^2$, $(CH_2)_tN(R^2)_2$, $CF_3$ or 1H-tetrazole-5-yl; and in the case where diastereo- or regio- isomers are present, all are included;

$R^7$ and $R^{7a}$ are independently txifluoromethyl or $R^2$;

R8 is selected from the group consisting of hydrogen, $R^4$ and $R^5$ are independently selected from the group consisting of $R^2$, —$C(=NR^2)N(R^2)_2$, —$C(=NCN)N(R^2)_2$, —$C(=NC(O)R^2)N(R^2)_2$, $C(=NSO_2R^2)N(R^2)_2$, —$C(=NNO_2)NR^2$, heteroaryl, —$C(=O)N(R^2)_2$, —$C(=S)N(R^2)_2$, $C(=O)R^2$, 2,2,2-tufluoroethyl, 3,3,3-trifluoropropyl, $(CH_2)_t$ cyclopropyl, or $R^4$ and $R^5$ may be taken together to form —(CH$_2$)$_d$-L$_a$(CH$_2$)$_e$— where L$_a$ is —C(R$^2$)$_2$—, —O—, —S(O)$_m$— or —N(R$^2$)—, d and e are independently 1 to 3, said heteroaryl and R$^2$ optionally substituted with 1–3 groups of C$_{1-6}$ alkyl, 1–7 halo, N(R$^2$)$_2$, OR$^2$, N(R$^2$)C(O)R$^2$, C(O)N(R$^2$), OC(O)R$^2$, S(O)$_m$R$^2$, CF$_3$, OCF$_3$, NO$_2$, N(R$^2$)C(O)(R$^2$), N(R$^2$)C(O)N($^2$)$_2$, C(O)OR$^2$, C(O)N(R$^2$)$_2$, SO$_2$N(R$^2$)$_2$, N(R$^2$)SO$_2$R$^2$, or methylenedioxy; and the heteroaryl is pyridyl, imidazolyl, pyrimidinyl, hiazolyl or pyrazinyl;

E is selected from the group consisting of —SO$_2$—, —CO(C(R$^2$)$_2$)$_n$—, —C(=N—CN)—, —C(=N—NO$_2$)— and —C(=N—SO$_2$N(R$^2$)$_2$)—;

R$^9$ and R$^{10}$ are independently H, C$_{1-8}$ alkyl or may be taken together to form a C5–8 cyclic ring, which can optionally be substituted by 1–5 halogen, OR$^2$ or S(O)$_m$R$^2$;

B is selected from the group consisting of a noncyclic, heterocyclic or heterobicyclic ring selected from the group consisting of

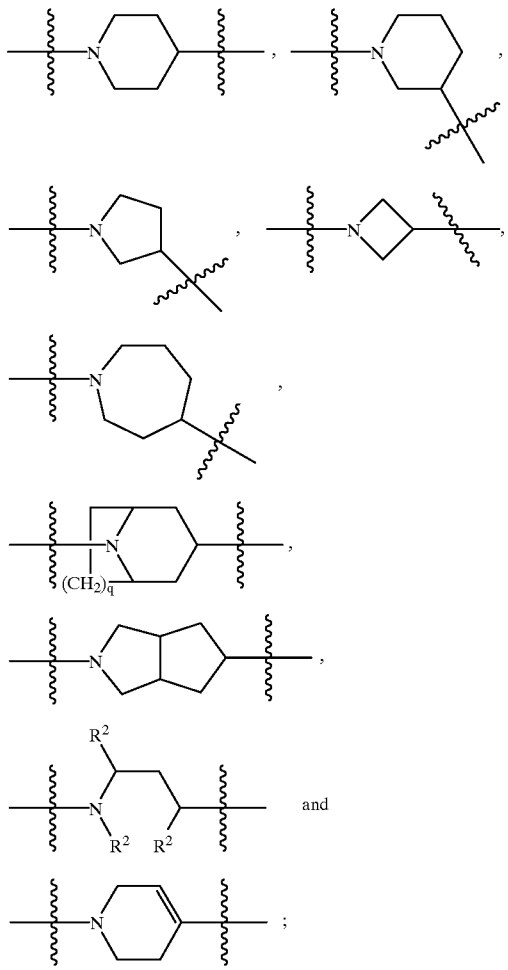

where attachment points are indicated by lines

external to the rings and to the open ring which are optionally substituted by C$_1$–C$_6$ alkyl and where R$^2$ and (CH$_2$)$_q$ are described above;

G is N, CH or C=;

Y is —C(O)—, —SO$_2$—, —C(OR$^{11}$)=, —C(SR$^{11}$)=, —C(NR$^{11}$)=, =N—, —N(R$^{11}$)—, =NC(O)—, or C(R$^{11}$)$_2$—;

X is —N(R$^{11}$)—, =N—, =N—C(R$^{11}$)$_2$—, —N(R$^{11}$)C(R$^{11}$)$_2$—, —O—, —O—C(R$^{11}$)$_2$—, —S—, —S—C(R$^{11}$)$_2$— or C(R$^{11}$)$_2$;

R$^{11}$ is H, C$_1$–C$_8$ alkyl, CF$_3$, CH$_2$CF$_3$, —(CH$_2$)$_p$OR$^2$, —(CH$_2$)$_p$N(R$^2$)$_2$, (CH$_2$)$_p$N(R$^2$)C(O)N(R$^2$)$_2$, —(CH$_2$)$_p$N(R$^2$)C(O)R$^2$, (CH$_2$)$_2$ heteroaryl, (CH$_2$)$_p$N(R$^2$)SO$_2$C$_1$–C$_4$ alkyl, —(CH$_2$)$_p$C(O)N(R$^2$)$_2$, or —(CH$_2$)$_p$C(O)OR$^2$ where heteroaryl is tetrazole, oxadiazole, imidazole or triazole which are optionally substituted with R$^2$, OR$^2$, CF$_3$ or N(R$_2$)$_2$ and where p is 0–3;

A is a fused aryl or heteroaryl group 1–4 atoms of which are heteroatoms of N, O and/or S; cycloalkyl; or heterocycloalkyl group, 1–3 atoms of which are heteroatoms N, O and/or S, said aryl, heteroaryl, cycloail or heterocycloalkyl group containing from 5 to 10 atoms and being optionally substituted with 1–3 groups of C$_1$–C$_6$ alkl, halogen, —OR$^2$, N(R$^2$)$_2$, methylenedioxy, —S(O)$_m$R$^2$, —CF$_3$, —OCF$_3$, nitro, —N(R$^2$)C(O)(R$^2$), —C(O)OR$^2$, —C(O)N(R$^2$)$_2$, —1H-tetrazol-5-yl, —SO$_2$N(R$^2$)$_2$, —N(R$^2$)SO$_2$ phenyl, N(R$_2$)C(O)N(R$_2$) or —N(R$^2$)SO$_2$R$^2$, and in the case where regioisomers are present, all are included;

k is an integer from 0 to 1, such that when k is 0, Q is attached directly to Z$^2$;

m is an integer from 0 to 2;

n is an integer from 0 to 3;

q is an integer from 0 to 3; and t is an integer from 0 to 3.

Preferred compounds of the instant invention include those of Formula Ib:

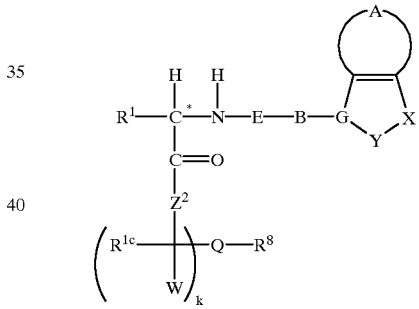

Formula Ib as well as pharmaceutically acceptable salts and hydrates thereof, wherein:

R$^1$ is selected from the group consisting of: C$_1$–C$_{10}$ alkyl, aryl, aryl (C$_1$–C$_6$ alkyl), (C$_3$–C$_7$ cycloalkyl)(C$_1$–C$_6$ alkyl)—, (C$_1$–C$_5$ alkyl)—K—(C$_1$–C$_6$ alkyl)—, aryl(C$_0$–C$_5$ alkyl)—K—(C$_1$–C$_5$ alkyl)—, and (C$_3$–C$_7$ cycloalkyl)(C$_0$–C$_5$ alkyl)—K—(C$_1$–C$_5$ alkyl)—, where K is —O—, —S(O)$_m$—, —N(R$^2$)C(O)—, —C(O)N(R$^2$)—, —CR$^2$=CR$^2$—, or —C≡C—, where R$^2$ and alkyl may be fuirther substituted by 1 to 5 halogen, S(O)$_m$R$^{2a}$, 1 to 3 of OR$^{2a}$ or C(O)OR$^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of C$_1$–C$_6$ alkyl, 1 to 3 of halogen, 1 to 2 of —OR$^2$, methylenedioxy, —S(O)$_m$R$^2$, 1 to 2 of —CF$_3$, —OCF$_3$, nitro, —N(R$^2$)C(O)(R$^2$), —C(O)OR$^2$, —C(O)N(R$^2$)(R$^2$), —1H-tetrazol-5-yl, —SO$_2$N(R$^2$)(R$^2$), —N(R$^2$)SO$_2$ phenyl, or —N(R$^2$)SO$_2$R$^2$;

R$^2$ is selected from: hydrogen, C$_1$–C$_8$ alkyl, (CH$_2$)$_t$ aryl, and C$_3$–C$_7$ cycloalkyl, and where two C$_1$–C$_6$ alkyl groups are present on one atom, they optionally are joined to form a C$_3$–C$_8$ cyclic ring, optionally including oxygen, sulfir or NR$_{3a}$, where R$_{3a}$ is hydrogen, or C$_1$–C$_6$ alkyl, optionally substituted by hydroxyl;

R$^{2a}$ is selected from the group consisting of hydrogen and C$_1$–C$_3$ alkyl, said alkyl optionally substituted by hydroxyl;

R$^{2b}$ is selected from hydrogen, C$_1$–C$_8$ alkyl, (CH$_2$)$_t$ aryl, —(CH$_2$)$_n$CO$_2$R$^2$, —(CH$_2$)$_n$CON(R$^2$)$_2$, —(CH$_2$)$_n$OH or —(CH$_2$)$_n$OR$^2$;

R$^{1c}$ is selected from the group consisting of hydrogen, and C$_1$–C$_8$ alkyl;

Z$^2$ is selected from the group consisting of —O—, —CH$_2$—, —CHR$^{2b}$— and —NR$^{2b}$, when Z$^2$ is NR$^{2b}$ it can optionally be linked to R$^{1c}$, Q and/or W to form a C$_{5-8}$ cyclic ring, which can optionally be interrupted by oxygen, S(O)$_m$ or NR$^{2a}$;

W is selected from the group consisting of: hydrogen, C$_1$–C$_8$ alkyl, (CH$_2$)$_t$ aryl, —(CH$_2$)$_q$C(O)OR$^2$, —(CH$_2$)$_q$OR$^2$, —(CH$_2$)$_q$OC(O)R$^2$, —(CH$_2$)$_q$C(O)R$^2$, —(CH$_2$)$_q$C(O)(CH$_2$)$_t$aryl, —(CH$_2$)$_q$C(O)N(R$^2$)$_2$, —(CH$_2$)$_q$N(R$^2$)C(O)R$^2$, —(CH$_2$)$_q$N(R$^2$)SO$_2$R$^2$, —(CH$_2$)$_q$N(R$^2$)C(O)N(R$^2$)$_2$, —(CH$_2$)$_q$OC(O)N(R$^2$)$_2$, —(CH$_2$)$_q$N(R$^2$)C(O)OR$^2$, —(CH$_2$)$_q$N(R$^2$)SO$_2$N(R$^2$)$_2$, —(CH$_2$)$_q$S(O)$_m$R$^2$, and (CH$_2$)$_t$heteroaryl where the heteroaryl is preferably tetrazole, oxadiazole, thiadiazole, triazole or pyrazine, which is optionally substituted with R$^2$, N(R$^2$)$_2$ and OR$^2$, where R$^2$, (CH$_2$)$_q$ and (CH$_2$)$_t$ are optionally substituted with 1 to 2 C$_1$–C$_4$ alky, OR$^2$, C(O)OR$^2$, 1–3 halo and said aryl is optionally substituted with 1 to 3 halogen, —OR$^2$, —CON(R$^2$)$_2$, —C(O)OR$^2$, C$_1$–C$_4$ alkyl, —S(O)$_m$R$^2$, N(R$^2$)$_2$, CF$_3$ or 1H-tetrazol-5-yl;

Q is

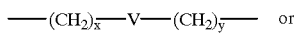

or

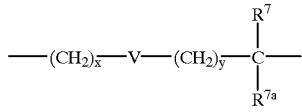

where x and y are independently 0, 1, 2, 3, 4;

V is a C$_{3-10}$ heterocyclic ring which may be a saturated, partially saturated or aromatic cyclic or bicyclic ring, including all regio- and diastereo- isomers, containing 1–4 of N or 1–2 of O or S and including the group consisting of furan, thiophene, imidazole, oxazole, thiazole, pyridine, pyrimidine, purine, indole, quinoline, isoquinoline, thiolane, tetrahydrofuran, tetrahydropyran, azetidine, pyrrolidine, piperidine, imidazoline, morpholine, piperazine, pyrazine, tetrahydrothiopyran, 1,3-dioxolane, 1,3-dioxane, said the heterocyclic ring can be optionally substituted with 1 to 3 halogen, —OR$^2$, —CON(R$^2$)$_2$, —C(O)OR$^2$, C$_1$–C$_4$ alkyl, —S(O)$_m$R$^2$, (CH$_2$)$_t$N(R$^2$)$_2$, CF$_3$ or 1H-tetrazol-5-yl; and in the case where diastereo- or regio- isomers are present, all are included;

R$^7$ and R$^{7a}$ are independently trifluoromethyl or R$^2$;

R$^8$ is selected from the group consisting of hydrogen,

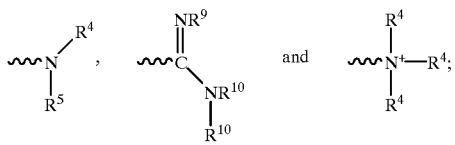

R$^4$ and R$^5$ are independently selected from the group consisting of R$^2$, —C(=NR$^2$)N(R$^2$)$_2$, —C(=NCN)N(R$^2$)$_2$, —C(=NC(O)R$^2$)N(R$^2$)$_2$, C(=NSO$_2$R$^2$)N(R$^2$)$_2$, —C(=S)N(R$^2$)$_2$, —C(NNO$_2$)NR$^2$, heteroaryl, —C(=O)N(R$^2$)$_2$, —C(=O)R$^2$, 2,2,2-trifluoroethyl, 3,3,3-trifluoropropyl, (CH$_2$)$_t$ cyclopropyl, or R$^4$ and R$^5$ may be taken together to form —(CH$_2$)$_d$-L$_a$(CH$_2$)$_e$— where L$_a$ is —C(R$^2$)$_2$—, —O—, —S(O)$_m$— or —N(R$^2$)—, d and e are independently 1 to 3, said heteroaryl and R$^2$ optionally substituted with 1–3 groups of C$_{1-6}$ alkyl, 1–7 halo, N(R$^2$)$_2$, OR$^2$, N(R$^2$)C(O)R$^2$, C(O)N(R$^2$), OC(O)R$^2$, S(O)$_m$R$^2$, CF$_3$, OCF$_3$, NO$_2$, N(R$^2$)C(O)(R$^2$), N(R$^2$)C(O)N(R$^2$), C(O)OR$^2$, C(O)N(R$^2$)$_2$, SO$_2$N(R$^2$)$_2$, N(R$^2$)SO$_2$R$^2$, or methylenedioxy; and the heteroaryl is pyridyl, imidazolyl, pyrimidinyl, thiazolyl or pyrazinyl;

E is selected from the group consisting of —SO$_2$—, —CO(C(R$^2$)$_2$)$_n$—, —C(=N—CN)—, —C(=N—NO$_2$)— and —C(=N-SO$_2$N(R$^2$)$_2$)—;

R$^9$ and R$^{10}$ are independently H, C$_{1-8}$ alkyl or may be taken together to form a C$_{5-8}$ cyclic ring, which can optionally be substituted by 1–5 halogen, OR$^2$ or S(O)$_m$R$^2$;

B is selected from the group consisting of a noncyclic or heterocyclic selected from the group consisting of

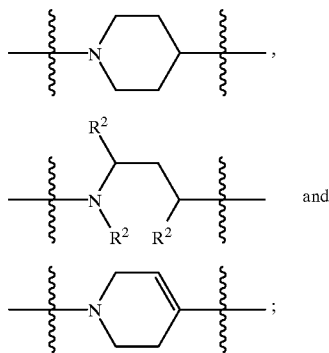

and where attachment points are indicated by lines

external to the rings and to the open ring which are optionally substituted by C$_1$–C$_6$ alkyl and where R$^2$ and (CH$_2$)$_q$ are described above;

G is N, CH or C=;

Y is —C(O)—, —SO$_2$—, —C(OR$^{11}$)=, —C(SR$^{11}$)=, —C(NR$^{11}$)=, =N—, —N(R$^{11}$)—, =NC(O)—, or —C(R$^{11}$)$_2$—;

X is —N(R$^{11}$)—, =N—, =N—C(R$^{11}$)$_2$—, —N(R$^{11}$)C(R$^{11}$)$_2$—, —O—, —O—C(R$^{11}$)$_2$—, —S—, —S—C(R$^{11}$)$_2$— or C(R$^{11}$)$_2$;

R$^{11}$ is H, C$_1$–C$_8$ alkyl, CF$_3$, CH$_2$CF$_3$, —(CH$_2$)$_p$OR$^2$, —(CH$_2$)$_p$N(R$^2$)$_2$, (CH$_2$)$_p$N(R$^2$)C(O)N(R$^2$)$_2$, —(CH$_2$)$_p$N(R$^2$)C(O)R$^2$, (CH$_2$)$_2$ heteroaryl, (CH$_2$)$_p$N(R$^2$)SO$_2$C$_1$–C$_4$ alkyl, —(CH$_2$)$_p$C(O)N(R$^2$)$_2$, or —(CH$_2$)$_p$C(O)OR$^2$ where heteroaryl is tetrazole, oxadiazole, imidazole or triazole which are optionally substituted with R$^2$, OR$^2$, CF$_3$ or N(R$^2$)$_2$ and where p is 0–3;

A is a fused aryl or heteroaryl group 1–4 atoms of which are heteroatoms of N, O and/or S; cycloalkyl; or heterocycloalkyl group, 1–3 atoms of which are heteroatoms N, O and/or S, said aryl, heteroaryl, cycloalkyl or heterocycloalkl group containing from 5 to 10 atoms and being optionally substituted with 1–3 groups of C$_1$–C$_6$ alky, halogen, —OR$^2$, N(R$^2$)$_2$, methylenedioxy, —S(O)$_m$R$^2$, —CF$_3$, —OCF$_3$, nitro, —N(R$^2$)C(O)(R$^2$), —C(O)OR$^2$, —C(O)N(R$^2$)$_2$, —1H-tetrazol-5-yl, —SO$_2$N(R$^2$)$_2$, —N(R$^2$)SO$_2$ phenyl, N(R$_2$)C(O)N(R$^2$) or —N(R$^2$)SO$_2$R$^2$, and in the case where regioisomers are present, all are included;

k is an integer from 0 to 1, such that when k is 0, Q is attached directly to $Z^2$;

m is an integer from 0 to 2;
n is an integer from 0 to 3;
q is an integer from 0 to 3, and
t is an integer from 0 to 3.

Even more preferred compounds of the instant invention include those of Formula Ic:

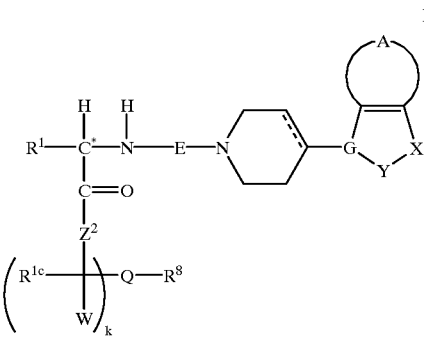

Formula Ic as well as pharmaceutically acceptable salts and hydrates thereof, wherein:

$R^1$ is selected from the group consisting of: $C_1$–$C_{10}$ alkyl, aryl, aryl ($C_1$–$C_6$ alkyl), ($C_3$–$C_7$ cycloalkyl)($C_1$–$C_6$ alkyl)—, ($C_1$–$C_5$ alkyl)—O—($C_1$–$C_5$ alkyl)—, and aryl ($C_0$–$C_5$ alkyl)—O—($C_1$–$C_5$ alkyl)—, where $R^2$ and alkyl may be further substituted by 1 to 5 halogen, $S(O)_m R^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofliranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_m R^2$, 1 to 2 of —$CF_3$, —$OCF_3$, nitro, —$N(R^2)C(O)$ ($R^2$), —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO_2R^2$;

$R^2$ is selected from: hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfuir or $NR^{3a}$, where $R^{3a}$ is hydrogen, or $C_1$–$C_6$ alkyl, optionally substituted by hydroxyl;

$R^{2a}$ is selected from the group consisting of hydrogen and $C_1$–$C_3$ alkyl, said alkyl optionally substituted by hydroxyl;

$Z^2$ is selected from the group consisting of —O—, —$CH2$—,—$CHR^{2b}$— and —$NR^{2b}$, when $Z^2$ is $NR^{2b}$ it can optionally be linked to $R^{1c}$, Q and/or W to form a C5–8 cyclic ring;

$R^{2b}$ is selected from hydrogen, C1–C8 alkyl, $(CH_2)_t$ aryl, —$(CH_2)_n CO_2 R^2$, —$(CH_2)_n CON(R^2)_2$, —$(CH_2)_n OH$ or —$(CH_2)_n OR^2$;

$R^{1c}$ is selected from the group consisting of hydrogen and $C_1$–$C_8$ alkyl;

W is selected from the group consisting of: hydrogen, $C_1$–$C_8$ alkyl, $(CH2)_t$ aryl, —$(CH_2)_q C(O)OR^2$, —$(CH_2)_q OR^2$, —$(CH_2)_q OC(O)R^2$, —$(CH_2)_q C(O)R^2$, —$(CH_2)_q C(O)$ $(CH_2)_t$ aryl, —$(CH_2)_q C(O)N(R^2)_2$, —$(CH_2)_q N(R^2)C(O)R^2$, —$(CH_2)_q N(R^2)SO_2 R^2$, —$(CH_2)_q N(R^2)C(O)N(R^2)_2$, —$(CH_2)_q OC(O)N(R^2)_2$, —$(CH_2)_q N(R^2)C(O)OR^2$, —$(CH_2)_q N(R^2)SO_2N(R^2)_2$, —$(CH_2)_q S(O)_m R^2$, and $(CH_2)_t$ heteroaryl where the heteroauyl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ are ptionally substituted with 1 to 2 $C_1$–$C_4$ alkyl, $OR^2$, $C(O)OR^2$, 1–3 halo and said aryl is optionally substituted with 1 to 3 halogen, —$OR^2$, $CON(R^2)_2$, —$C(O)OR^2$, $C_1$–$C_4$ alkyl, —$S(O)_m R^2$, $N(R^2)_2$, $CF_3$ or 1H-tetrazol-5-yl;

Q is

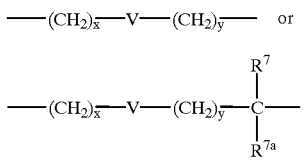

or where x and y are independently 0, 1, 2, 3; V is

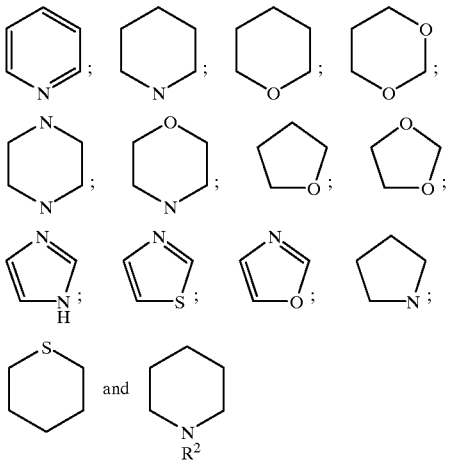

said the heterocyclic ring can be optionally substituted with 1 to 3 halogen, —$OR^2$, —$CON(R^2)_2$, —$C(O)OR^2$, $C_1$–$C_4$ alkyl, —$S(O)_m R^2$, $N(R^2)_2$, $CF_3$ or 1H-tetrazol-5-yl, and in the case where diastereo- or regio- isomers are present, all are included;

$R^7$ and $R^{7a}$ are independently trifluoromethyl or $R^2$;

$R^8$ is selected from the group consistng of:

—$NR^4R^5$, —$C(=NR^9)N(R^{10})_2$ and —$N^+(R^4)_3$;

$R^4$ and $R^5$ are independently selected from the group consisting of: $R^2$, —$C(=NR^2)N(R^2)_2$, —$C(=NCN)N(R^2)_2$, —$C(=NC(O)R^2)N(R^2)_2$, $C(=NSO_2R^2)N(R^2)_2$, —$C(=NNO_2)NR^2$, heteroaryl, 2,2,2-trifluoroethyl and 3,3,3-trifluoropropyl or $R^4$ and $R^5$ are taken together and represent

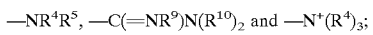

wherein $L_a$ is —$C(R_2)_2$—, —O—, —$S(O)_m$— or —$N(R^2)$—, and d and e are independently 1 to 3, and the heteroaryl is pyridyl or imidazolyl;

E is selected from the group consisting of —$SO_2$—, —CO—, —$C(=N$—CN)—, —$C(=N$—$NO_2)$— and —$C(=N$—$SO_2NH_2)$—;

$R^9$ and $R^{10}$ are independently H or $C_{1-8}$ alkyl;

G is N, CH or C=;

Y is —C(O)—, —$SO_2$—, —$C(OR^{11})=$, —$C(SR^{11})=$, —$C(NR^{11})=$, =N—, —$N(R^{11})$—, =NC(O)—, or —$C(R^{11})_2$—;

X is —$N(R^{11})$—, =N—, =N—$C(R^{11})_2$—, —$N(R^{11})C$ $(R^{11})_2$—, —O—, —O—$C(R^{11})_2$—, —S—, —S—$C(R^{11})_2$— or $C(R^{11})_2$;

$R^{11}$ is H, $C_1$–$C_8$ alkyl, $CF_3$, $CH_2CF_3$, —$(CH_2)_p OR^2$, —$(CH_2)_p N(R^2)_2$, $(CH2)_p N(R^2)C(O)N(R^2)_2$, —$(CH_2)_p N$ $(R^2)C(O)R^2$, $(CH_2)_p$ heteroaryl, $(CH_2)_p N(R^2)SO_2 C_1$–$C_4$ alkyl, —$(CH_2)_p C(O)N(R^2)_2$, or —$(CH_2)_p C(O)OR^2$ where heteroaryl is tetrazole, oxadiazole, imidazole or triazole which are optionally substituted with $R^2$, $OR^2$, $CF_3$ or $N(R^2)_2$ and where p is 0–3;

A is a fused aryl or heteroaryl group 1–4 atoms of which are heteroatoms of N, O and/or S; cycloalkyl; or heterocycloalkyl group, 1–3 atoms of which are heteroatoms N, O and/or S, said aryl, heteroaryl, cycloalkyl or heterocycloalkyl group containing from 5 to 10 atoms and being optionally substituted with 1–3 groups of $C_1$–$C_6$ alkyl, halogen, —$OR^2$, $N(R^2)_2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, —1H-tetrazol-5-yl, —$SO_2N(R^2)_2$, —$N(R^2)SO_2$ phenyl, $N(R^2)C(O)N(R^2)$ or —$N(R^2)SO_2R^2$, and in the case where regioisomers are present, all are included;

k is an integer from 0 to 1, such that when k is 0, Q is attached directly to $Z^2$;

m is an integer from 0 to 2;

n is an integer from 0 to 3;

q is an integer from 0 to 3; and t is an integer from 0 to 3.

More preferred compounds of the instant invention include those of Formula Id:

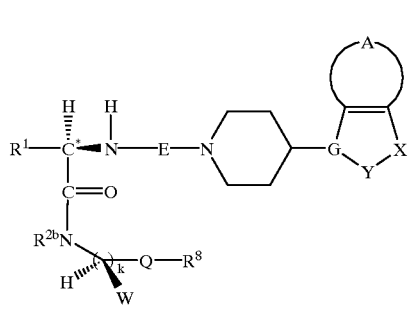

Formula Id as well as pharmaceutically acceptable salts and hydrates thereof, wherein $R^1$ is selected from the group consisting of:

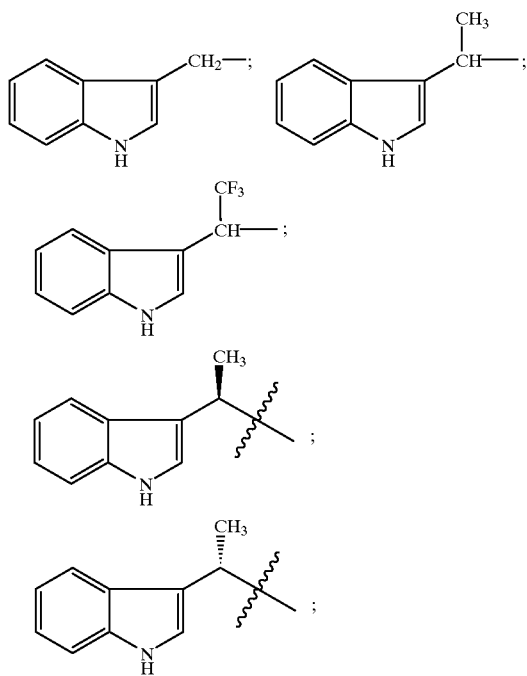

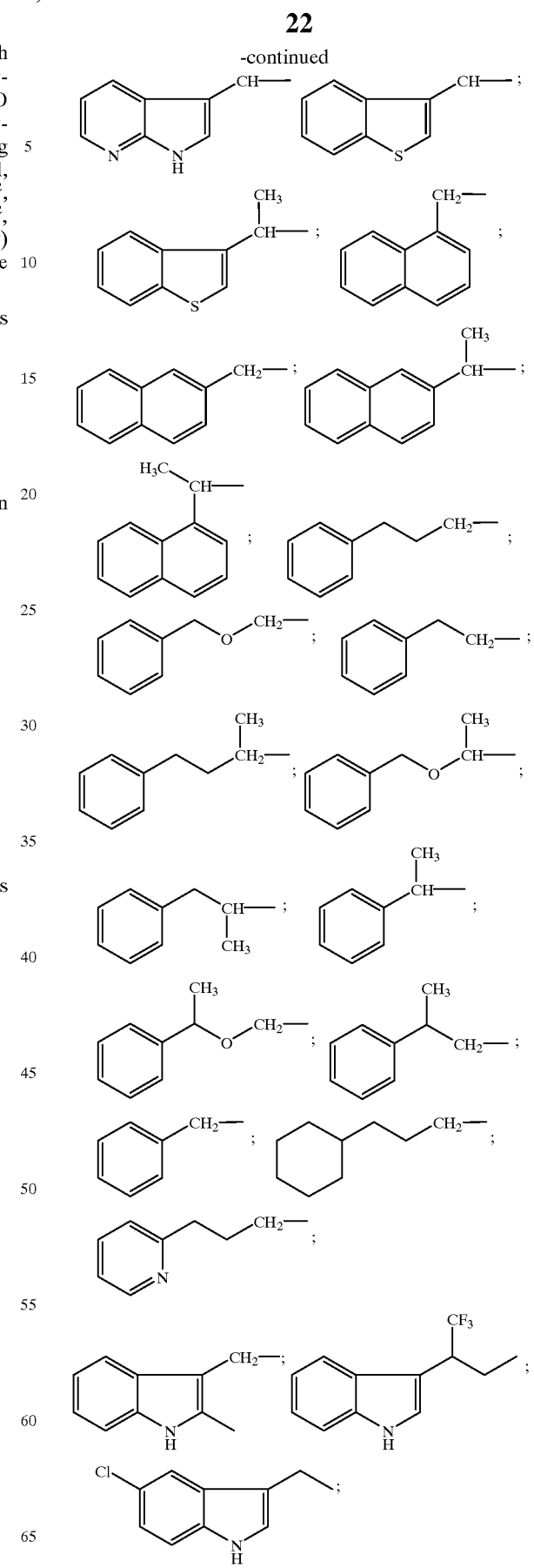

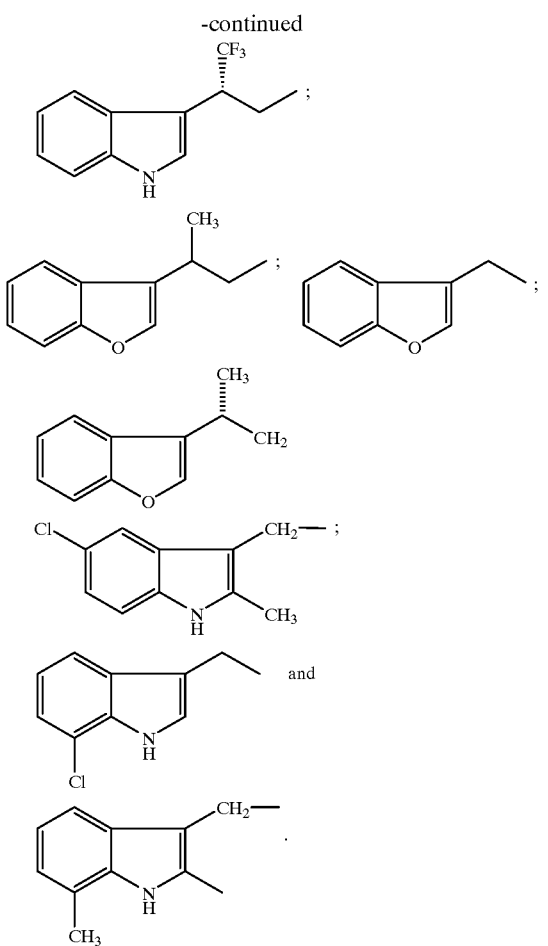
where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO_2R^2$;
$R^2$ is selected from: hydrogen, methyl, ethyl, propyl, isopropyl, butyl, isobutyl and t-butyl;
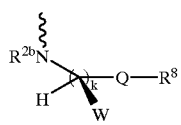
is:
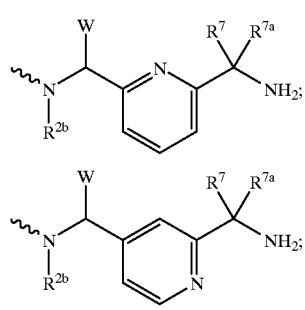
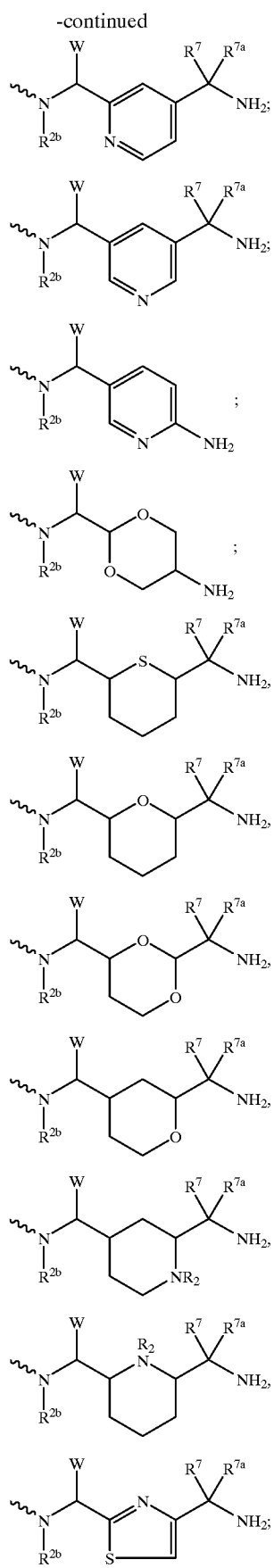

-continued

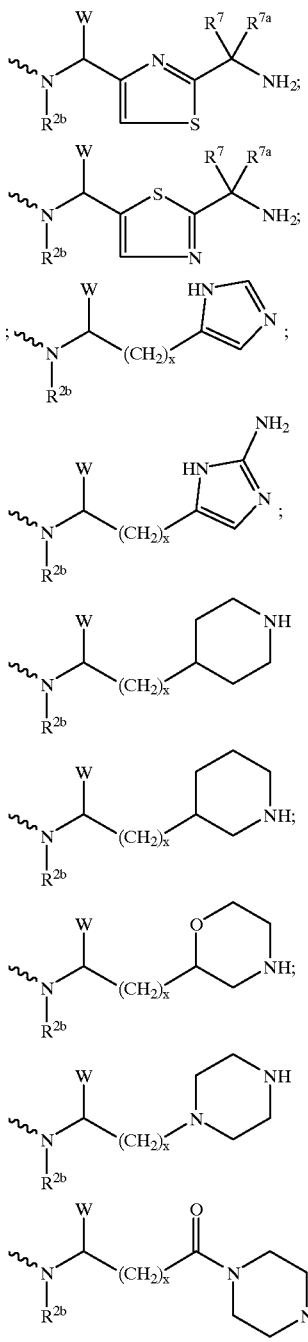

and the heterocyclic rings can be optionally substituted with 1 to 2 R2, 1 to 3 halogen, —OR², —CON(R²)₂, —C(O)OR², $C_1-C_4$ alkyl, —S(O)$_m$R², N(R²)₂, CF₃; and in the case where diastereo- or regio- isomers are present, all are included; and x is an integer from 0 to 3;

W is selected from the group consisting of: hydrogen, $C_1-C_4$ alkyl, $(CH_2)_qC(O)OR^2$;

$R^7$ and $R^{7a}$ are independently trifluoromethyl or R²;

$R^{2b}$ is selected from hydrogen and $C_1-C_4$ alkyl;

E is selected from the group consisting of —CO—, —C(=N—CN)—, and —SO₂—;

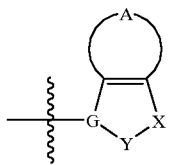

is:

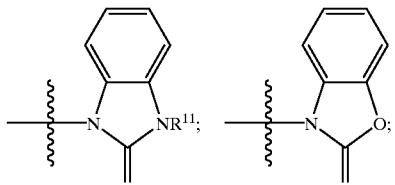

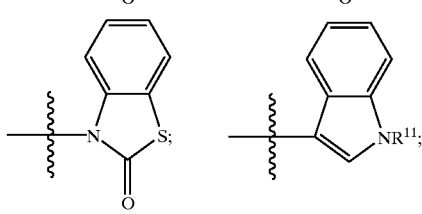

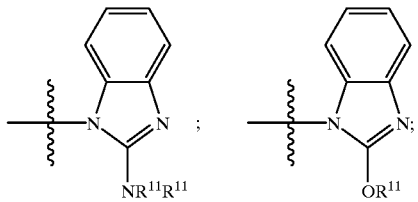

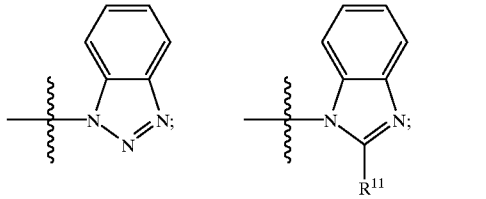

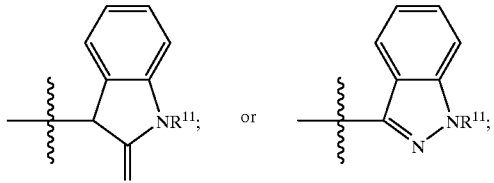

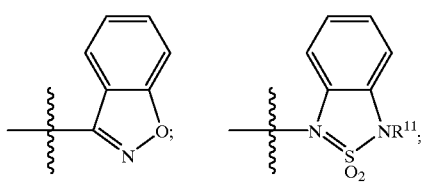

where the aromatic moiety can be optionally substituted with 1–3 groups of $C_1-C_6$ alkyl, halogen, —OR², N(R²)₂, methylenedioxy, —S(O)$_m$R², —CF₃, —OCF₃, nitro, —N(R²)C(O)(R²), —C(O)OR², —C(O)N(R²)₂, —1H-tetrazol-5-yl, —SO₂N(R²)₂, —N(R²)SO₂ phenyl, N(R²)C(O)N(R²) or —N(R²)SO₂R²;

$R^{11}$ is H, $C_1-C_8$ alkyl, CF₃, CH₂CF₃, —(CH₂)$_p$OR², —(CH₂)$_p$N(R²)₂, (CH2)$_p$N(R²)C(O)N(R²)₂, —(CH₂)$_p$N (R²)C(O)R², (CH₂)$_p$ heteroaryl, (CH₂)$_p$N(R²)SO₂C₁-C₄ alkyl, —(CH₂)$_p$C(O)N(R²)₂, or —(CH₂)$_p$C(O)OR² where heteroaryl is tetrazole, oxadiazole, imidazole or triazole which are optionally substituted with $R^2$, $OR^2$, CF3 or $N(R^2)_2$ and where p is 0–3;

k is an integer 0 or 1, such that when k is 0, Q is directly attached to $NR^{2b}$;

m is an integer from 0 to 2;

n is an integer from 0 to 3, and q is an integer from 0 to 3.

Also included in the invention is a pharmaceutical composition which is comprised of a compound of formula I in combination with a pharmaceutically acceptable carrier.

The invention also includes a method of treating diabetes, cancer, acromegaly chronic atrophic gastritis, Crohn's disease, ulcerative colitis, retinopathy, arthritis, viseral and neuropathic pain and to prevent restenosis, which comprises administering to a person or animal a compound of formula I in an amount which is effective for treating said disease or condition.

The invention is described herein in detail using the terms defined below unless otherwise specified.

The term "alkyl" refers to a monovalent alkane (hydrocarbon) derived radical containing from 1 to 15 carbon atoms unless otherwise defined and if two carbon atoms or more they may include a double or a triple bond. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

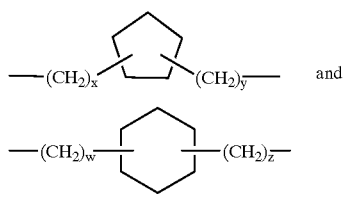

wherein: x plus y=from 0–10 and w plus z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to allyl, the straight, branched or cyclic portion of the alynyl group may contain triple bonds and may be substituted when a substituted alkynyl group is provided.

The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

Aryl refers to aromatic rings e.g., phenyl, substituted phenyl and like groups as well as rings which are fuised, e.g., naphthyl, indaryl, biphenyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted with from 1 to 3 groups of $C_1$–$C_{15}$ alkyl, halogen, —$OR^2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, —1H-tetrazol-5-yl, —$SO_2N(R^2)_2$, —$N(R^2)SO_2$ phenyl or —$N(R^2)SO_2R^2$. Preferred substituted aryls include phenyl and naphthyl substituted with one or two groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups selected from 1 to 3 of $C_1$–$C_8$ alkyl, halogen, —$OR^2$, methylenedioxy, —$S(O)_mR^2$, —$CF_3$, —$OCF_3$, $N(R^2)_2$, nitro, —$N(R^2)C(O)(R^2)$, —$C(O)OR^2$, —$C(O)N(R^2)_2$, —1H-tetrazol-5-yl, —$SO_2N(R_2)_2$, —$N(R^2)SO_2$ phenyl or —$N(R^2)SO_2R^2$.

Heteroaryl thus includes aromatic and partially aromatic groups which contain one or more heteroatoms. Examples of this type are thiophene, oxadiazole, imidazopyridine, pyridine, oxazole, thiazole, pyrazole, tetrazole, imidazole, pyrimidine, pyrazine, benzothienyl, benzofuranyl, indolyl, azaindole, benzimidazolyl, quinolinyl, isoquinolinyl and triazine.

The terms "heterocycloalkyl" and "heterocyclyl" refer to a cycloalkyl group (nonaromatic) in which one of the carbon atoms in the ring is replaced by a heteroatom selected from O, S, SO, $SO_2$ or N, and in which up to three additional carbon atoms may be optionally replaced by heteroatoms.

Heterocyclyl is carbon or nitrogen linked; if carbon linked and contains a nitrogen, then the nitrogen may be substituted by $R^{20}$. Examples of heterocyclyls are piperidinyl, morpholinyl, pyrrolidinyl, tetrahydrofuranyl, tetrahydroimidazo[4,5-c]pyridinyl, imidazolinyl, piperazinyl, pyrolidin-2-onyl, piperidin-2-onyl and the like Certain of the above defined terms may occur more than once in the above formula and upon such occurrence each term shall be defined independently of the other.

Salts encompassed within the term "pharmaceutically acceptable salts" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Camsylate, Carbonate, Citrate, Dihydrochloride, Edetate, Edisylate, Estolate, Esylate, Fumarate, Gluconate, Glutamate, Hydrobromide, Hydrochloride, Hydroxynaphthoate, Lactate, Lactobionate, Laurate, Malate, Maleate, Mandelate, Mesylate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Tosylate, and Valerate.

The compounds of the present invention may contain one or more asymmetric carbon atoms and may exist in racemic and optically active forms. All of these compounds are contemplated to be within the scope of the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention. In the case of the asymmetric carbon atom represented by an asterisk in Formula I, it has been found that compounds are more active as somatostatin agonists and, therefore preferred, in which the nitrogen substituent is above and the $R^{1a}$ is below the plane of the structure as represented in Formula II. An equivalent representation places $R^1$ and the N-substitutent in the plane of the structure with the C=O group above. This configuration corresponds to that present in a D-amino acid. In most cases, this is also designated an R-configuration, although this will vary according to the value of $R^1$ used in making R- or S-stereochemical assignments. In addition, configurations of some of the most preferred compounds of this invention are indicated. When the carbon atom in Formula I bearing an asterisk is of a defined and usually a D- configuration, up to two times more diastereomers result with each additional stereo centers are present. These diastereomers are arbitrarily referred to as diastereomer 1 ($d_1$) and diastereomer 2 ($d_2$) and so on as so forth in this invention and, if desired, their independent syntheses or chromatographic separations may be achieved as described herein. Their absolute stereochemistry may be determined by the x-ray crystallography of crystalline products or crystalline intermediates which are derivatized, if necessary, with a reagent containing an asymmetric center of known absolute configuration.

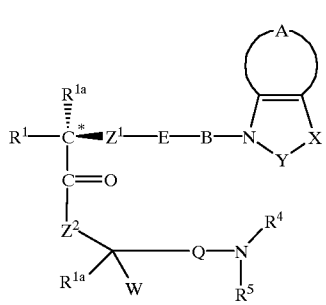

Formula II

The term "pharmacologically effective amount" shall mean hat amount of a drug or pharmaceutical agent that will elicit the iological or medical response of a tissue, system, animal or human that is being sought by a researcher or clinician.

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singlely or plurally.

The ability of the compounds of the present invention to act as somatostatin agonists makes them useful as pharmacologic agents for mammals, especially for humans, for the treatment and prevention of disorders wherein somatostatin itself or the hormones it regulates may be involved. Examples of such disorders include diabetes, acromegaly restenosis, arthritis and cancer. The instant compounds can also be used in combination with other therapeutic agents. Illustrated for diabetes, examples of these compounds include metformin or other biguanides, acarbose, sulfonylureas theazolidinediones or other insulin sensitizers including, but not limited to, compounds which function as agonists on peroxisome proliferator-activated receptor gamma (PPAR-gamma), insulin, insulin-like-growth factor I, glucagon-like peptide I-glp-I and available satiety-promoting agents such as dexfenfluramine or leptin.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Intravenous dosages or oral dosages of the compounds of the present invention, when used for the indicated effects, will range between about 0.001 to 5 mg/kg and 0.1 to 50 mg/kg, respectively. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intanasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elisirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the lke. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, steaiylamine or phosphatidylcholines.

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris/dimethylamino)-phosphonium hexafluorophosphate |
| calc. | calculated |
| CBZ, Cbz | Benzyloxycarbonyl |
| CDI | N,N'-carbonyl diimidazole |
| DCC | Dicyclohexylcarbodiimide |
| DCM | dichloromethane |
| DIEA | diisopropylethylamine |
| DMF | N,N-dimethylformamide |
| DMAP | 4-Dimethylaminopyridine |
| DSC | N,N'-disuccinimidyl carbonate |
| EDC | 1-(3-dimethylaminopropyl)-3-ethylcarbodi-imide hydrochloride |
| EI-MS | Electron ion-mass spectroscopy |
| Et | ethyl |
| EtOAc | ethyl acetate |
| EtOH | ethanol |
| eq. | equivalent(s) |
| FAB-MS | Fast atom bombardment-mass spectroscopy |
| HOAc | acetic acid |
| HOBT, HOBt | Hydroxybenztriazole |
| HPLC | High pressure liquid chromatography |
| KHMDS | Potassium bis(trimethylsilyl)amide |
| LAH | Lithium aluminum hydride |
| LHMDS | Lithium bis(trimethylsilyl)amide |
| Me | methyl |
| MeOH | methanol |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Trimethylsilane |

The instant compounds can be effective to inhibit the secretion of various hormones and trophic factors in mammals. They may be used to suppress certain endocrine secretions, such as GH, insulin, glucagon and prolactin, in the treatment of disorders such as acromegaly; endocrine tumors such as carcinoids, vipomas, insulinomas and glucagonomas; or diabetes and diabetes-related pathologies, including retinopathy, neuropathy and nephropathy. The compounds may also be used to suppress exocrine secretions in the pancreas, stomach and intestines, for treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the instant compounds include cancers of the breast, prostate, and lung (both small cell and non-small cell epidermoids), as well as hepatomas, neuroblastomas, colon and pancreatic adenocarcinomas (ductal type), chondrosarcomas, and melanomas, and also atherosclerosis associated with vascular grafts and restenosis following angioplasty.

The compounds of the instant invention are futher useful to suppress the mediators of neurogenic inflammation (e.g. substance P or the tachyiins), and may be used in the treatment of rheumatoid arthritis; psoriasis; topical inflammation such as is associated with sunburn, eczema, or other sources of itching; and allergies, including asthma. The compounds can also function as neuromodulators in the central nervous system, with useful applications in the treatment of Alzheimer's disease and other forms of dementia, pain (as a spinal analgesic), and headaches. Furthermore, in disorders involving the splanchnic blood flow, including cirrhosis and oesophagal varices, the compounds of the invention can provide cytoprotection.

The preparation of compounds of Formula I of the present invention may be carried out in sequential or convergent synthetic routes. In the interest of clarity, the special case of Formula I, where B is 4-piperidinyl and A is a fused benzo ring as being unsubstituted (formula IIA), is depicted. Compounds fused with different aromatic or non aromatic rings and/or bearing additional substituents on these rings are readily prepared by minor modification of the methods herein with procedures known in the art. Syntheses detailing the preparation of the compounds of Formula I are presented in the following reaction schemes.

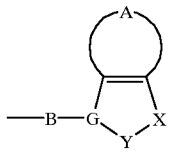

Formula IIA

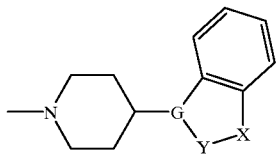

Formula IIB

The phrase "standard peptide coupling reaction conditions" is used repeatedly here, and it means coupling a carboxylic acid with an amine using an acid activating agent such as EDC, DCC, and BOP in a inert solvent such as dicbloromethane in the presence of a catalyst such as HOBT. The phrase "mixed urea formation" refers to conversion of two different amines to form their mixed urea by using phosgene or equivalents such as CDI, DSC, or p-nitrophenyl chloroformate. The reaction involves reacting one amine first with the phosgene or equivalents in the presence of a base such as NMM, TEA or DIEA in a inert solvent such as dichloromethane, THF and DMF or mixtures thereof, followed by addition of the second amine and a base such as NMM, TEA or DIEA. The uses of protective groups for amines and carboxylic acids to facilitate the desired reaction and minimize undesired reactions are well documented. Conditions required to remove protecting groups which may be present can be found in Greene, T, and Wuts, P. G. M., *Protective Groups in Organic Synthesis,* John Wiley & Sons, Inc., New York, N.Y. 1991. CBZ and BOC were used extensively and their removal conditions are known to those skilled in the art. For example, removal of CBZ groups can be achieved by a number of methods such as catalytic hydrogenation in the presence of a noble metal or its oxide such as palladium on activated carbon in a protic solvent such as ethanol. In cases where catalytic hydrogenation is contraindicated by the presence of other potentially reactive finctionality, removal of CBZ groups can also be achieved by treatment with a solution of hydrogen bromide in acetic acid, or by treatment with a mixture of TFA and dimethyl sulfide. Removal of BOC protecting groups is carried out in a solvent such as methylene chloride, methanol or ethyl acetate, with a strong acid, such as trifluoroacetic acid, hydrochloric acid or hydrogen chloride gas.

The protected amino acid derivatives required in the synthesis of compounds of Formula 1 are, in many cases, commercially available, where the protecting group (P¹) is, for example, methyl, allyl or benzyl groups. Other protected amino acid can be prepared by literature methods (Williams, R. M. *Synthesis of Optically Active α-Amino Acids,* Pergamon Press: Oxford, 1989). Many of the piperidines of Formula 2 are either commercially available or known in the literature and others can be prepared following literature methods described for analogous compounds. Some of these methods are illustrated in the subsequent schemes. Purification procedures include crystallization, normal phase or reverse phase chromatography.

The compounds of the present invention can be prepared readily according to the following Schemes or modifications thereof using readily available starting materials, reagents and conventional synthesis procedures. In these reactions, it is also possible to make use of variants which are themselves known to those of ordinary skill in this art, but are not mentioned in greater detail. The definition for $R^1$, $R^{1a}$, $R^2$, $R^4$, $R^5$, G, Y, X, $Z^1$, $Z^2$, W, Q, E, B, etc., is described above unless otherwise stated.

protected amino acid 1 and the piperidine of Formula 2, is convenienty carried out under usual urea formation reactions use phosgene or equivalents such as CDI, DSC, or p-nitrophenyi chloroformate. Removal of the P¹ protecting group can be achieved by saponifacation for most esters, or by catalytic hydrogenolysis when P¹ is benzyl, or by palladium (0) based homogeneous catalysis when P¹ is allyl. Intermediate 4A can be used as a common intermediate for the synthesis of somatostatin agonists with variation of the rest of the molecule of Formula I as shown in Scheme 2.

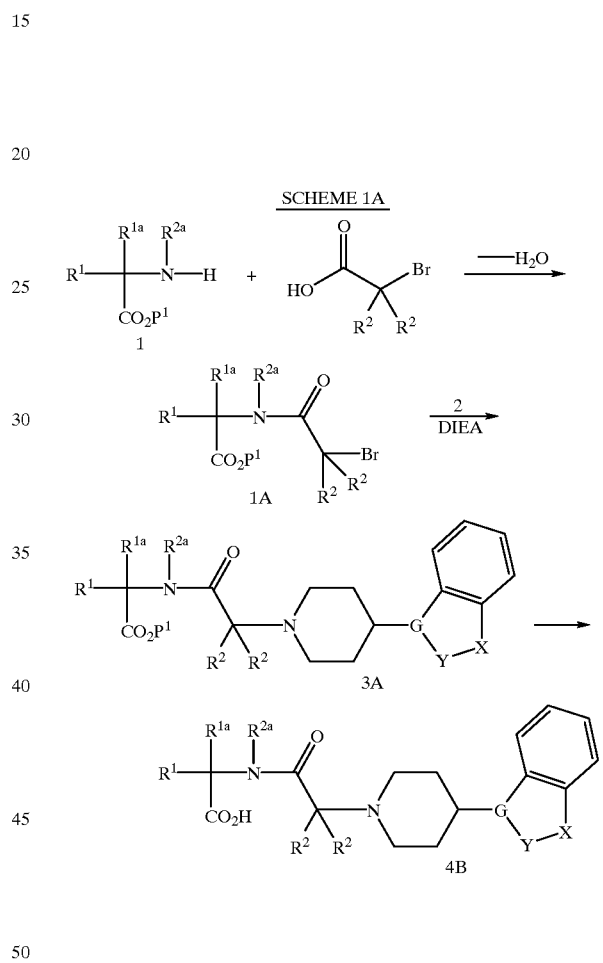

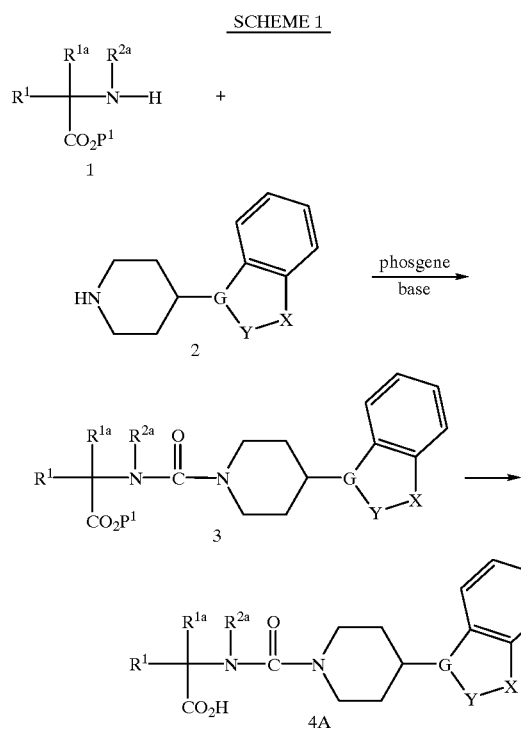

Intermediates of Formula 4A can be synthesized as described in Scheme 1. Mixed urea formation between the The preparation of amide intermediates of formula 4B can be achieved as shown in Scheme 1A. Standard peptide coupling reactions of protected amino acid 1 with 2-halo acids such as 2-bromoacetic acid gives intermediate 1A, which when reacted with aminne of formula 2 gives the compound as 3A in the presence of a non-nucleophilic base such as DIEA. The P1 protecting group can be removed as described above.

SCHEME 2

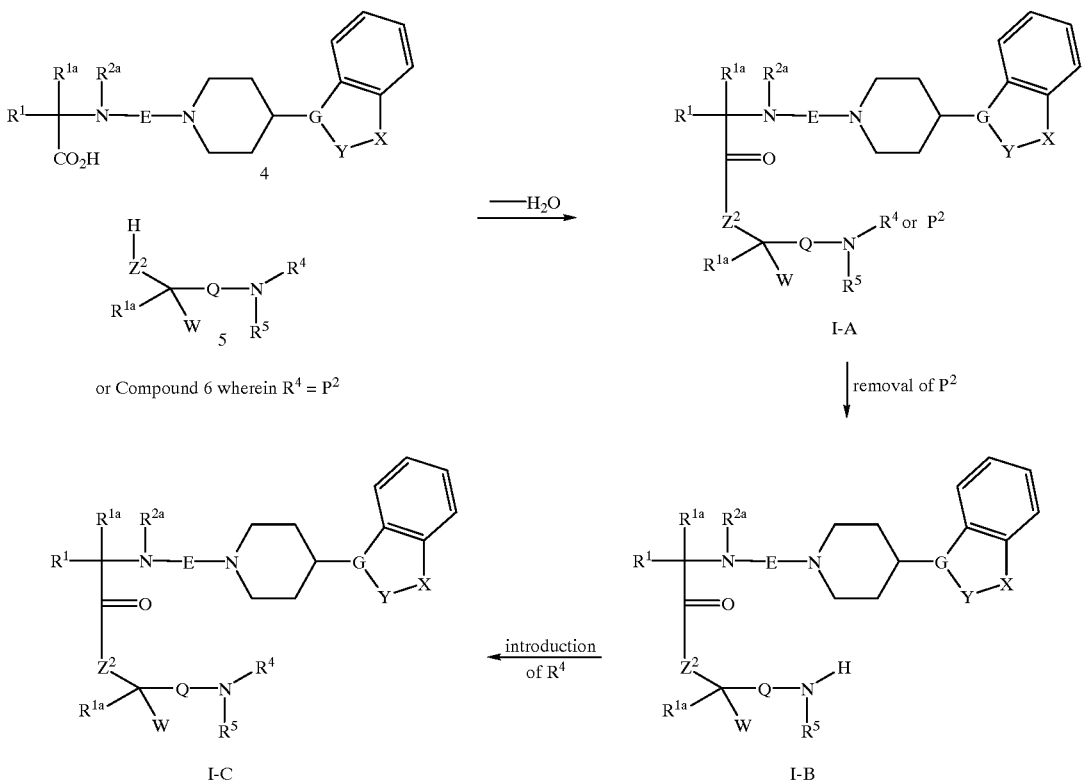

Intermediates of Formula 4 can be coupled to intermediates of formula 5 (or formula 6 wherein $R^4$ is $P^2$) wherein $Z^2$ is oxygen or substituted nitrogen to afford compounds of Formula I-A under standard ester or peptide coupling reaction conditions. $P^2$ is an amine protecting group such as BOC, Cbz, etc. Many of the selectively protected diamines or amino alcohol's of Formula 5 are either commercially available or known in the literature and others can be prepared following literature methods described for analogous compounds. Some of these methods are illustrated in subsequent schemes. Also if $R^4$ or $R^5$ is a hydrogen then the protected amino acids 6 are employed in the coupling reaction, wherein $P^2$ is a protecting group as defined above. The removal of $P^2$ in I-A to afford I-B, can be carried out as noted above. $R^4$ as defined above can then be optionally introduced to yield compound of general formula I-C according to procedures known in the art. For example, if R4 is a substituted a group, it can be introduced by reductive amination or opening of epoxide, or by alkylation by an alkyl halide; if R4 is an amidino group, it can be introduced by the reagents such as 1-amidino-3,5-dimethylpyrazole nitrate (Methods Enzymol., 25b, 558,1972).

SCHEME 3

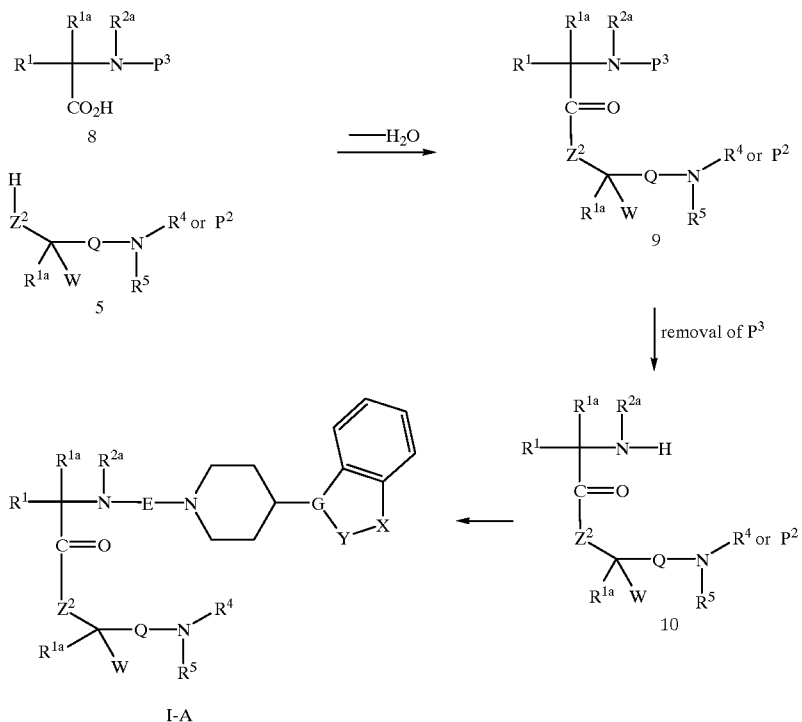

I-A

Alternatively, compounds of Formula I can be prepared starting from compound 5. The protected amino acid derivatives 8 are in many cases commercially available, where P3 is, for exple, BOC, Cbz, Fmoc, and the like. N-Protected amino acid 8 can be coupled to intermediates of formula 5, wherein $Z^2$ is oxygen or substituted nitrogen to afford compounds of Formula 9 under standard ester or peptide coupling reaction conditions. The protecting group in compound 8 is selected with the criteria that its removal can be achieved without removing $P^2$. When the P2 protecting group is removed to afford compound 10, this compound can be further converted to compounds of formula I-A according to the procedures described in Scheme 1 and Scheme 1A. Further elaboration of compound I-A to I-B and I-C are illustrated in Scheme 2.

Formula II

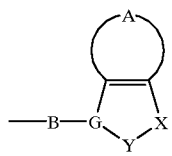

The preparation of compounds of formula II within the scope of this invention may be achieved by methods known in the art. Such methods are illustrated in the following schemes for piperidines with A shown as an unsubstituted fused benzo ring. Analogous methods may be used for the preparation of the other ring compounds or with different substitutions on the ring or both as defined herein. In the interest of clarity, the benzo rings in the following schemes are depicted as being unsubstituted. Compounds bearing additional substituents on the benzo rings are readily prepared by minor modification of the methods herein with procedures known in the art.

SCHEME 4

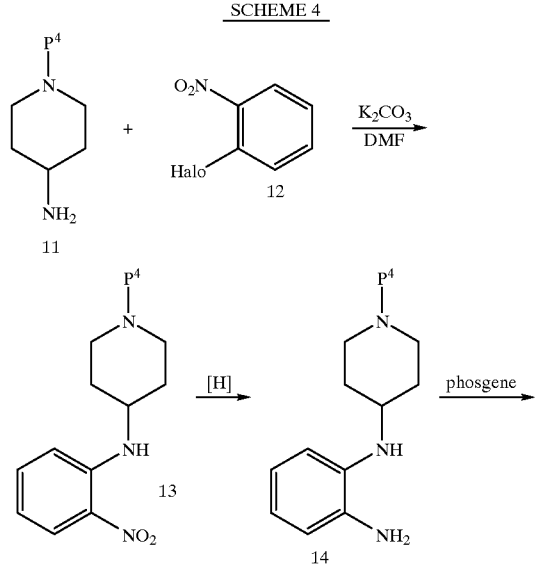

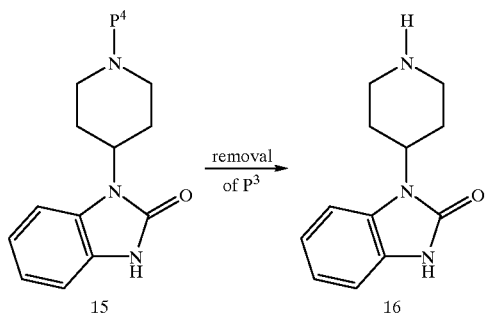

The piperidinylbenzimidazoliione 16 without substitution is commercially available; derivatives with substituents on the benzene ring are prepared by the methods shown in Scheme 4 as described in *J. Med. Chem.*, 30, 814–819 (1987) and U.S. Pat. No. 3,910,930, hereby incorporated by reference. $P^4$ is a protecting group such as benzyl, methyl, BOC, Cbz, ethyloxycarbonyl and the like. Thus, condensation of the commercially available 4-aminopiperidine 11, where $P^4$ is C(O)OEt, with a substituted o-halo nitrobenzene 12 gives the nitro compound 13. Reduction of the nitro group to an amine can be accomplished by catalytic hydrogenation with a catalyst such as Raney Ni, palladium on carbon or platinum on carbon in a protic solvent such as ethanol. Ring closure can be effected by phosgene or its equivalent such as DSC, CDI in the presence of a base. The protecting group $P^4$ can be removed by alkaline hydrolysis in the case of C(O)OEt or can be removed by the standard deprotection conditions as described in Greene, T, and Wuts, P. G. M., *Protective Groups in Organic Synthesis*, John Wiley & Sons, Inc., New York, N.Y. 1991.

SCHEME 5

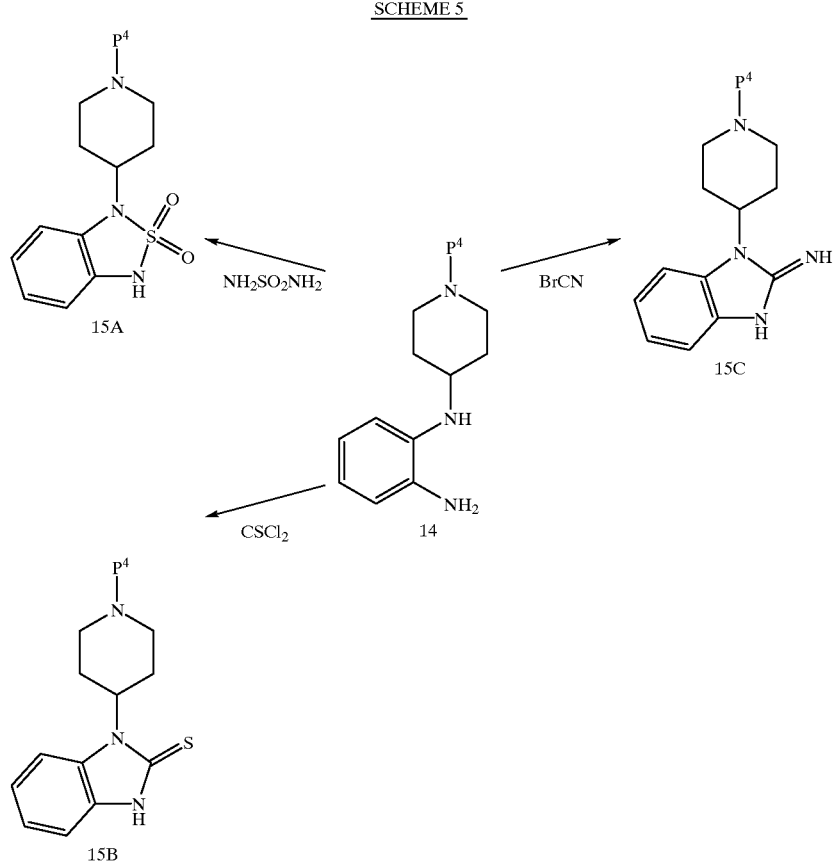

Similarly, other groups as defined by Y in compounds of Formula I can be prepared according to the reactions shown in Scheme 5. Thus, cyclic sulfamide 15 A can be prepared by reacting the diamine 14 and sulfamide; reaction of diamine 14 with thiophosgene or equivalents in the presence of a base gives the thiourea 15B; and reaction with cyanogen bromide yields compound 15C. The protecting group $P^4$ can be removed as described above.

SCHEME 6

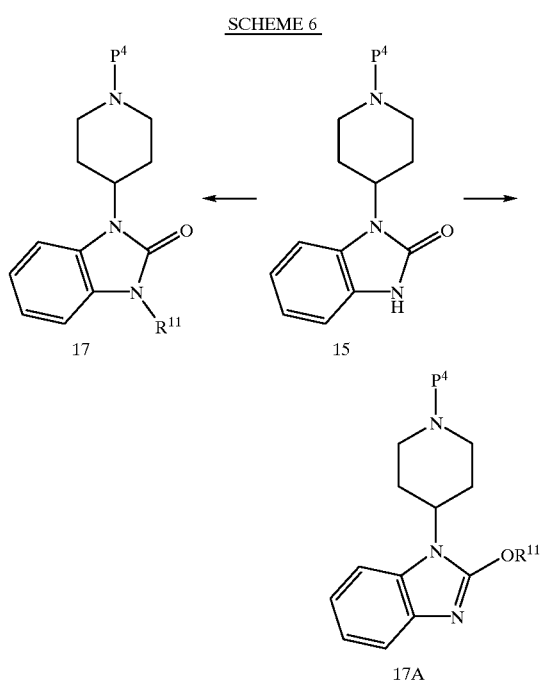

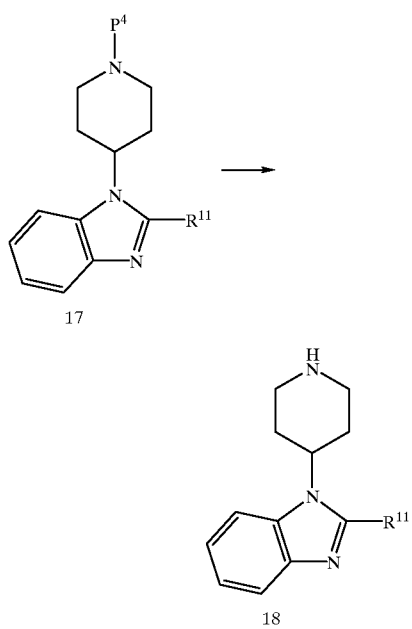

In cases where $R^{11}$ is attached directly to the ring, such compounds can be prepared according to Scheme 7. Coupling compound 14 with a carboxylic acid or equivalents followed by ring closure under dehydration conditions gives compound 17. Removal of the $P^4$ protecting group yields the compound 18.

Benzimidazolones can be modified to introduce substituent $R^{11}$ through alkylation, acylation etc. with appropriate protecting group $P^4$ on the piperidine nitrogen. Similarly, compounds 15 A–C and 14D can be modified as defined by X and Y in formula I. The protecting group $P^4$ is selected in a way that its removal will not cause removal or alteration of $R^{11}$.

SCHEME 7

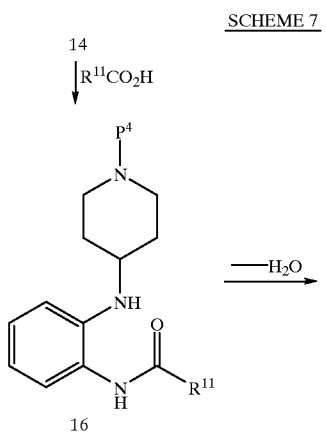

SCHEME 8

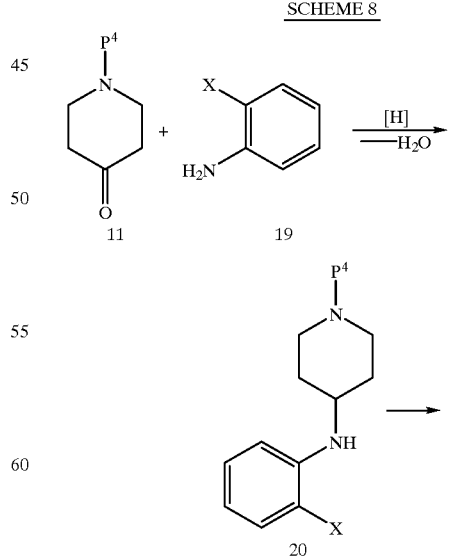

Alternatively, the ortho substituted anine compound 19, where X is —OH, —NH2, —NR¹¹H, —SH, —CH₂OH, —CH₂NH2, —CH₂NR¹¹H, —CH₂SH etc. can be reductively aminated with a protected 4-piperidinone 11 to afford compound 20. Ring closure can be effected through the chemistry discussed above.

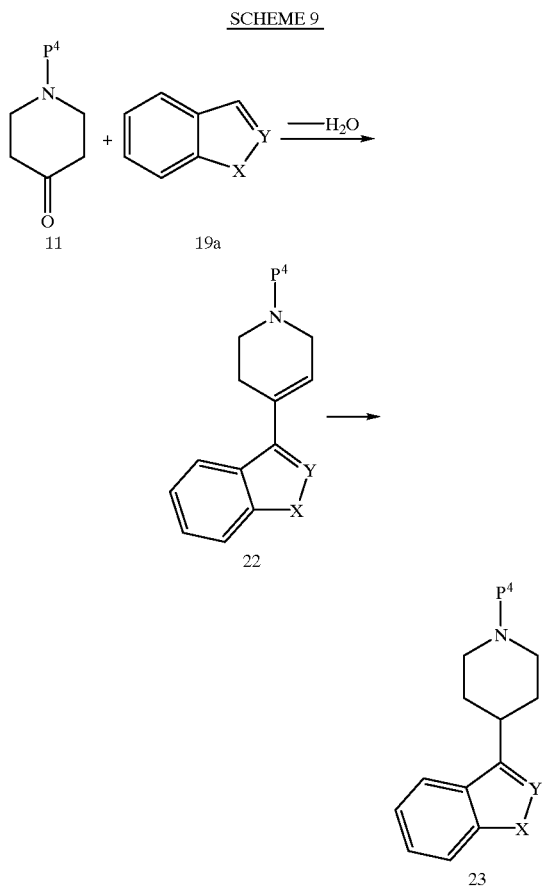

An alternative preparation involves an acid catalyzed coupling reaction of a protected 4-piperidinone 11 with an electron rich aromatic compound such as 19a, where X is O, S, NH or N-alkyl, and Y is CH, COH, COR¹¹, CH or N. The resulting 4-substituted tetrahydropyridines 22 obtained by this method can be elaborated to the instant compounds by utilizing chemistry detailed in Schemes 1–8. The 4-substituted tetrahydropyridines 22 can be hydrogenated by use of platinum or palladium catalysts in a protic solvent like methanol to give piperidines of formula 23 which can also be elaborated to the instant compounds of Formula I.

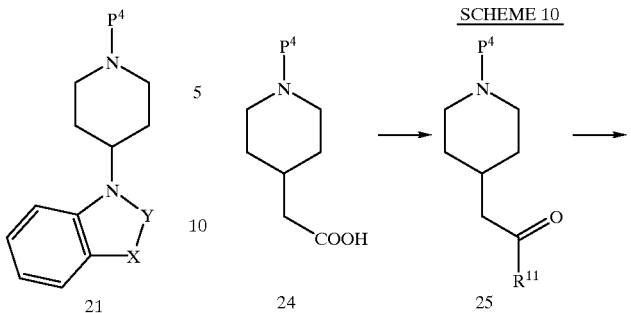

A specific indole embodiment of compound 23, where X=NH and Y=CR¹¹ and R¹¹ is H or alkyl, can be prepared using a Fisher indole synthesis protocol (see *J. Chem. Soc. Chem. Commun.*, 563 (1981); *J. Chem. Soc.*, 3175 (1957)) starting from a ketone or aldehyde and an aromatic hydrazine. Specifically, piperidines of formula 23A may be prepared from the protected piperidine acetic acid compound 24 as shown in Scheme 10. Conversion of the known carboxylic acid 24 to the corresponding aldehyde or ketones can be effected by a variety of conditions known in the art. For example, treatment of 24 with either oxalyl chloride or thionyl chloride in an inert solvent like benzene or carbon tetrachloride gives the corresponding acid chloride that is converted to the aldehyde 25 (R¹¹=H) by a Rosemund reduction. The conversion can also be effected by the Weinreb protocol in which an N,O-dimethyl hydroxylamine amide is reacted with a Grignard reagent to give the ketone or is reacted with LAH to give the aldehyde. Most hydrazines are commercially available or known in the literature and can be prepared accordingly. The condensation of the ketone 25 and hydrazine under the Fisher indole synthesis conditions yields the indole compound 23A. The protecting group P⁴ can be removed by standard protocols and elaborated to the instant compounds by using chemistry presented in Schemes 1–8.

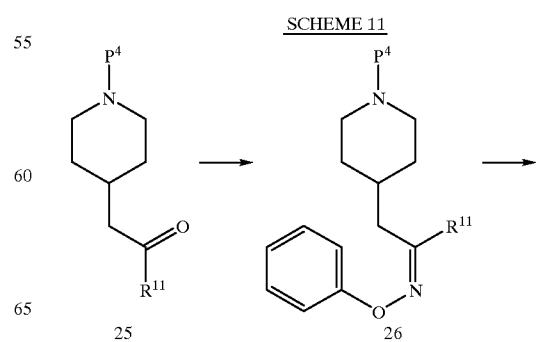

-continued

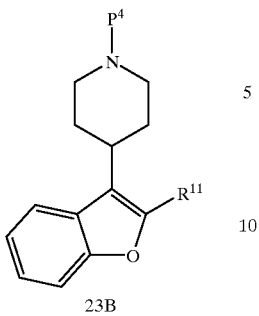

23B

An analogous synthesis of benzofurans of formula 23B from o-aryloximes is exemplified by the transformation of 25 to 26 (see *Tetrahedron Lett.*, 2867 (1967)) as depicted in Scheme 12.

Formula III

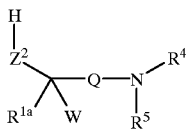

In many cases, compounds of Formula III or its mono protected form within the scopes of this invention are either commercially available or known in the art. In the simplest case where $Z^2$ is NH or O, $R^{1a}$, W, $R^4$ and $R^5$ are H's, Q is $-(CH_2)_x-V-(CH_2)_y-$; where x and y are 1–7, the formula represents diamines some of which are commercially available. Mono Boc protected amine can be prepared by reacting excess diamine with $Boc_2O$ in methanol, where Boc protected amino alcohols can be preprared by reacting the amino alcohol with Boc2O.

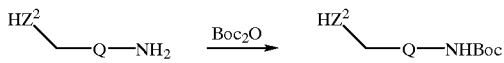

The above procedure is also applicable to compounds of formula III where $R^{1a}$ and W are groups as define defined before.

The following synthetic routes can be used to prepare compounds of Formula III. Using method I (as exemplified by Intermediate 1), 4-aminomethylpyridine is converted to the Boc protected derivative using standard procedures. Introduction of nitrile group at 2-position of the pyridine can be accomplished by the procedure of Shuman et al (*J. Org. Chem.* 55, 738–741, 1990). The nitrite reduction to amine can be done in many ways, illustrated is Raney Ni reduction at high temperature and pressure to give 2-a-minomethfyl-4(t-butyloxycarbonylaminomethyl)-pyridine. The protection pattern can be reversed by protecting the free amine with Cbz followed by removal of Boc. All compounds with a 2-aminomethylpyridine substructure can be prepared this way.

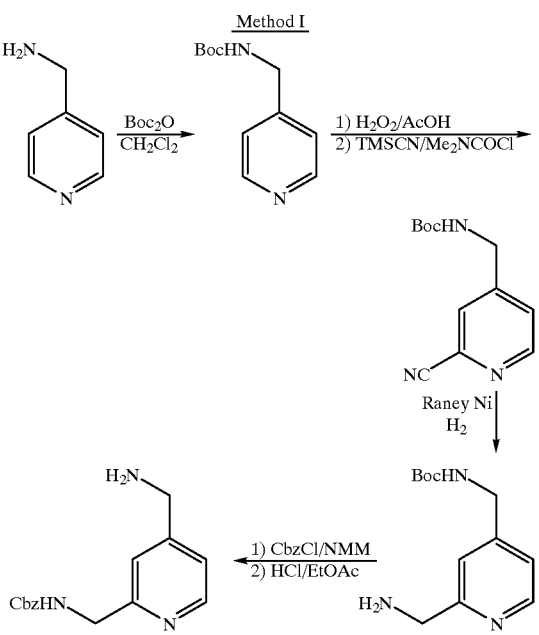

Using Method II (as exemplified by Intermediate 2), a series of pyridines can be prepared that are not easily accessible by Method I. A bromopyridine can be converted to cyano pyridine using CuCN in DMF at reflux. Any amino group can be protected as Boc derivative at this point. Reduction of the cyano group give the desired aminomethyl pyridine. The intermediate cyanide can be modified to afford different substituents.

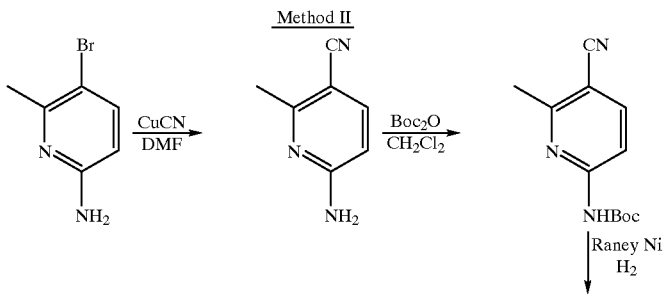

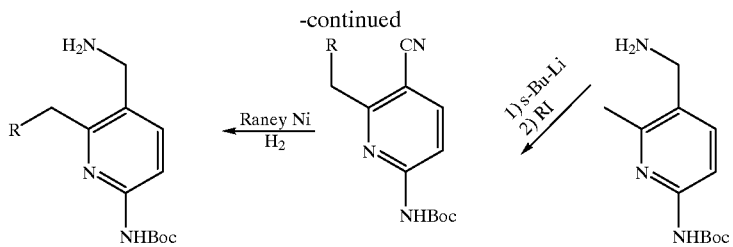

Piperazine incorporated compounds such as 1-(2-aminoethyl)-4t-butyloxycarbonyl-piperazine can be prepared via a nitrile as exemplified by Intermediate 7B. The protection pattern can be reversed through Cbz protection of the primary amine.

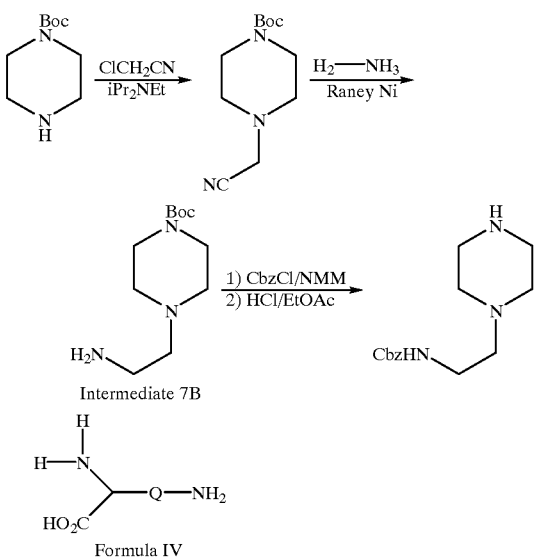

Intermediate 7B

Formula IV

Compounds of Formula IV represent amino acids, which in some cases are commercially available. Amino acids can be modified to give compounds as defilned by the scope of the instant application. For example, with the two amino groups properly protected, the carboxylic acid can be converted into its next higher homologue, or to a derivative of the homologous acid, such as amide or ester by an Arndt-Eistert reaction. The acid can also be converted amides with a variety of amines as defined. The acid can be reduced to alhohol, which can be converted to ether by alkylation or reduced with methods know to those skilled in the art.

The preferred compounds of the invention are any or all of those specifically set forth in the Examples below. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

INTERMEDIATE 1

Step A: 4-(t-butyloxycarbonylaminomethyl)-pyridine N-oxide:

To a stirred solution of 4-aminomethylpyridine (12.48 g, 0.115 mol) in dichloromethane (200 mL) at ambient temperature, was slowly added a solution of Boc2O (26.6 g, 1.05 equiv.) in dichloromethane (100 mL). The resulting mixture was stirred at room temperature for 4 hours, and then evaporated to remove solvents to afford 4-(t-butyloxycarbonylaminomethyl)-pyridine in quantitative yield. The residue was dissolved in acetic acid (30 mL) and hydrogen peroxide (30%, 13 mL) and the resulting solution was stirred at room temperature for one week. The reaction mixte was then evaporated and partition between 3N HCl and dichloromethane. The inorganic layer was extracted with dichloromethane five times and the extracts was combined and washed with small volume of sodium bicarbonate solution. The organic solution was dried and evaporated and purified by 5–10% methanol in dichloromethane to give the N-oxide (4.33 g).

$^1$H NMR (CDCl$_3$, 300 MHz) 8.23 (d, J=7 Hz, 2H), 7.26 (d, J=7 Hz, 2H), 4.30 (d, J=5.6 Hz, 2 H); 1.44 (s, 9H). CI-MS calc. for C$_{11}$H$_{16}$N$_2$O$_3$: 224; Found 225 (M+H), Step B:4-(t-butyloxycarbonylaminomethyl)-2-cyano-pyridine To a stirred solution of the intermediate from the previous step (4.33 g, 19.3 mmol) and trimethylsilyl cyanide (3.35 mL, 1.3 equiv.) in dichloromethane (30 mL), was added dimethyl carbamyl chloride (2.3 mL, 1.3 equiv.) in 10 mL of dichloromethane at ambient temperature. After the reaction mixture had been stirred for one day, 20 mL of 10% potassium carbonate solution was added very slowly. The organic layer was separated and the aqueous layer was washed with dichloromethane twice. The combined organic extracts were dried and purified by silica gel chromatography eluting with 60% ethyl acetate in hexane to give the desired product (2.37 g). $^1$H NMR (CDCl$_3$, 300 MHz) 8.65 (d, J=5 Hz, 1H), 7.61 (d, J=1 Hz, 1H), 7.42 (dd, J=1, 5 Hz, 1H), 5.10 (br.s, 1 H); 4.37 (d. J=6 Hz, 2H), 1.47 (s, 9H). CI-MS calc. for C$_{12}$H$_{15}$N$_3$O$_2$: 233; Found 234 (M+H), Step C: 2-aminomethyl-4(t-butyloxycarbonylaminomethyl)-pyridine:

A solution of the intermediate from the previous step (1.37 g) and Raney Ni (1 g) in 20 mL of ethanol saturated with ammonia under 1000 psi of hydrogen, was stirred at 80° C. for 8 hours. The catalyst was removed by filtration and the solution was evaporated to give the desired compound (1.35 g) as a very thick oil. $^1$H NMR (CDCl$_3$, 300 MHz) 8.40 (d, 3 Hz, 1H), 7.33 (s, 1H), 7.20 (d, J=3 Hz, 1 H), 4.27 (s, 2H), 3.88 (s, 2H), 1.45 (s, 9H).

INTERMEDIATE 1A

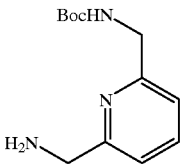

Prepared similarly from 2-aminomethylpyridine:

$^1$H NMR (CD$_3$OD, 400 MHz) 7.74 (dd, J=7.80, 7.70 Hz, 1H), 7.26 (d, J=7.88 Hz, 1H), 7.22 (d, J=3 Hz, 1 H), 4.33 (s, 2H), 3.91 (s, 2H), 1.46–1.40 (m, 9H).

INTERMEDIATE 1B

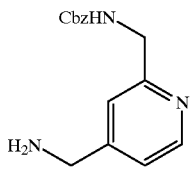

Step A: 4-(t-butyloxycarbonylaminomethyl)-2-(benzyloxycarbonylaminomethyl)-pyridine:

A mixture of 4-(t-butyloxycarbonylaminomethyl)-2-aminomethyl-pyridine(600 mg, 2.63 mmol), NMM (341 ml, 3.03 mmol), 4-DMAP (920 mg, 0.16 mmol) and benzyl chloroformate (433 ml, 3.30 mmol) in methylene chloride (15 ml) was stirred at room temperature overnight. The mixture was diluted with methylene chloride (50 ml) and then washed with water and saturated sodium bicarbonate. The organic layer was dried over sodium sulfate, filtered and evaporated in vacuo to give an oil. The crude product was purified by MPLC using 70% ethyl acetate in hexane as eluting solvent to give the title compound 844 mg (100%).

1H NMR (CDCl3) d=1.45 (s, 3H), 4.25(br, 2H), 4.43 (d, J=5.7 Hz, 2H), 5.10 (s, 2H), 5.28 (br, 1H), 6.10 (br, 1H), 7.05 (d, J=5.1 HZ, 1 H), 7.11 (s, 1 H), 7.32 (m, 5H), 8.40 (d, J=5.1 Hz, 1H)

Step B: 4-aminomethyl-2-(benzyloxycarbonylaminomethyl)-pyridine

The 4-(t-butyloxycarbonylaminomethyl)-2-aminomethyl-pyridine (160 mg, 0.43 mmol) was dissolved in TFA (10 ml) and stirred at room temperature for two hours. The solvent was removed in vacuo. 163 mg of the crude product was collected and brought to next step reaction without further purification.

INTERMEDIATE 2

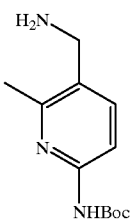

Step A: 2-Amino-5-cyano-6-methyl pyridine:

A mixture of 6-amino-3-bromo-2-methyl-pyridine (20 g, 0.107 mol) and copper (I) cyanide (11.0 g, 0.123 mol) in DMF (25 mL) was heated to reflux for 4 h. The DMF was evaporated in vacuo and the residue was partitioned between ethyl acetate and 10% sodium cyanide solution. The organic layer was washed with 10% sodium cyanide solution and brine, dried (Na2SO4) and evaporate in vacuo to a brown solid. This was dissolved in a minimum amount of ethyl acetate and the product was precipitated by adding hexane. The mixture was filtered to give the title compound (12 g, 85%) as a brown powder:

$^1$H NMR (CDCl$_3$, 400 MHz) 7.54 (d, J=8.6 Hz, 1H), 6.33 (d, J=8.6 Hz, 1 H), 4.97 (br. s, 2 H), 2.56 (s, 3 H).

Step B: 2-t-Butoxycarbonylamino-5-cyano-6-methyl-pyridine:

A mixture of 2-amino-5-cyano-6-methyl-pyridine (8.0 g, 60 mmol), (Boc)20 (19.64 g, 90 mmol), 4-methylmorpholine (6.60 mL, 60 mmol), and DMAP (1.10 g, 9.0 mmol) in 150 mL of methylene chloride and TBIF (75 mL each) was stirred overnight. The solvent was removed in vacuo and the residue was taken into ethyl acetate (200 mL). The mixture was washed with 1.5 N HCl and brine, saturated NaHCO$_3$, and then with brine. The organic layer was dried over magnesium sulfate, filtered, and evaporated in vacuo to give an oil. The crude product was purified by flash column chromatography (gradient 0–15% ethyl acetate/hexane) to give the title compound (13.52 g, 97%) as a white solid:

1H NMR (CDCl$_3$) d 1.52 (s, 9H) 2.62 (s, 3H) 7.46 (br. s, 1 H), 7.80 (d, J=8.8 Hz, 1 H) 7.88 (d, J=8.8 Hz, 1 H). FAB-MS C12H15N3O2 Calc: 233 Found: 234

Step C: 2-t-Butoxycarbonylamino-5-methylamino-6-methyl-pyridine:

A mixture of 2-t-butoxycarbonylamino-5-cyano-6-methyl-pyridine (7.88 g, 33.80 mmol) and Raney—Nickel (6.30 g) in ammonia saturated ethanol (100 mL) was heated to 80° C. at 1000 psi for 10 hours. The reaction mixture was cooled to room temperature and filtered through celite. The filtrate was evaporated in vacuo and the residue was purified using flash column chromatography (1–2% NH4OH/ 10–20% methanol/90–80% methylene chloride) to give the title compound (6.92 g, 86% yield).

1H NMR (CDCl$_3$) d 1.50 (s, 9H) 2.43 (s, 3H) 3.81 (s, 3H), 7.23 (br. s, 1 H), 7.57 (d, J=8.3 Hz, 1 H) 7.70 (d, J=8.3 Hz, 1 H).

INTERMEDIATE 2A

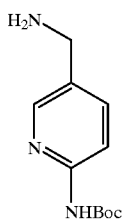

Prepared similarly from 2-amino-5-bromopyridine.

INTERMEDIATE 2B

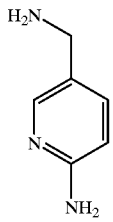

A mixture of 6-aminonicotinamide (15 g) and LAH (1M in THF, 200 ml, 0.2 mol) in anhydrous THF (300) was refluxed for one week. The reaction mixture was cooled to 0° C. and quenched by adding cold water dropwise until the bubbling ceased. The solvent was removed in vacuo and the residue was taken to ethyl acetate. The mixture was washed with brine and saturated sodiu,m bicarbonate. The organic layer was dried over sodium sulfate, filtered and evaporated in vacuo. The crude product was purified by flash column chromatography using 80% CH2Cl2–18% MeOH-2% NH4OH as eluent to give the title compound as yellow solid (5.53 g, 41%).

1H (CD3OD) d 3.64 (s, 2H), 6.57 (d, J=8.4 Hz, 1H), 7.48 (dd, J=8.4 Hz, J=2.7 Hz, 1H), 7.83 (d=2.4 Hz, 1H).

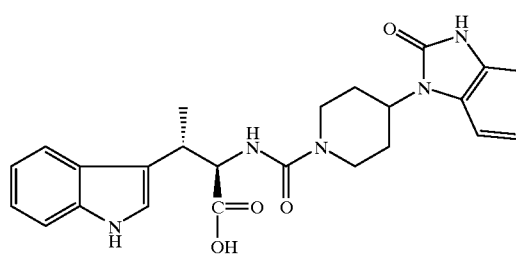

Step A:

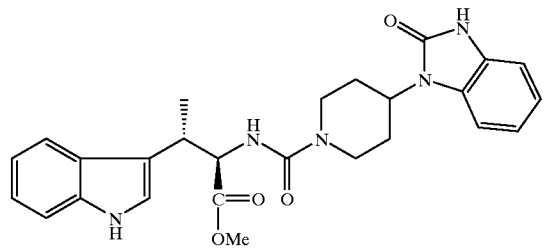

b-Methyl-D-Tryptophan methyl ester (6.00 g, 25.9 mmol) was combined with disuccinimidyl carbonate (6.95 g, 27.1 mmol) and DIEA (11.3 mL, 64.6 mmol) in dichloromethane. After stirring the reaction mixture for 0.5 h, 4-(2-keto-1-benzinuidazolinyl)-piperidine (5.90 g, 27.1 mmol) was added and the mixture was permitted to stir over night. The reaction mixture was diluted with dichloromethane, and washed in succession with 1N HCl (100 mL), saturated NaHCO3 solution (100 mL) and brine (100 mL), dried over MgSO4, filtered and concentrated. The resulting crude product was purified by MPLC (silica, 5% methanol/ethyl acetate) to give 7.55 g of a white solid.

Step B:

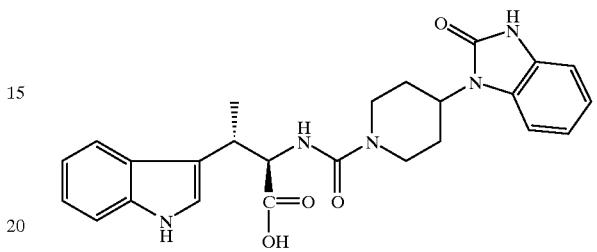

The coupled product from the previous step (7.55 g, 15.9 mmol) was dissolved in THF (30 mL), treated with LiOH (2.67 g, 63.6 mmol) in 1:1 EtOH/water (60 mL) and stirred for 4 h at room temperature. The pH was adjusted to ~2–3 by addition of 3N HCl and the resulting solution was extracted with ethyl acetate 3 times. The combined organic layers were washed with brine, dried over MgSO4, filtered and concentrated to give 6.50 g of a white solid.

INTERMEDIATE 4

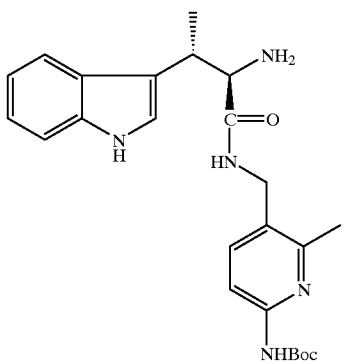

Step A:

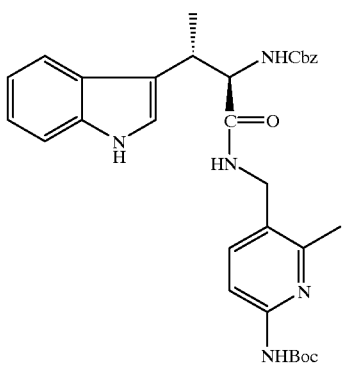

To a mixture, cooled to 0° C. by ice/water bath, of N-Cbz-b-methyl-tryptophan (500 mg, 1.42 mmol), HOBt (190 mg, 1.42 mmol) and Intermediate 2 (337 mg, 1.42 mmol) in methylene chloride and DMF (10/2 mL) was added EDC (544 mg, 2.84 mmol) and stirred overnight. The reaction mixture was evaporated in vacuo and the residue was dissolved in ethyl acetate. The solution was washed with 1.5N HCl and brine, and saturated NaHCO$_3$. The organic layer was dried over magnesium sulfate, filtered, and evaporated in vacuo to give the product as a yellow oil. The crude product was purified by MPLC (80% ethyl acetate/hexane) to give the title compound (583 mg, 72%) as a white powder.

Step B:

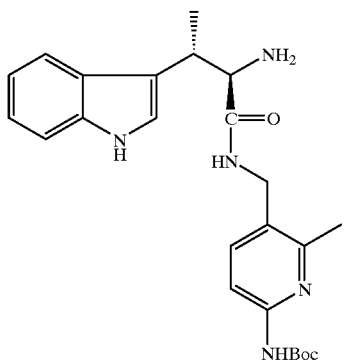

A mixture of the intermediate from the previous step (553 mg, 0.967 mmol) and 10% Pd-C (55 mg) in THF (20 mL) was stirred at room temperature under a balloon of hydrogen overnight. The reaction was filtered through celite and evaporated in vacuo to give the title compound (407 mg, 96%). The compound was used without further purification.

H NMR (CD$_3$OD, 400 MHz) 7.65 (d, J=8.08 Hz, 1H), 7.47 (d, J=8.53 Hz, 1H), 7.34 (d, J=8.21 Hz, 1H), 7.10-7.01 (m, 4H), 4.20 (d, J=15.0 Hz, 1H), 4.09 (d, J=15.0 Hz, 1H) 3.63 (d, 6.82 Hz, 1H) 3.45 (p, 1H) 2.24 (s, 3H) 1.52 (s, 9H) 1.36 (d, J=7.15 Hz, 3H).

FAB-MS C24H31N5O3 Calc: 437 Found: 438

INTERMEDIATE 5

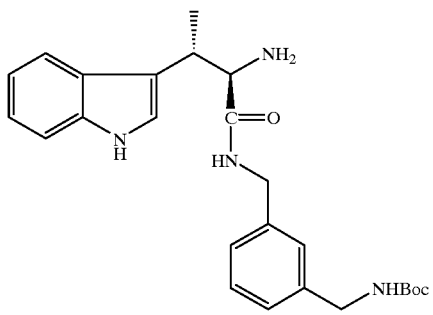

Similarly prepared as Intermediate 4 using mono-t-butyloxycarbonyl-1,3-xylenediamine

INTERMEDIATE 6

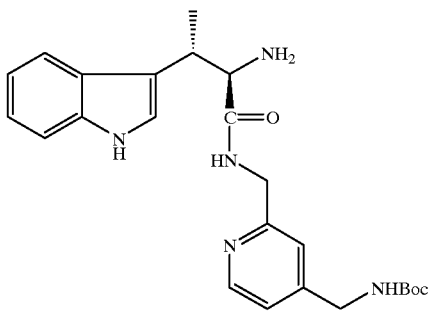

Similarly prepared as Intermediate 4 using Intermediate I Cbz intermediate:

H NMR (CD$_3$OD, 400 MHz) 8.27 (d, J=5.0 Hz, 1H), 7.97 (s), 7.64 (d, J=8.0 Hz, 1H), 7.26-7.14 (m, 5H), 7.11-6.97 (m, 4H), 6.78 (s, 1H), 5.07 (d, 1H) 5.05 (d, 1H) 4.50 (d, J=8.26 Hz, 1H), 4.24 (d, 1H), 4.19 (d, 1H), 4.09 (d, 1H), 4.05 (d, 1H) 3.60 (p, 1H) 1.44 (s, 9H), 1.40 (d, J=7.14 Hz, 3H).

Title compound:

H NMR (CD$_3$OD, 400 MHz) 8.33 (d, J=5.22 Hz, 1H), 7.97 (s), 7.685 (d, J=8.0 Hz, 1H), 7.33 (d, 8.0 Hz, 1H) 7.16-7.00 (m, 5H), 4.45 (d, 1H) 4.43 (d, 1H), 4.17 (s, 2H), 3.76 (d, J=5.55 Hz, 1H), 3.60 (p, 1H) 1.43 (s, 9H), 1.35 (d, J=7.14 Hz, 3H).

INTERMEDIATE 7

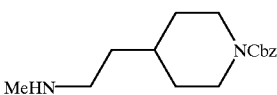

Step A:

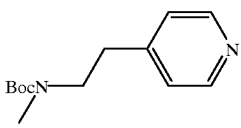

To a stirred solution of 4-[2-(methylamino)ethylpyridine (10.0 g, 73.4 mmol) in tetrahydrofuran (200 mL) at 0° C., was slowly added a solution of Boc$_2$O (16.0 g, 73.4 mmol) in tetrahydrofuran (200 mL). The resulting mixture was stirred at room temperature overnight, and then evaporated to remove solvent and purified by MPLC eluting with 1% methanol in ethyl acetate to give the Boc compound (16.00 g, 92% yield) as an oil.

Step B:

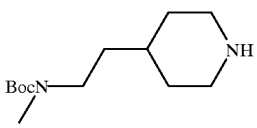

A mixture of the intermediate from the previous step (4.54 g, 19.2 mmol) and 450 mg of platinum (IV) oxide in 20 mL acetic acid was stirred at room temperature under a balloon of hydrogen overnight. The reaction mixture was filtered through celite and evaporated in vacuo to give the residue which was partition between saturated NaHCO₃ solution and dichloromethane. The aqueous layer was extracted with dichloromethane three times and the extracts were combined and dried over magnesium sulfate, filtered and concentrated to give the product in quantitative yield. ¹H NMR (CDCl₃, 400 MHz) d3.19(s, 2H), 3.03(d, J=12 Hz, 2H), 2.78(s, 3H) 2.53(t, J1, J2=12 Hz), 2.45 (s, 2H), 1.66 (d, J=12.4 Hz, 2H), 1.44 (s, 9H), 1.40 (m., 3H), 1.11(m., 2H). ESI-MS calc. for C13H26N2O2: 242; Found 243(M+1).

Step C:

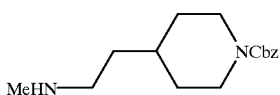

To a mixture of above product (0.75 g, 3.1 mmol) and triethyl amine ( 410 mL, 3.73 mmol.) in dichloromethane (20 mL) at 0° C., was slowly added benzyl chloroformate (488 mL, 3.42 mmol). The resulting mixture was stirred at room temperature overnight. The reaction mixture was washed with saturated NaHCO₃ solution, 1N HCl and brine, dried over magnesium sulfate, filtered, and concentrated to give the crude product in quantitative yield. ¹H NMR (CDCl₃, 400 MHz) d 7.36 (m., 5H),5.10(s, 2H) 4.15(br. s, 2H), 3.22(br. s, 2H), 2.80(s, 3H), 2.70(br. s, 2H), 1.60 (m, 3H), 1.40(s, 9H), 1.40(m, 2H), 1.10(m, 2H). The crude product was dissolved in ethyl acetate at 0° C. and HCl (gas) was bubbled through this solution for 2 min. This solution was evaporated to give a white solid. ¹H NMR (CDCl₃) d9.43(br. s, 1H), 7.35(m, 5H), 5.08(br. s, 2H), 4.13(br. s, 2H), 2.94 (m, 2H), 2.72(br. s, 2H), 2.63 (m, 3H), 2.07(br. s, 1H), 1.75(m, 2H), 1.63(m, 2H), 1.15(m, 2H). ESI-MS calc. for C16H24N2O2: 276; Found: 277(m+1).

EXAMPLE 1

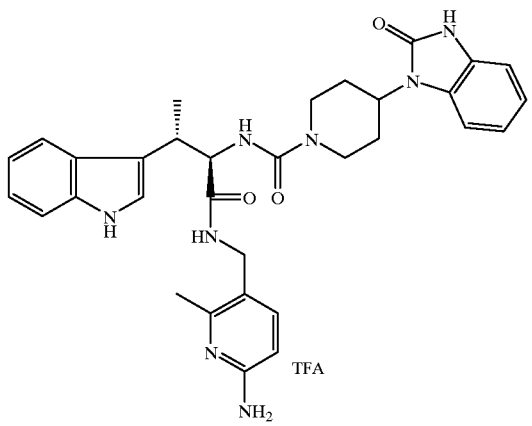

Step A:
To a mixture of Intermediate 3 (276 mg, 0.60 mmol), Intermediate 2 (147 mg, 0.62 mmol), HOBt (81 mg, 0.6 mmol) in methylene chloride was added EDC(173 mg, 0.9 mmol) in portions at 0° C. The mixture was stirred at room temperature overnight and then diluted with methylene chloride, and then washed with water and saturated sodium bicarbonate. The organic layer was dried over sodium sulfate, filtered and evaporated in vacuo. The crude product was purified by flash column chromatography using 5% methanol in ethyl acetate as eluent solvent. Evaporation of solvent in vacuo provided the Boc intermediate as white foam solid (328 mg, 80%). FAB-MS C37H42N8O5 Calc: 680 Found 681

Step B:

The intermediate from previous step(260 mg, 0.38 mmol) was dissolved in TFA (10 ml) and stirred at room temperature for two hours. Evaporation of the solvent in vacuo provided the title product as light brown solid (262 mg, 99%).

¹H NMR (CDCl3, 400 MHz) d 8.05 (m, 1H), 7.50 (d, J=8 Hz, 1H), 7.30 (d, J=8 Hz, 1H), 7.2-7.0 (m, 7H), 6.92 (t, J=7.2 Hz, 1H), 6.45 ( d, J=8.8 Hz), 4.42 (m, 1H), 4.15 (d, J=10.4 Hz, 1H), 4.32-4.20 (m, 2H), 4.05 (dd, J=14.0 Hz, 6.4 Hz, 1H), 3.73 (dd, J=14.0 Hz, J=1.6 Hz, 1H), 3.52-3.40 (m, 1H), 3.48-2.93 (m, 2H), 2.45-2.25 (m, 2H), 2.07 (s, 3H), 1.80 (d, J=12.4 Hz, 2H), 1.45(d, J=6.9 Hz, 3H)

FAB-MS C32H36N8O3 Calc: 580 Found 581

EXAMPLE 2

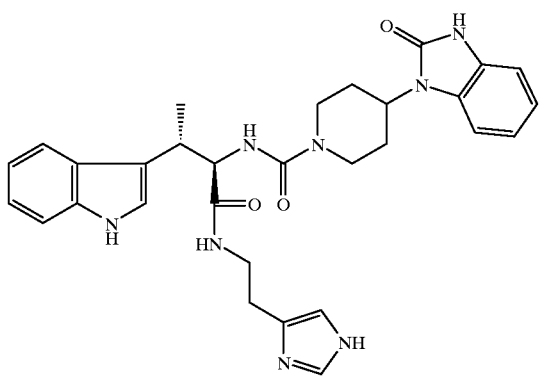

Intermediate 3 (131 mg, 0.283 mmol) was combined with histamine dihydrochloride (104 mg, 0.567 mmol), HOBt (77 mg, 0.57 mmol), and DIEA (200 mL, 1.13 mmol) in DCM/DMF (1:1, 7 mL), cooled to 0° C. and treated with EDC (108 mg, 0.567 mmol). The reaction mixture was allowed to warm to room temperature and was stirred overnight. The reaction mixture was diluted with DCM (50 mL) and 1N HCl (50 mL). The organic layer was separated and washed with saturated NaHCO₃ solution (40 mL) and brine (40 ml). The organic layer was dried over MgSO₄, filtered and concentrated. During the work up an insoluble viscous oil precipitated out. This material was dissolved in methanol and combined with the crude product obtained from concentration of the DCM. Purification by preparative TLC (silica, 1.8% NH₃ solution-30%, 18.2% methanol, 80% DCM) afforded 51.1 mg of pure product.

¹H NMR (CD₃OD, 400 MHz) d 8.70 (s, 1H), 7.63 (d, J=8 Hz, 1H), 7.30 (d, J=8 Hz, 1H), 7.16 (s, 1H), 7.14-6.98 (m, 7H), 4.45 (m, 1H, 4.37 (d, J=8.8 Hz, 1H), 4.26-4.15 (m, 2H), 3.60 (m, 1H), 3.16 (dt, J=2.4, 6.8 Hz, 2H), 3.03-2.91 (m, 2H), 2.50 (m, 2H), 2.45-2.19 (m, 2H), 1.79 (m, 2H), 1.45 d, J=7.2 Hz, 3H).

ESI-MS calc for C30H34N8O3: 554; Found: 555 (M+H).

EXAMPLE 3

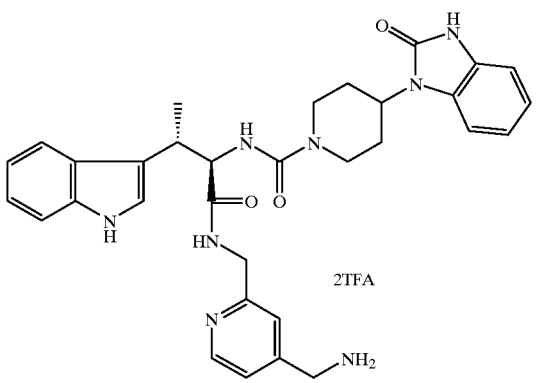

2TFA

Step A:

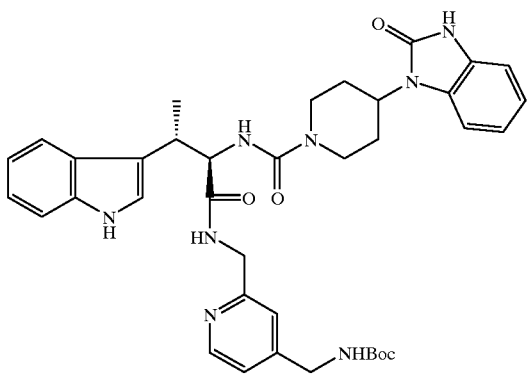

To a mixture of Intermediate 3 (100 mg, 0.21 mmol), Intermediate 1 (57 mg, 0.23 mmol), HOBt (30 mg, 0.21 mmol) in methylene chloride (8 ml) was added EDC (60 mg, 0.32 mmol) in portions at 0° C. The mixture was stirred at room temperature overnight, and then diluted with methylene chloride and washed with water and saturated sodium bicarbonate. The organic layer was dried over sodium sulfate, filtered and evaporated in vacuo. The crude product was purified by MPLC using 10% methanol in ethyl acetate as eluent. Evaporation of solvent in vacuo provided the title product as white foam solid (120 mg, 85%).

FAB-MS $C_{37}H_{42}N_8O_5$ Calc: 680, Found 681

Step B:

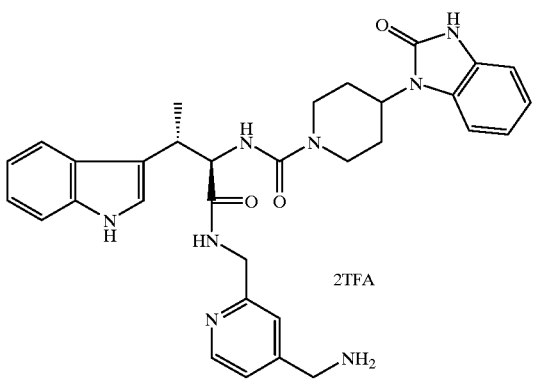

2TFA

The intermediate from previous step (110 mg, 0.16 mmol) was dissolved in TFA (8 ml) and stirred at room temperature for two hours. Evaporation of the solvent in vacuo provided the title product as light brown solid (109 mg, 98%).

$^1$H NMR (CD3OD, 300 MHz) d 8.57 (d, J=5.3 Hz, HI), 7.64 (d, J=7.8 Hz, 1H), 7.55 (d, J=5.7 Hz, 1H), 7.50 (s, 1H), 7.33 (d, J=8.1 Hz, 1H), 7.22 (s, 1H), 7.15-6.95 (m, 6H), 4.52-4.11 (m, 8H), 3.75-3.60( m, 1H), 3.05-2.90 (m, 2H), 2.45-2.25 (m, 1H), 2.25-2.10(m, 1H), 1.80-1.70 (m, 2H), 1.51 (d, J=7.2 Hz, 3H).

FAB-MS $C_{32}H_{36}N_8O_3$ Calc: 580, Found 581

EXAMPLE 4

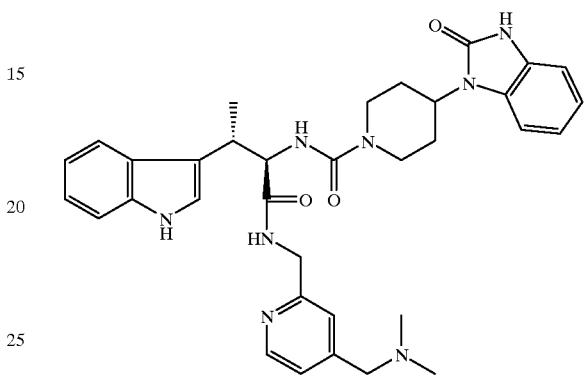

To a mixture of the title compound of Example 3 (200 mg, 0.24 mmol) and NaOAc (203 mg, 2.4 mmol) in methanol was added formaldehyde (37% in water, 136 mg, 1.68 mmol). The mixture was stirred at room temperature for 30 min., and then to this mixture was added NaBH3CN (30 mg, 0.48 mmol). The reaction mixture was stirred at room temperature overnight and then evaporated to dryness. The residue was taken to ethyl acetate and washed with saturated. NaHCO3. The organic layer was dried over sodium sulfate, filtered and evaporated in vacuo. The crude product was purified by Prep. TLC using 85% CH2Cl2–14% MeOH–1% NH4OH as eluent to give the title compound as white solid (38 mg).

FAB-MS $C_{34}H_{40}N_8O_3$ Calc: 608, Found 609

EXAMPLE 5

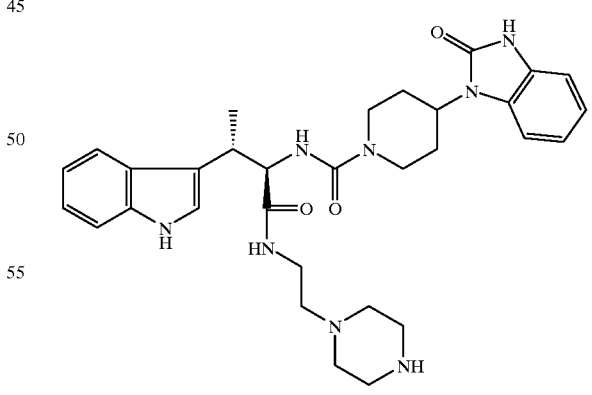

Step A: 1-cyanomethyl-4-butoxycarbonylpiperazine:

A solution of N-t-butoxycarbonylpiperazine (10 g, 53.8 mmol), chloroacetonitrile (4 mL, 1.05 equiv.) and DIEA (10 mL, 1.1 equiv.) in dichloromethane (300 mL) was refluxed overnight. The reaction mixture was evaporated to give a thick oil, which was tritiated with ether (30 mL) and the organic layer was separated and stored in freezer overnight and filtered. The ether solution was evaporated to give the product as a white solid (12.7 g).

Step B: 1-(2-aminoethyl)-4butoxycarbonylpiperazine:

A solution of 1-cyanomethyl-4-butoxycarbonylpiperazine (12 g) in ethanol (100 mL) saturated with ammonia, was hydrogenated over Raney Ni (5 g) at 1000 psi and 80° C. for 8 hours. The resulting mixture was filtered and evaporated to give 1-(2-aminoethyl)-4-butoxycarbonylpiperazine as a solid (12 g).

Step C:

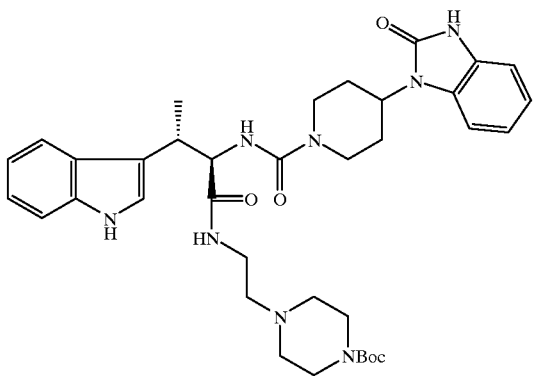

To a solution of Intermediate 3 (100.0 mg, 0.2169 mmol), 1-(2-aminoethyl)-4-butoxycarbonylpiperazine (60.0 mg, 0.260 mmol), and HOBt(32 mg, 0.228 mmol) in dichloromethane (5 mL) was added EDC(50.0 mg, 0.260 mmol). The resulting mixture was stirred at room temperature overnight. The reaction mixture was washed with saturated NaHCO3 solution, 1N HCl and brine, dried over magnesium sulfate, filtered and concentrated to give the crude product. The crude product was purified by MPLC (20% methanol in ethyl acetate) to give 100 mg as white solid. ESI-MS calc. for C36H48N8O5: 672; Found: 673(M+1).

Step D:

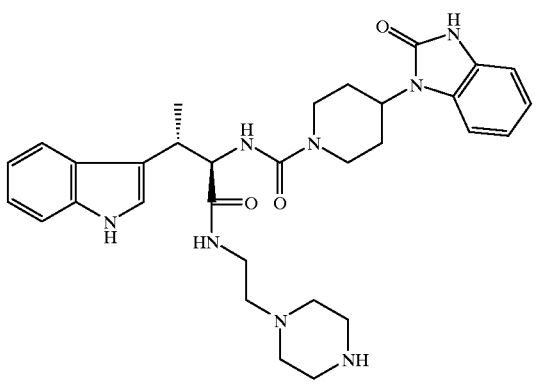

To a solution of the Boc intermediate from the previous step (100 mg) in ethyl acetate (5 mL) at 0° C. was bubbled HCl (gas) for 2 min. After 15 minutes, the solution was evaporated to give the title compound as a white solid.

$^1$H NMR(CD$_3$OD, 400 MHz) 7.63(d, J=8 Hz, 1H), 7.36 (d, J=8.0 Hz, 1H), 7.24(S, 1H), 7.17(m, 3H), 7.06(m, 3H), 4.43(m, 1H), 4.30 (d, J=8.8 Hz, 1H), 4.20 (m, 2H), 3.66 (m, 6H), 3.30 (m, 5H), 2.96 (m, 2H), 2.85 (m, 2H), 2.37 (m, 1H), 2.27 (m, 1H), 1.78 (d, J=11.6 Hz, 2H), 1.50(d, J=6.8 Hz, 3H) ESI-MS calc. for C31H40N8O3: 572; Found: 573 (M+1).

EXAMPLE 6

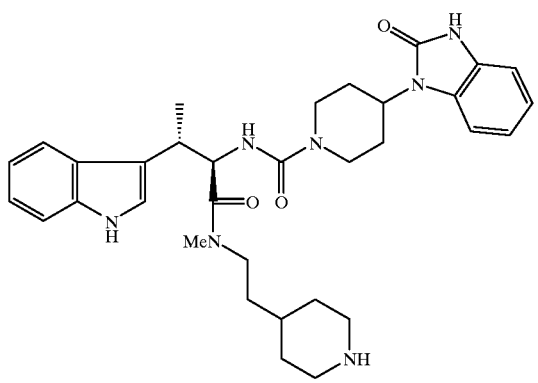

To the solution of "top piece" acid (50.0 mg, 0.108 mmol) in dichloromethane, was added amine (38.0 mg, 1.19 mmol), HOBt (16 mg, 0.114 mmol) and EDC(25.0 mg, 0.130 mmol). The resulting mixture was stirred at room temperature overnight. The reaction mixture was washed with saturated NaHCO3 solution, 1N HCl and brine, dried over magnesium sulfate, filtered and concentrated to give the crude product. The crude product was purified by MPLC (7% methanol in ethyl acetate) to give 36.0 mg as white solid. ESI-MS calc. for C41H49N7O5: 719; Found: 720(M+1). A mixture of the intermediate from the previous step (36 mg, 0.050 mmol) and 10% Pd(OH)2-C(7.2 mg) in ethyl alcohol was stirred at room temperature under a balloon of hydrogen overnight. The reaction solution was filtered through celite and 12N HCl (4.2 mL, 0.050 mmol) was added. The resulting solution was concentrated to give the white solid.

$^1$H NMR (CD$_3$OD, 400 MHz) 7.62(d, J=8.0 Hz, 1H), 7.34(d, J=8.0 Hz, 1H), 7.21(m, 2H), 7.05 (m, 5H), 4.46 (m, 1H), 4.30 (m, 1H), 3.58(m, 1H), 3.40(m, 1H), 3.30(m, 1H), 3.20(m, 1H), 3.00(m, 1H), 2.80(m, 2H), 2.69(m, 1H), 2.70(s, 3H), 2.55(m, 1H), 2.40(m, 1H), 2.00(m, 1H), 1.82(m, 1H), 1.68(m, 1H), 1.58(m, 1H), 1.55(d, J=7.2 Hz), 1.25(m, 2H), 1.12(m, 2H), 0.97(m, 1H), 0.85(m, 2H);

ESI-MS calc. for C33H43N7O3: 585 (free base); Found: 586(M+1).

EXAMPLE 7

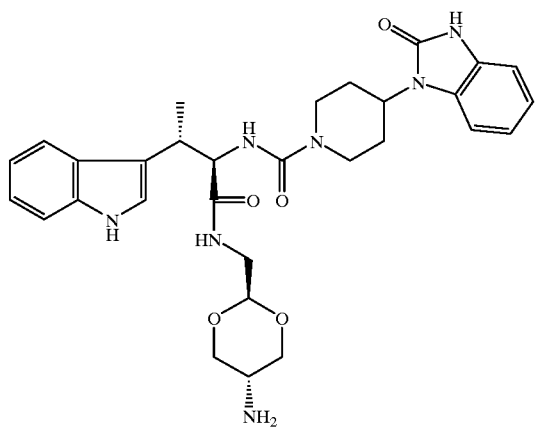

Step A:

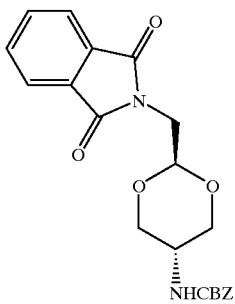

Step C:

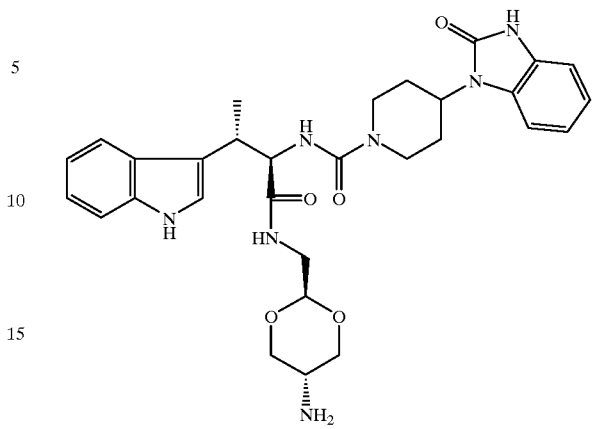

A stirred mixture of N-Cbz-serinol (497 mg, 2.21 mmol), prepared using standard procedures from commercially available serinol oxalate and Cbz-Cl, phthalimidoacetaldehyde diethyl acetal (Aldrich, 581 mg, 2.21 mmol) and TsOH (21 mg, 0.11 mmol) in toluene (10 mL) was heated to reflux for 6 h. The resulting solution was cooled and evaporated in vacuo. Purification by flash chromatography (dry loaded on silica, 30% ethyl acetate/hexanes to 40% ethyl acetate/hexanes) afforded a 4:1 trans/cis mixture (107 mg) and a 1:4 trans/cis mixture (300 mg). The trans isomer was crystallized from absolute ethanol.

To a solution of Intermediate 3 (85.5 mg, 0.185 mmol), aminomethyl dioxane from the previous step (54.3 mg, 0.204 mmol), and HOBt (38 mg, 0.28 mmol) in DCM (5 mL) at 0° C. was added EDC (53 mg, 0.28 mmol). The mixture was allowed to warm to room temperature and stir for 16 h. The reaction mixture was diluted with DCM (40 mL) and washed with 1N HCl (30 mL), saturated NaHCO₃ solution (30 mL) and brine (30 mL). The organic layer was dried over MgSO₄, filtered and concentrated. Purification by MPLC (silica, 5% ethyl acetate/hexane) afforded the pure product as a white solid (101.9 mg). This was then dissolved in 1:1 THF/ethanol (10 mL), and stirred at room temperature under H₂ (1 atm) with Pd(OH)₂/C (20%, 20 mg) for 5 h. The reaction mixture was filtered through celite (the filter cake was washed with methanol, 30 mL) and the filtrate was treated with concentrated HCl solution (12 mL) and concentrated to give the target compound as a yellow/white solid (80 mg).

$^{1}$H NMR (CD$_{3}$OD, 400 MHz) d 7.64 (d, J=8 Hz, 1H), 7.36 (d, J=8 Hz, 1H), 7.17 (s, 1H), 7.15-7.00 (m, 6H), 4.49 (d, J=8.8 Hz, 1H), 4.45 (m, 1H), 4.21 (m, 2H), 4.11 (m, 2H), 3.91 (m, 1H), 3.58 (m, 1H), 3.48-3.22 (m, 3H?), 3.18 (m, 1H?), 2.99 (m, 3H), 2.42-2.22 (m, 2H), 1.78 (m, 2H), 1.46 (d, J=7.2 Hz, 3H).

ESI-MS calc for C30H37N7O5: 575; Found: 576 (M+H).

EXAMPLE 8

Step B:

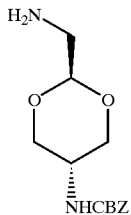

To a suspension of the product from the above reaction (106 mg, 0.268 mmol) in absolute ethanol was added hydrazine (1 M solution in ethanol, 0.268 mmol) and the mixture was heated at reflux for 1 h. The resulting suspension was cooled and evaporated in vacuo. 2 M HCl (5 mL) was added and the mixture was warmed to 50° C. for 5 min. to give a suspension which was cooled and filtered. The solids were washed with more 2 M HCl. The resulting solution was washed with DCM (2X) then basified with 50% NaOH solution (cooling in an ice bath), and the mixture was extracted with ethyl acetate (2X). The combined extracts were dried over Na₂SO₄, filtered and evaporated to give 57 mg of product as a waxy solid.

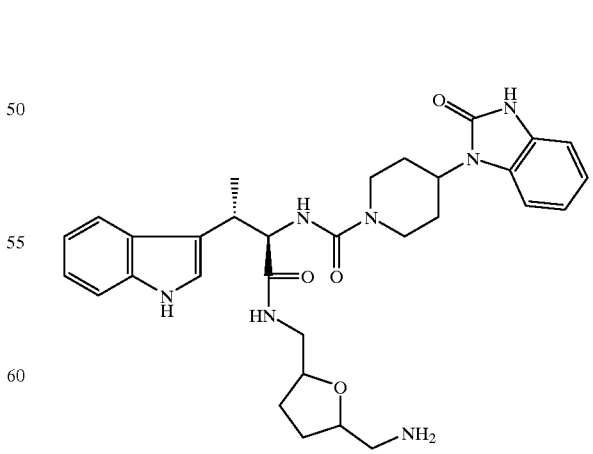

Step A: 2-(N-t-Butoxycarbonylaminomethyl)-5-hydroxymethyl tetrahydrofuran

2-Aminomethyl-5-hydroxymethyl tetrahydrofuran (2.4 g, 18 mmol) was dissolved in THF (40 mL) and treated with a solution of Boc2O (3.99 g, 18.3 mmol) in THF (20 mL) over about 10 min. The reaction mixture was stirred for 24 h and then concentrated to afford the BOC amino protected compound which was purified by MPLC (silica, 1% methanol/ethyl acetate).

Step B: 2-(N-t-Butoxycarbonylaminomethyl)5-azidomethyl tetrahydrofuran

The product from the previous step (2.66 g, 11.5 mmol) was combined with triethyl amine (3.2 mL, 23 mmol) and DMAP (ca. 200 mg) in DCM (40 mL). The resulting solution was cooled to 0° C. and treated with MsCl (0.980 mL, 12.7 mmol), dropwise over 2 min. After 5 h the reaction mixture was diluted with DCM (75 mL) and washed with 1N HCl (75 mL), saturated NaHCO$_3$ solution (75 mL) and brine (75 mL). The organic layer was dried over MgSO$_4$, filtered and concentrated to afford 2.88 g of mesylate. The mesylate (2.87 g, 9.28 mmol) was combined with NaN$_3$ (1.21 g, 18.6 mmol) in DMF (30 mL) and heated at 70° C. for 15 h. The reaction mixture was diluted with ether (200 mL) and washed with water (5×100 mL) and brine (100 mL), dried over MgSO$_4$, filtered and concentrated to give 2.18 g of azide.

Step C: 2-(N-t-Butoxycarbonylaminomethyl)-5-aminomethyl tetrahydrofuran

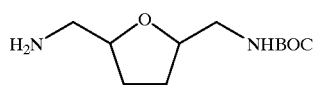

The azide prepared in the previous step (2.0 g, 7.8 mmol) was dissolved in methanol (40 mL) and stirred under H$_2$ (1 atm) with Pd(OH)$_2$/C (200 mg, 20%) for 16 h. The reaction mixture was filtered through celite (filter cake was washed with additional methanol) and concentrated to give 1.77 g of the desired amine.

ESI-MS calc for C11H22N2O3: 230; Found 231 (M+H).

Step D:

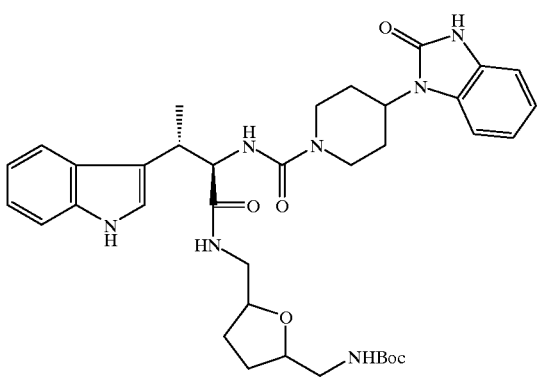

To a solution of Intermediate 3 (169 mg, 0.367 mmol), 2-(N-t-Butoxycarbonylaminomethyl)-5-aminomethyl tetrahydrofuran (110 mg, 0.477), and HOBt (84 mg, 0.62 mmol) in DCM (10 mL) at 0° C. was added EDC (120 mg, 0.624 mmol). The reaction mixture was permitted to warm to room temperature and stir overnight. The mixture was diluted with DCM (40 mL) and washed in turn with 1N HCl (30 mL), saturated NaHCO$_3$ solution (30 mL) and brine (30 mL). The organic phase was dried over MgSO$_4$, filtered and concentrated. The residue was purified by MPLC (silica 9.5% methanol/ethyl acetate) to afford 218.4 mg of pure product.

ESI-MS calc for C36H47N7O6: 673; Found: 674 (M+H).

Step E:

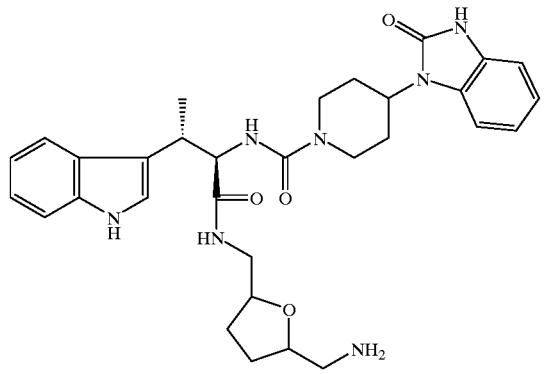

The BOC protected intermediate so formed from the previous step (199 mg) was dissolved in ethyl acetate/DCM (~3:1) and HCl (g) was bubbled through this solution for 3 min. The reaction mixture was then concentrated to afford the target compound (187 mg). ESI-MS calc for C31H39N7O4: 573; Found: 574 (M+H).

EXAMPLE 9

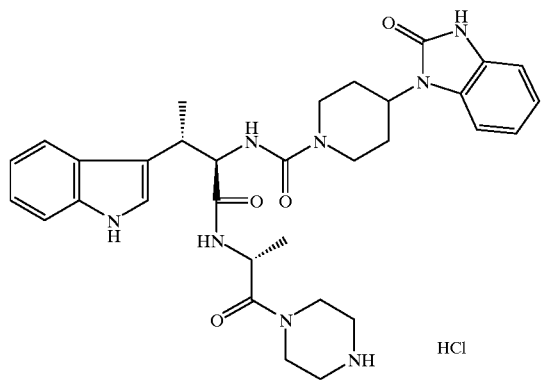

Step A

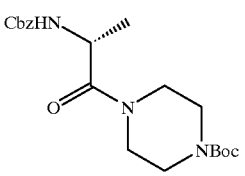

To a mixture of Cbz-D-Ala-OH (3.35 g, 15 mmol), PyBrop (8.04 g, 17.25 mmol) and diethyl isopropyl amine (5.3 ml, 30 mmol) in CH2Cl2 was added Boc piperizine (2.79 g, 15 mmol). The mixture was stirred at room temperature overnight, then diluted with CH2Cl2 and washed with 1N HCl aqueous solution and saturated NaHCO3. The organic layer was dried over sodium sulfate, filtered and evaporated in vacuo. The crude product was purified by flash column chromatography using 50% ethyl acetate in hexane to provide the title compound as white foam solid (4.69 g, 80%).

1H NMR (CD3OD, 300 MHz) d 7.34-7.25 (m, 5H), 5.07 (s, 2H), 4.61 (q, J=6.9 Hz, 1H), 3.7-3.3 (m, 8H), 1.47 (s, 9H), 1.28 (d, J=6.9 Hz, 3H).

FAB-MS $C_{20}H_{29}N_3O_5$ Calc: 391, Found 392

Step B:

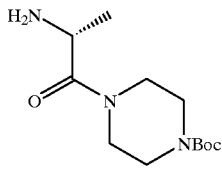

A mixture of the product from the previous step (4.68 g, 11.95 mmol) and 20% Pd(OH)2-C (468 mg) in methanol (100 ml) was stirred at room temperature under a balloon of hydrogen for two hours. The reaction mixture was filtered through celite and evaporated in vacuo to give the title compound as white solid (2.91 g, 94%).

FAB-MS $C_{12}H_{23}N_3O_3$ Calc: 257, Found 258

Step C:

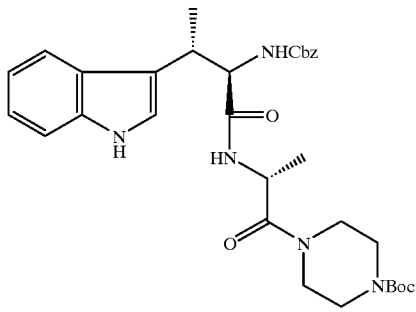

To a mixture of the product from the previous step (1.65 g, 6.43 mmol), Z-b-me-Trp (2.15 g, 6.10 mmol) and HOBt (0.83 g, 6.12 mmol) in CH2Cl2 (60 ml) was added EDC (1.76 g, 9.18 mmol) in portions at 0° C. The mixture was stirred at room temperature for four hours, and then diluted with CH2Cl2 and washed with water and saturated NaHCO3. The organic layer was dried over sodium sulfate, filtered and evaporated in vacuo. The crude product was purified by flash column chromatography using 80% ethyl acetate in hexane to provide the title compound as white foam solid (3.08 g, 85%).

FAB-MS $C_{32}H_{41}N_5O_6$ Calc: 591, Found 592.

Step D:

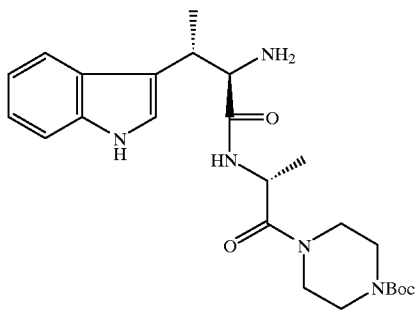

A mixture of the product from the previous step (3.0 g, 5.07 mmol) and 20% Pd(OH)2-C (300 mg) in methanol (100 ml) was stirred at room temperature under a balloon of hydrogen for two hours. The reaction mixture was filtered through celite and evaporated in vacuo to give the title compound as white solid (2.19 g, 94%).

FAB-MS $C_{24}H_{35}N_5O_4$ Calc: 457, Found 458

Step E:

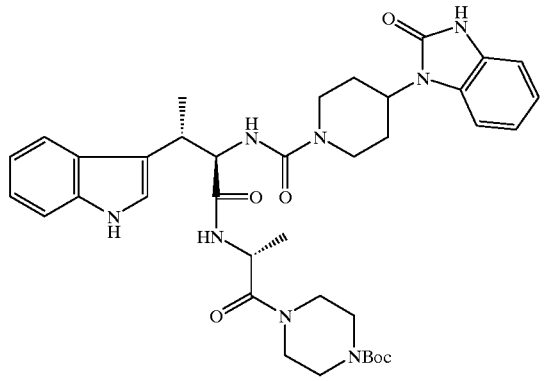

To a mixture of the product from the previous step (200 mg, 0.44 mmol) and N,N'-disuccinimidyl carbonate (112 mg, 0.44 mmol) in CH2Cl2 (8 ml) was added DIEA (77 ml, 0.44 mmol). The mixture was stirred for 30 min. at room temperature, then 4-(2-keto-1-benzimidazolinyl)-piperidine (95 mg, 0.44 mmol) and DIEA (77 ml, 0.44 mmol) were added. The mixture was stirred at room temperature overnight, then diluted with CH2Cl2 and washed with saturated NaHCO3. The organic layer was dried over sodium sulfate, filtered and evaporated in vacuo. The crude product was purified by MPLC 5% MeOH in ethyl acetate to provide the title compound as white foam solid (257 mg, 83%).

FAB-MS $C_{37}H_{48}N_8O_6$ Calc: 700, Found 701.

Step B:

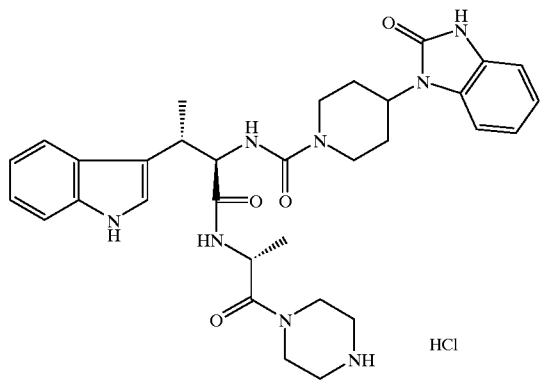

To the solution of the product from the previous step (247 mg, 0.35 mmol) in ethyl acetate (10 ml) was bubbling HCl gas for 30 seconds (until it was saturated) at 0° C., the mixture was stirred at room temperature for 5 min. The solvent was removed in vacuo to provided the title compound as a solid (244 mg, 100%).

FAB-MS $C_{32}H_{40}N_8O_4$ Calc: 600, Found 601.

The examples listed in Table I below were prepared using the same or similar protocols as for the examples (1–9) listed above.

TABLE I

| Example | X | Y | diamine |
|---|---|---|---|
| 10 | H | H | tetrahydropyran-2,6-diyl-bis(methylamine) (HN–CH–O–CH–NH₂ ring) |
| 11 | H | H | 2-methyl-5-(aminomethyl)-6-aminopyridinium |
| 12 | ethyl | H | 2,4-bis(aminomethyl)pyridine |

Biological Assays

The ability of compounds of the present invention to act as somatostatin agonist can be determined by the following in vitro assays, which is disclosed in Rens-Domiano, et al., Pharmacological Properties of Two Cloned Somatostatin Receptors, *Mol. Pharm.*, 42: 28–34 (1992) and incorporated herein.

Receptor Expression Constructs

Mammalian expression vectors containing full length coding sequences for hSSTR1–5 were constructed as follows: Fragments of genomic DNA carrying the various human somatostatin receptors were inserted into the multiple cloning site of pcDNA3 (Invitrogen). The fragments used were a 1.5-kb PstI-XmnI fragment for hSSTR1, 1.7-kb BamHI-HindIII fragment for hSSTR2, 2.0-kb NcoI-HindIII fragment for hSSTR3, a 1.4-kb NheI-NdeI fragment for hSSTR4, and a 3.2-kb XhoI-EcoRI fragment for hSSTR5.

Transfection

CHO-K1 cells were obtained from American Type Culture Collection (ATCC) and grown in alpha-MEM containing 10% fetal calf serum. Cells were stably transfected with DNA for all 5 hSSTRs using lipofectamine. Neomycin resistant clones were selected and maintained in medium containing G418 (400 μg ml).

Receptor binding assay.

Cells were harvested 72 hr after transfection to 50 mM Tris-HCl, pH 7.8, containing 1 mM EGTA, 5 mM $MgCl_2$, 10 μml leupeptin, 10 μg/ml pepstatin, 200 μg/ml bacitracin, and 0.5 μg/ml aprotinin (buffer 1) and were centrifuged at 24,000× g for 7 min at 4°. The pellet was homogenized in buffer 1 using a Brinkman Polytron (setting 2.5, 30 sec). The homogenate was then centrifuged at 48,000 μg for 20 min at 4° C. The pellet was homogenized in buffer 1 and the membranes were used in the radioligand binding assay. Cell membranes (approximately 10 μg of protein) were incubated with $^{125}I$-$Tyr^{11}$-somatostatin (0.2 nM; specific activity, 2000 Ci/mmol; NEN) in the presence or absence of competing peptides, in a final volume of 200 μl, for 30 min at 25°. Nonspecific binding was defined as the radioactivity remaining bound in the presence of 100 nM somatastatin. The binding reaction was terminated by the addition of ice-cold 50 nM Tris-HCl buffer, pH 7.8, and rapid filtration with 12 ml of ice-cold Tris HCl buffer, and the bound radioactivity was counted in a gamma scintillation spectrophotometer (80% efficiency). Data from radioligand binding studies were used to generate inhibition curves. $IC_{50}$ values were obtained from curve-fitting performed with the mathematical modeling program FITCOMP, available through the National Institutes of Health-sponsored PROPHET System.

Inhibition of forskolin-stimulated cAMP accumulation.

Cells used for cAMP accumulation studies were subcultured in 12-well culture plates. COS-7 cells were transfected 72 hr before the experiments. Culture medium was removed from the wells and replaced with 500 μl of fresh medium containing 0.5 mM isobutylmethylxanthine. Cells were incubated for 20 min at 37°. Medium was then removed and replaced with fresh medium containing 0.5 mM isobutylmethylxanthine, with or without 10 μM forskolin and various concentrations of test compound. Cells were incubated for 30 min at 37°. Medium was then removed, and cells were sonicated in the wells in 500 μL of 1N HCl and frozen for subsequent determination of cAMP content by radioimmunassay. Samples were thawed and diluted in cAMP radioimmunassay buffer before analysis of cAMP content using the commercially available assay kit from NEW/DuPont (Wilmington, Del.).

Inhibition of growth hormone release.

Functional activity of the various compounds was evaluated by quantitating release of growth hormone secretion from primary cultures of rat anterior pituitary cells. Cells were isolated from rat pituitaries by enzymatic digestion with 0.2% collagenase and 0.2% hyaluronidase in Hank's balanced salt solution. The cells were suspended in culture medium and adjusted to a concentration of $1.5 \times 10^5$ cells per milliliter, and 1.0 ml of this suspension was placed in each well of a 24-well tray. Cells were maintained in a humidified 5% $CO_2$-95% air atmosphere at 37° C. for 3 to 4 days. The culture medium consisted of Dulbecco's modified Eagle's medium containing 0.37% $NaHCO_3$, 10% horse serum, 2.5% fetal bovine serum, 1% nonessential amino acids, 1% glutamine, 1% nystatin, and 0.1% gentamycin. Before testing compounds for their capacity to inhibit GH release, cells were washed twice 1.5 hours before and once more immediately before the start of the experiment with the above culture medium containing 25 mM Hepes (pH 7.4). The compounds of the insant invention were tested in quadruplicate by adding them in 1 ml of fresh medium to each well and incubating them at 37° C. for 15 min. After incubation, the medium was removed and centrifuged at 2000 g for 15 min to remove any cellular material. The supernatant fluid was removed and assayed for GH by radioimmunoassay.

The compounds of this invention were found to inhibit the binding of somatostatin to its receptor at an $IC_{50}$ of about 30 pM to about 3 μM.

What is claimed is:

1. A compound represented by structural formula I:

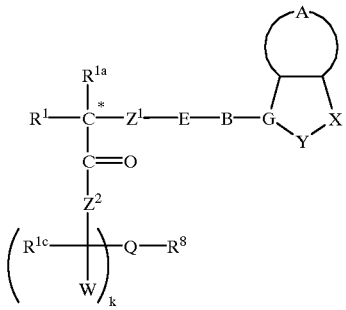

or a pharmaceutically acceptable salt or hydrate thereof, wherein:

$R^1$ is selected from the group consisting of: $C_{1-10}$alkyl, aryl, aryl($C_{1-6}$alkyl)-, $C_{3-7}$cycloalkyl($C_{1-6}$alkyl)-, $C_{1-5}$alkyl-K-($C_{1-5}$alkyl)-, aryl($C_{0-5}$alkyl)-K-($C_{1-5}$alkyl)-, and $C_{3-7}$cycloalkyl($C_{0-5}$alkyl)-K-($C_{1-5}$alkyl)-, wherein K is -O-, -S(O)$_m$-, -N($R^2$)C(O)-, -C(O)N($R^2$)-, -$CR^2$=$CR^2$- or -C≡C-, the alkyl portions of which being optionally substituted with by 1 to 5 halogen groups, S(O)$_m R^{2a}$, 1 to 3 of $OR^{2a}$ groups or C(O)$OR^{2a}$, and wherein aryl is selected from the group consisting of: phenyl, naphthyl, biphenyl, quinolinyl, isoquinolinyl, indolyl, azaindolyl, pyridyl, benzothienyl, benzofuranyl, thiazolyl and benzimidazolyl, said aryl groups being unsubstituted or substituted with 1 to 3 $C_{1-6}$alkyl or halo groups, 1 to 2 -$OR^2$ groups, methylenedioxy, -S(O)$_m R^2$, 1 to 2 -$CF_3$ groups, -$OCF_3$, -$NO_2$, -N($R^2$)C(O)($R^2$), -C(O)$OR^2$, -C(O)N($R^2$)$_2$, 1H-tetrazol-5-yl, -$SO_2$N($R^2$)($R^2$), -N($R^2$)$SO_2$ phenyl, or -N($R^2$)$SO_2 R^2$;

$R^2$ is selected from the group consisting of: H, $C_{1-8}$alkyl, -(CH$_2$)$_t$-aryl and $C_{3-7}$cycloalkyl, and where two $R^2$ groups are present, they optionally are joined to form a $C_{3-8}$ring, optionally interrupted by O, S or $NR^{3a}$, in which $R^{3a}$ is H or $C_{1-6}$alkyl optionally substituted by OH;

t is an integer from 0 to 3;

and when $R^2$ is other than H, $R^2$ is optionally substituted with 1 to 5 halogen groups, S(O)$_m R^{2a}$, 1 to 3 of $OR^{2a}$ groups or C(O)$OR^{2a}$, $R^{2a}$ is H or $C_{1-3}$alkyl optionally substituted by OH;

m is 0, 1 or 2;

$R^{1a}$ is H or $C_{1-3}$alkyl;

$Z^1$ is selected from the group consisting of -O-, -CH$_2$- and $NR^{2a}$;

E is selected from the group consisting of-$SO_2$-, -CO(C($R^2$)$_2$)$_n$-, -C(=N-CN)-, -C(=N-NO$_2$)- and -C(=N-$SO_2$N($R^2$)$_2$)-;

n is an integer from 0 to 3;

B is

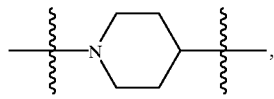

where attachment points are indicated by lines (§), said group being optionally substituted by $C_{1-6}$alkyl;

represents an aromatic or non-aromatic ring structure wherein:

G is N,

Y is -C(O)-, and

X is -N($R^{11}$)-;

$R^{11}$ is H, $C_{1-8}$alkyl, $CF_3$, $CH_2 CF_3$, -(CH$_2$)$_p OR^2$, -(CH$_2$)$_p$N($R^2$)$_2$, -(CH$_2$)$_p$N($R^2$)C(O)N($R^2$)$_2$, -(CH$_2$)$_p$N($R^2$)C(O)$R^2$, -(CH$_2$)$_2$-heteroaryl, -(CH$_2$)$_p$N($R^2$)$SO_2 C_{1-4}$alkyl, -(CH$_2$)$_p$C(O)N($R^2$)$_2$ or -(CH$_2$)$_p$C(O)$OR^2$, wherein heteroaryl is selected from tetrazolyl, oxadiazolyl, imidazolyl and triazolyl, said heteroaryl being optionally substituted with $R^2$, $OR^2$, $CF_3$ or N($R^2$)$_2$ and where p is 0–3;

is a 6 membered fused aryl group, said aryl group being optionally substituted with 1–3 $C_{1-6}$alkyl or halo groups, -$OR^2$, N($R^2$)$_2$, methylenedioxy, -S(O)$_m R^2$, -$CF_3$, -$OCF_3$, -$NO_2$, -N($R^2$)C(O)($R^2$), -C(O)$OR^2$, -C(O)N($R^2$)$_2$, 1H-tetrazol-5-yl, -$SO_2$N($R^2$)$_2$, -N($R^2$)$SO_2$ phenyl, -N($R^2$)C(O)N($R^2$)$_2$ or -N($R^2$)$SO_2 R^2$;

$Z^2$ is selected from the group consisting of -O-, -CH$_2$-,-CHR$^{2b}$- and NR$^{2b}$-, wherein $R^{2b}$ is selected from the group consisting of: H, $C_{1-8}$alkyl, -(CH$_2$)$_t$-aryl, -(CH$_2$)$_n CO_2 R^2$, -(CH$_2$)$_n$CON($R^2$)$_2$ and -(CH$_2$)$_n OR^2$, and when $Z^2$ is NR$^{2b}$ it can optionally be linked to $R^{1c}$, Q or W to form a C5–8 ring, which is optionally interrupted by O, S(O)$_m$ or NR$^{2a}$;

$R^{1c}$ is selected from the group consisting of: H, -(CH$_2$)$_q SR^2$, -(CH$_2$)$_q OR^2$ and $C_{1-8}$alkyl;

W is selected from the group consisting of: H, $C_{1-8}$alkyl, (CH$_2$)$_t$-aryl, -(CH$_2$)$_q$C(O)$OR^2$, -(CH$_2$)$_q OR^2$,-(CH$_2$)$_q$OC(O)$R^2$, -(CH$_2$)$_q$C(O)$R^2$, -(CH$_2$)$_q$C(O)(CH$_2$)$_t$aryl, -(CH$_2$)$_q$C(O)N($R^2$)$_2$, -(CH$_2$)$_q$N($R^2$)C(O)$R^2$, -(CH$_2$)$_q$N($R^2$)$SO_2 R^2$, -(CH$_2$)$_q$N($R^2$)C(O)N($R^2$)$_2$, -(CH$_2$)$_q$OC(O)N($R^2$)$_2$, -(CH$_2$)$_q$N($R^2$)C(O)$OR^2$, -(CH$_2$)$_q$N($R^2$)$SO_2$N($R^2$)$_2$, -(CH$_2$)$_q$S(O)$_m R^2$ and -(CH$_2$)$_t$-heteroaryl, the heteroaryl portion of which is selected from: tetrazolyl, oxadiazolyl, thiadiazolyl, triazolyl and pyrazinyl, optionally substituted with $R^2$, N($R^2$)$_2$ or $OR^2$, and when $R^2$ is other than H, said $R^2$, (CH$_2$)$_q$ and the (CH$_2$)$_t$ portions of W are optionally substituted with 1 to 2 $C_{1-4}$alkyl, $OR^{2a}$, C(O)$OR^{2a}$ or 1–3 halo groups, and the aryl and heteroaryl portions of W are optionally substituted with 1 to 3 halo groups, -$OR^2$, -CON($R^2$)$_2$, -C(O)$OR^2$, $C_{1-4}$alkyl, -S(O)$_m R^2$, N($R^2$)$_2$, $CF_3$ or 1H-tetrazol-5-yl;

k is 0 or 1, such that when k is 0, Q is attached directly to $Z^2$;

Q represents a member selected from the group consisting of:

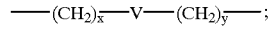

-continued

——(CH₂)ₓ—C(R⁷)(R⁷ᵃ)—(CH₂)ᵧ—;

——(CH₂)ₓ—V—C(R⁷)(R⁷ᵃ)—(CH₂)ᵧ—;

——(CH₂)ₓ—C(R⁷)(R⁷ᵃ)—V—(CH₂)ᵧ—,

——(CH₂)ₓ—V—(CH₂)ᵧ—C(R⁷)(R⁷ᵃ) and

—C(R⁷)(R⁷ᵃ)—(CH₂)ₓ—V—(CH₂)ᵧ— wherein x and y are independently 0, 1, 2, 3, 4, 5 or 6;
V is a $C_{3-10}$ saturated, partially saturated or aromatic mono- or bicyclic ring system, containing 1–4 N atoms and/or 1–2 O or S atoms, said ring system being optionally substituted with 1 to 3 halo groups, -OR², -CON(R²)₂, -C(O)OR², $C_{1-4}$alkyl, -S(O)ₘR², (CH₂)ₜN(R²)₂, CF₃ or 1H-tetrazol-5-yl;
R⁷ and R⁷ᵃ are independently CF₃ or R²;
R⁸ is selected from the group consisting of H,

-NR⁴R⁵,

-C(=NR⁹)N(R¹⁰)₂ and

-N⁺(R⁴)₃;

R⁴ and R⁵ are independently selected from the group consisting of: R², -C(=NR²)N(R²)₂, -C(=NCN)N(R²)₂, -C(=NC(O)R²)N(R²)₂, C(=NSO₂R²)N(R²)₂, -C(=NNO₂)NR², heteroaryl, -C(O)N(R²)₂, -C(=S)N(R²)₂, -C(O)R², 2,2,2-trifluoroethyl, 3,3,3-trifluoropropyl and -(CH₂)ₜ-cyclopropyl, or
R⁴ and R⁵ are taken together and represent

—(CH₂)ₐ—Lₐ(CH₂)ₑ— wherein $L_a$ is -C(R²)₂-, -O-, -S(O)ₘ- or -N(R²)-, and d and e are independently 0 to 3 such that d plus e equals 2–6,
and said heteroaryl and R² other than H being optionally substituted with 1–3 $C_{1-6}$alkyl groups, 1–7 halo groups, N(R²)₂, OR², N(R²)C(O)R², C(O)N(R²), OC(O)R², S(O)ₘR², CF₃, OCF₃, NO₂, N(R²)C(O)(R²), N(R²)C(O)N(R²)₂, C(O)OR², C(O)N(R²)₂, SO₂N(R²)₂, N(R²)SO₂R² or methylenedioxy;
and R⁹ and R¹⁰ are independently H or $C_{1-8}$alkyl or may be taken together and represent a $C_{5-8}$ ring, optionally substituted by 1–5 halo groups, OR² or S(O)ₘR².

2. A compound in accordance with claim 1 wherein Q is

——(CH₂)ₓ—V—(CH₂)ᵧ——  or

-continued

——(CH₂)ₓ—V—(CH₂)ᵧ—C(R⁷)(R⁷ᵃ)— and x and y are independently 0, 1, 2 or 3.

3. A compound in accordance with claim 1 wherein: V represents a member selected from the group consisting of:

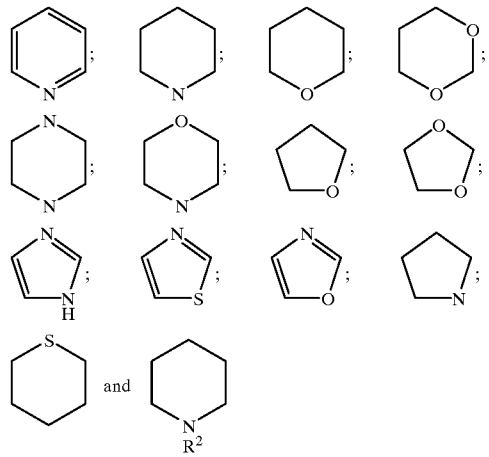

which can be optionally substituted with 1 to 3 halo groups, -OR², -CON(R²)₂, -C(O)OR², $C_1$–$C_4$ alkyl, -S(O)ₘR², N(R²)₂, CF₃ or 1H-tetrazol-5-yl.

4. A compound in accordance with claim 1 wherein R⁸ represents H or -NR⁴R⁵.

5. A compound in accordance with claim 4 wherein R⁸ represents H or -NR⁴R⁵, and R⁴ and R⁵ are independently selected from the group consisting of R², 2,2,2-trifluoroethyl, 3,3,3-trifluoropropyl and (CH₂)ₜ-cyclopropyl and t=0 or 1.

6. A compound in accordance with claim 1 wherein: R¹ is selected from the group consisting of:

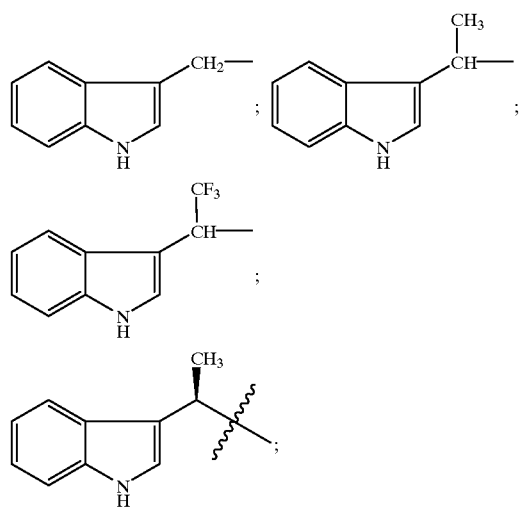

-continued

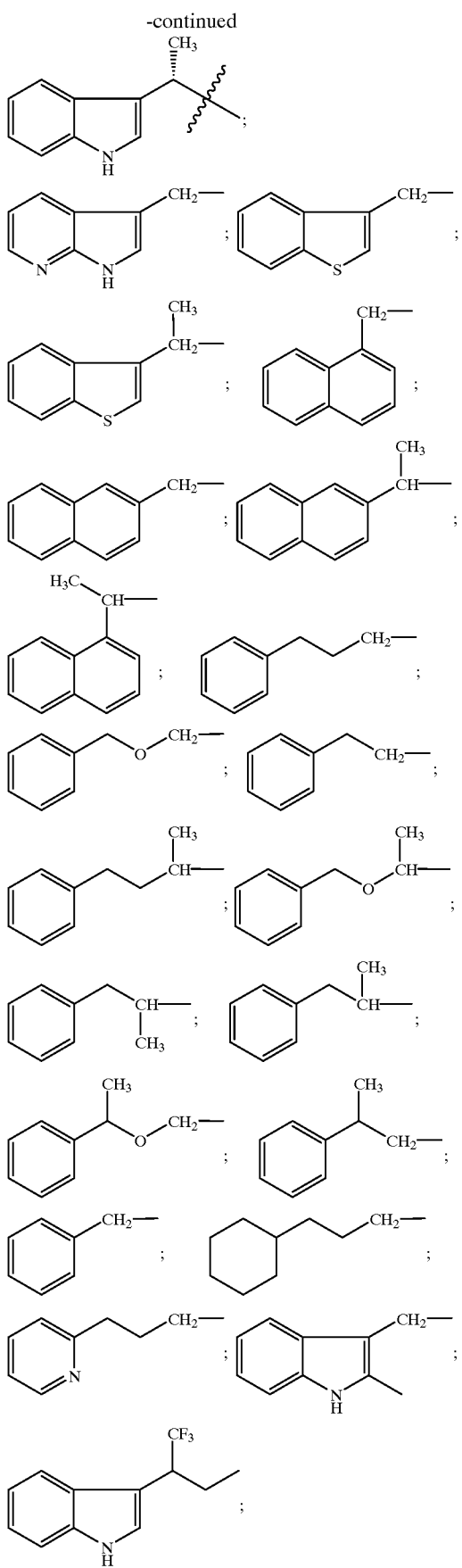

-continued

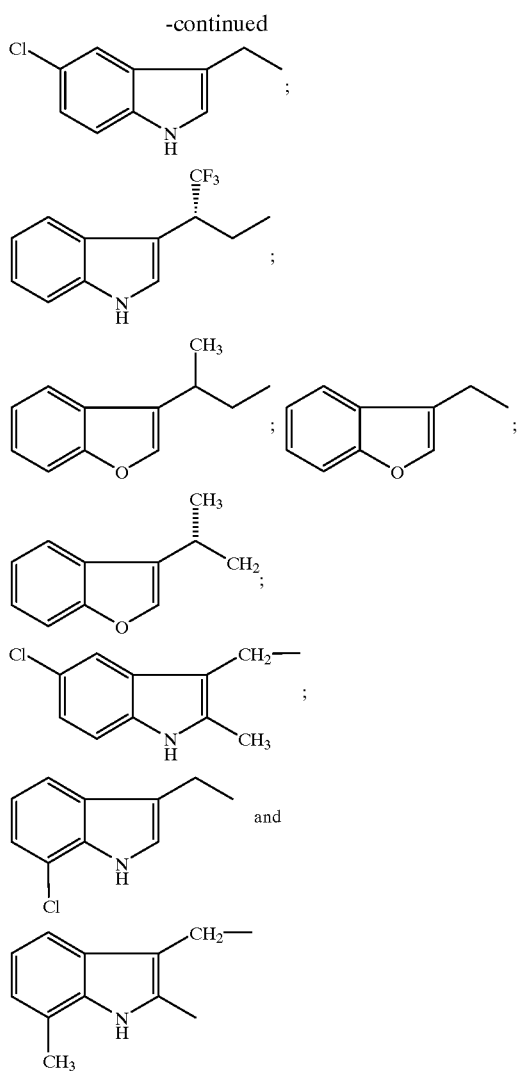

wherein the aryl portion is unsubstituted or substituted with: 1 to 3 of $C_1$–$C_6$ alkyl, 1 to 3 of halogen, 1 to 2 of -$OR^2$, methylenedioxy, -$S(O)_m R^2$, 1 to 2 of -$CF_3$, -$OCF_3$, nitro, -$N(R^2)C(O)(R^2)$, -$C(O)OR^2$, -$C(O)N(R^2)(R^2)$, -1H-tetrazol-5-yl, -$SO_2N(R^2)(R^2)$, -$N(R^2)SO_2$ phenyl, or -$N(R^2)SO_2R^2$.

7. A compound in accordance with claim 1 wherein: $R^2$ is selected from: hydrogen, methyl, ethyl, propyl, isopropyl, butyl, isobutyl and t-butyl.

8. A compound in accordance with claim 1 wherein:

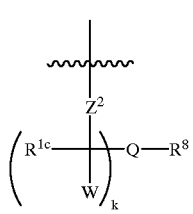

represents
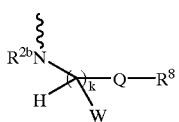
and is selected from the group consisting of:
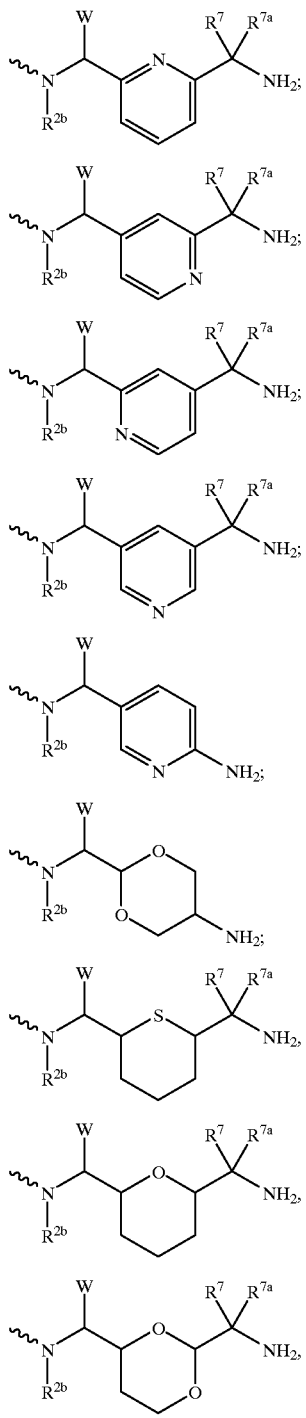
-continued
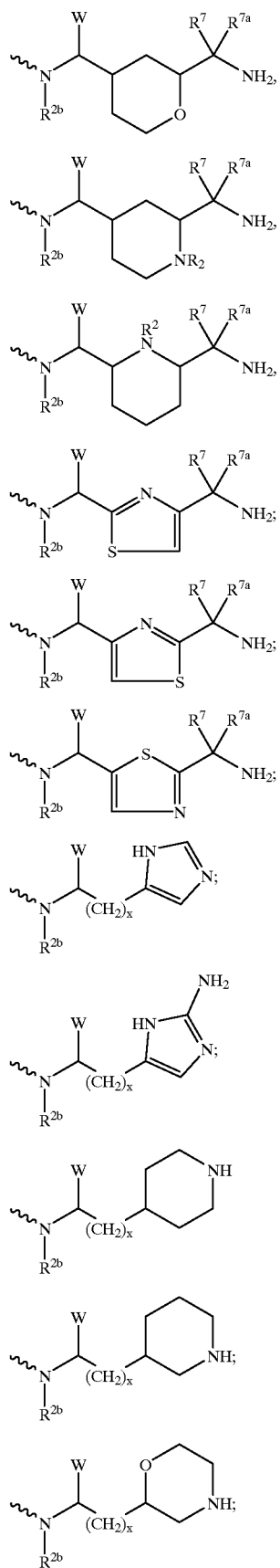

-continued

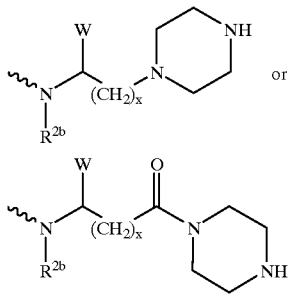

or

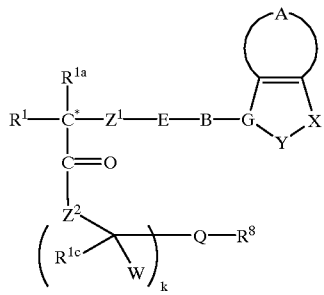

and the heterocyclic rings can be optionally substituted with 1 to 2 R2, 1 to 3 halogen, -OR$^2$, -CON(R$^2$)$_2$, -C(O)OR$^2$, C$_1$–C$_4$ alkyl, -S(O)$_m$R$^2$, N(R$^2$)$_2$, CF$_3$; and x is an integer from 0 to 3.

9. A compound in accordance with claim 1 wherein: W is selected from the group consisting of: hydrogen, C$_1$–C$_4$ alkyl and (CH$_2$)$_q$C(O)OR$^2$.

10. A compound in accordance with claim 1 wherein:
E is selected from the group consisting of -CO-, -C(=N-CN)-, and -SO$_2$-.

11. A compound in accordance with claim 1 wherein:

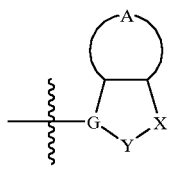

is

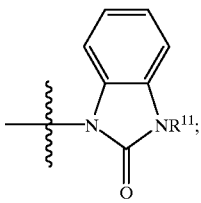

and the aromatic moieties are optionally substituted with 1–3 groups of C$_1$–C$_6$ alkyl, halogen, -OR$^2$, N(R$^2$)$_2$, methylenedioxy, -S(O)$_m$R$^2$, -CF$_3$, -OCF$_3$, nitro, -N(R$^2$)C(O)(R$^2$), -C(O)OR$^2$, -C(O)N(R$^2$)$_2$, -1H-tetrazol-5-yl, -SO$_2$N(R$^2$)$_2$, -N(R$^2$)SO$_2$ phenyl, N(R$^2$)C(O)N(R$^2$) or -N(R$^2$)SO$_2$R$^2$.

12. A compound represented by structural formula I':

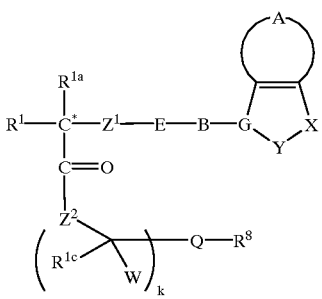

or a pharmaceutically acceptable salt or hydrate thereof, wherein:

R$^1$ is selected from the group consisting of: C$_1$–C$_{10}$ alkyl, aryl, aryl (C$_1$–C$_6$ alkyl), (C$_3$–C$_7$ cycloalkyl)(C$_1$–C$_6$ alkyl)-, (C$_1$–C$_5$ alkyl)-K-(C$_1$–C$_5$ alkyl)-, aryl(C$_0$–C$_5$ alkyl)-K-(C$_1$–C$_5$ alkyl)-, and (C$_3$–C$_7$ cycloalkyl)(C$_0$–C$_5$ alkyl)-K-(C$_1$–C$_5$ alkyl)-, where K is -O-, -S(O)$_m$-, -N(R$^2$)C(O)-, -C(O)N(R$^2$)-, -CR$^2$=CR$^2$-, or -C≡C-, where R$^2$ and alkyl may be further substituted by 1 to 5 halogen, S(O)$_m$R$^{2a}$, 1 to 3 of OR$^{2a}$ or C(O)OR$^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of C$_1$–C$_6$ alkyl, 1 to 3 of halogen, 1 to 2 of -OR$^2$, methylenedioxy, -S(O)$_m$R$^2$, 1 to 2 of -CF$_3$, -OCF$_3$, nitro, -N(R$^2$)C(O)(R$^2$), -C(O)OR$^2$, -C(O)N(R$^2$)(R$^2$), -1H-tetrazol-5-yl, -SO$_2$N(R$^2$)(R$^2$), -N(R$^2$)SO$_2$ phenyl, or -N(R$^2$)SO$_2$R$^2$;

R$^2$ is selected from: hydrogen, C$_1$–C$_8$ alkyl, (CH$_2$)$_t$ aryl, and C$_3$–C$_7$ cycloalkyl, and where two C$_1$–C$_6$ alkyl groups are present on one atom, they optionally are joined to form a C$_3$–C$_8$ cyclic ring, optionally including oxygen, sulfur or NR$^{3a}$, where R$^{3a}$ is hydrogen, or C$_1$–C$_6$ alkyl, optionally substituted by hydroxyl; Aryl is defined in the body of the case;

R$^{1a}$ is selected from the group consisting of hydrogen, and C$_1$–C$_3$ alkyl;

R$^{2a}$ is selected from the group consisting of hydrogen and C$_1$–C$_3$ alkyl, said alkyl optionally substituted by hydroxyl;

R$^{2b}$ is selected from hydrogen, C$_1$–C$_8$ alkyl, (CH$_2$)$_t$ aryl, -(CH$_2$)$_n$CO$_2$R$^2$, -(CH$_2$)$_n$CON(R$^2$)$_2$, -(CH$_2$)$_n$OH or -(CH$_2$)$_n$OR$^2$;

R$^{1c}$ is selected from the group consisting of hydrogen, -(CH$_2$)$_q$SR$^2$, -(CH$_2$)$_q$OR$^2$ and C$_1$–C$_8$ alkyl;

Z$^1$ is selected from the group consisting of -O-, -CH2- and -NR$^{2a}$;

Z$^2$ is selected from the group consisting of -O-, -CH2-,-CHR$^{2b}$- and -NR$^{2b}$, when Z$^2$ is NR$^{2b}$ it can optionally be linked to R$^{1c}$, Q and/or W to form a C5–8 cyclic ring, which can optionally be interrupted by oxygen, S(O)$_m$ or NR$^{2a}$;

W is selected from the group consisting of: hydrogen, C$_1$–C$_8$ alkyl, (CH2)$_t$ aryl, -(CH$_2$)$_q$C(O)OR$^2$, -(CH$_2$)$_q$OR$^2$,-(CH$_2$)$_q$OC(O)R$^2$, -(CH$_2$)$_q$C(O)R$^2$, -(CH$_2$)$_q$C(O)(CH$_2$)$_t$aryl, -(CH$_2$)$_q$C(O)N(R$^2$)$_2$, -(CH$_2$)$_q$N(R$^2$)C(O)R$^2$, -(CH$_2$)$_q$N(R$^2$)SO$_2$R$^2$, -(CH$_2$)$_q$N(R$^2$)C(O)N(R$^2$)$_2$, -(CH$_2$)$_q$OC(O)N(R$^2$)$_2$, -(CH$_2$)$_q$N(R$^2$)C(O)OR$^2$, -(CH$_2$)$_q$N(R$^2$)SO$_2$N(R$^2$)$_2$, -(CH$_2$)$_q$S(O)$_m$R$^2$, and (CH$_2$)$_t$ heteroryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ are optionally substituted with 1 to 2 $C_1$-$C_4$ alkyl, $OR^2$, $C(O)OR^2$, 1–3 halo and said aryl is optionally substituted with 1 to 3 halogen, -$OR^2$, -$CON(R^2)_2$, -$C(O)OR^2$, $C_1$-$C_4$ alkyl, -$S(O)_mR^2$, $N(R^2)_2$, $CF_3$ or 1H-tetrazol-5-yl;

Q is selected from the group consisting of:

$$—(CH_2)_{\overline{x}}—V—(CH_2)_{\overline{y}}—; \quad —(CH_2)_{\overline{x}}—V—\underset{R^{7a}}{\overset{R^7}{C}}—(CH_2)_{\overline{y}}—;$$

$$—(CH_2)_{\overline{x}}—\underset{R^{7a}}{\overset{R^7}{C}}—V—(CH_2)_{\overline{y}}— \quad \text{and}$$

$$—(CH_2)_{\overline{x}}—V—(CH_2)_{\overline{y}}—\underset{R^{7a}}{\overset{R^7}{C}}—$$

where x and y are independently 0, 1, 2, 3, 4, 5, 6;

V is a $C_3$-$C_{10}$ heterocyclic ring which may be a saturated, partially saturated or aromatic cyclic or bicyclic ring, including all regio- and diastereo- isomers, containing 1–4 of N and/or 1–2 of O or S and including the group consisting of furan, thiophene, imidazole, oxazole, thiazole, pyridine, pyrimidine, purine, indole, quinoline, isoquinoline, thiolane, tetrahydrofuran, tetrahydropyran, azetidine, pyrrolidine, piperidine, imidazoline, morpholine, piperazine, pyrazine, tetrahydrothiopyran, 1,3-dioxolane, 1,3-dioxane, said the heterocyclic ring can be optionally substituted with 1 to 3 halogen, -$OR^2$, -$CON(R^2)_2$, -$C(O)OR^2$, $C_1$-$C_4$ alkyl, -$S(O)_mR^2$, $(CH_2)_tN(R^2)_2$, $CF_3$ or 1H-tetrazole-5-yl; and in the case where diastereo- or regio- isomers are present, all are included;

$R^7$ and $R^{7a}$ are independently trifluoromethyl or $R^2$;

R8 is selected from the group consisting of hydrogen $$\underset{R^5}{\overset{R^4}{\sim\!\!\sim\!\!\sim\!N}}, \quad \underset{\underset{R^{10}}{|}}{\overset{NR^9}{\underset{\|}{\sim\!\!\sim\!\!\sim\!N}}}\!\!-\!NR^{10} \quad \text{and} \quad \underset{\underset{R^4}{|}}{\overset{R^4}{\sim\!\!\sim\!\!\sim\!N^+}}\!\!-\!R^4;$$

$R^4$ and $R^5$ are independently selected from the group consisting of $R^2$, -$C(=NR^2)N(R^2)_2$, -$C(=NCN)N(R^2)_2$, -$C(=NC(O)R^2)N(R^2)_2$, $C(=NSO_2R^2)N(R^2)_2$, -$C(=NNO_2)NR^2$, heteroaryl, -$C(=O)N(R^2)_2$, -$C(=S)N(R^2)_2$, -$C(=O)R^2$, 2,2,2-trifluoroethyl, 3,3,3-trifluoropropyl, $(CH_2)_t$ cyclopropyl, or $R^4$ and $R^5$ may be taken together to form -$(CH_2)_d$-$L_a(CH_2)_e$- where $L_a$ is -$C(R^2)_2$-, -O-, -$S(O)_m$- or -$N(R^2)$-, d and e are independently 1 to 3, said heteroaryl and $R^2$ optionally substituted with 1–3 groups of $C_1$-$C_6$ alkyl, 1–7 halo, $N(R^2)_2$, $OR^2$, $N(R^2)C(O)R^2$, $C(O)N(R^2)$, $OC(O)R^2$, $S(O)_mR^2$, $CF_3$, $OCF_3$, $NO_2$, $N(R^2)C(O)R^2$, $N(R^2)C(O)N(R^2)_2$, $C(O)OR^2$, $C(O)N(R^2)_2$, $SO_2N(R^2)_2$, $N(R^2)SO_2R^2$, or methylenedioxy; and the heteroaryl is pyridyl, imidazolyl, pyrimidinyl, thiazolyl or pyrazinyl;

E is selected from the group consisting of -$SO_2$-, -$CO(C(R^2)_2)_n$-, -$C(=N-CN)$-, -$C(=N-NO_2)$ and -$C(=N-SO_2N(R^2)_2)$-; $R^9$ & $R^{10}$ are independently H, $C_{1-8}$ alkyl or may be taken together to form a C5–8 cyclic ring, which can optionally be substituted by 1–5 halogen, $OR^2$ or $S(O)_mR^2$;

B is where attachment points are indicated by lines ($) external to the rings which are optionally substituted by $C_1$-$C_6$ alkyl;

G is N;

Y is -C(O)-;

X is -$N(R^{11})$-;

$R^{11}$ is H, $C_1$-$C_8$ alkyl, $CF_3$, $CH_2CF_3$, -$(CH_2)_pOR^2$, -$(CH_2)_p N(R^2)_2$, $(CH2)_pN(R^2)C(O)N(R^2)_2$, -$(CH_2)_pN(R^2)C(O)R^2$, $(CH_2)_2$ heteroaryl, $(CH_2)_pN(R^2)SO_2C_1$-$C_4$ alkyl, -$(CH_2)_pC(O)N(R^2)_2$, or -$(CH_2)_pC(O)OR^2$ where heteroaryl is tetrazole, oxadiazole, imidazole or triazole which are optionally substituted with $R^2$, $OR^2$, $CF_3$ or $N(R^2)_2$ and where p is 0–3;

A is a fused aryl group, said aryl group containing 6 atoms and being optionally substituted with 1–3 groups of $C_1$-$C_6$ alkyl, halogen, -$OR^2$, $N(R^2)_2$, methylenedioxy, -$S(O)_mR^2$, -$CF_3$, -$OCF_3$, nitro, -$N(R^2)C(O)(R^2)$, -$C(O)OR^2$, -$C(O)N(R^2)_2$, -1H-tetrazol-5-yl, -$SO_2N(R^2)_2$, -$N(R^2)SO_2$ phenyl, $N(R^2)C(O)N(R^2)$ or -$N(R^2)SO_2R^2$, and in the case where regioisomers are present, all are included;

k is an integer from 0 to 1, such that when k is 0, Q is attached directly to $Z^2$;

m is an integer from 0 to 2;

n is an integer from 0 to 3;

q is an integer from 0 to 3; and t is an integer from 0 to 3.

13. A compound according to claim 1 represented by structural formula Ib:

Formula Ib or a pharmaceutically acceptable salt or hydrate thereof, wherein:

$R^1$ is selected from the group consisting of: $C_1$-$C_{10}$ alkyl, aryl, aryl ($C_1$-$C_6$ alkyl), ($C_3$-$C_7$ cycloalkyl)($C_1$-$C_6$ alkyl)-, ($C_1$-$C_5$ alkyl)-K-($C_1$-$C_5$ alkyl), aryl($C_0$-$C_5$ alkyl)-K-($C_1$-$C_5$ alkyl)-, and ($C_3$-$C_7$ cycloalkyl)($C_0$-$C_5$ alkyl)-K-($C_1$-$C_5$ alkyl)-, where K is -O-, -$S(O)_m$-, -$N(R^2)C(O)$-, -$C(O)N(R^2)$-, -$CR^2=CR^2$-, or -$C\equiv C$-, where $R^2$ and alkyl may be further substituted by 1 to 5 halogen, $S(O)_mR^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of -$OR^2$, methylenedioxy, -$S(O)_mR^2$, 1 to 2 of -$CF_3$, -$OCF_3$, nitro, -$N(R^2)C(O)(R^2)$, -$C(O)OR^2$, -$C(O)N(R^2)(R^2)$, -1H-tetrazol-5-yl, -$SO_2N(R^2)(R^2)$, -$N(R^2)SO_2$ phenyl, or -$N(R^2)SO_2R^2$;

$R^2$ is selected from: hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl;

$R^{2a}$ is selected from the group consisting of hydrogen and $C_1$–$C_3$ alkyl, said alkyl optionally substituted by hydroxyl;

$R^{2b}$ is selected from hydrogen, C1–C8 alkyl, $(CH_2)_t$ aryl, -$(CH_2)_nCO_2R^2$, -$(CH_2)_nCON(R^2)_2$, -$(CH_2)_nOH$ or -$(CH_2)_nOR^2$;

$R^{1c}$ is selected from the group consisting of hydrogen, and $C_1$–$C_8$ alkyl;

$Z^2$ is selected from the group consisting of -O-, -CH2-, -$CHR_{2b}$- and -$NR^{2b}$, when $Z^2$ is $NR^{2b}$ it can optionally be linked to $R^{1c}$, Q and/or W to form a $C_{5-8}$ cyclic ring, which can optionally be interrupted by oxygen, $S(O)_m$ or $NR^{2a}$;

W is selected from the group consisting of: hydrogen, $C_1$–$C_8$ alkyl, $(CH_2)_t$ aryl, -$(CH_2)_qC(O)OR^2$, -$(CH_2)_q OR^2$, -$(CH_2)_qOC(O)R^2$, -$(CH_2)_qC(O)R^2$, -$(CH_2)_qC(O)$ $(CH_2)_t$aryl, -$(CH_2)_qC(O)N(R^2)_2$, -$(CH_2)_qN(R^2)C(O)R^2$, -$(CH_2)_qN(R^2)SO_2R^2$, -$(CH_2)_qN(R^2)C(O)N(R^2)_2$, -$(CH_2)_qOC(O)N(R^2)_2$, -$(CH_2)_qN(R^2)C(O)OR^2$, -$(CH_2)_q N(R^2)SO_2N(R^2)_2$, -$(CH_2)_qS(O)_mR^2$, and $(CH_2)_t$ heteroaryl where the heteroaryl is preferably tetrazole, oxadiazole, hiadiazole, triazole or pyrazine, which is optionally substituted with $R^2$, $N(R^2)_2$ and $OR^2$, where $R^2$, $(CH_2)_q$and $(CH2)_t$ are optionally substituted with 1 to 2 $C_1$–$C_4$ alkyl, $OR^2$, $C(O)OR^2$, 1–3 halo and said aryl is optionally substituted with 1 to 3 halogen, -$OR^2$, -$CON(R^2)_2$, -$C(O)OR^2$, $C_1$–$C_4$ alkyl, -$S(O)_mR^2$, -$N(R^2)_2$, $CF_3$ or 1H-tetrazol-5-yl;

Q is

—(CH2)$_{\overline{x}}$—V—(CH2)$_{\overline{y}}$—  or

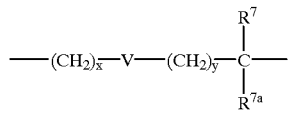

where x and y are independently 0, 1, 2, 3, 4;

V is a $C_{3-10}$ heterocyclic ring which may be a saturated, partially saturated or aromatic cyclic or bicyclic ring, including all regio- and diastereo- isomers, containing 1–4 of N and/or 1–2 of O or S and including the group consisting of furan, thiophene, imidazole, oxazole, thiazole, pyridine, pyrimidine, purine, indole, quinoline, isoquinoline, thiolane, tetrahydrofuran, tetrahydropyran, azetidine, pyrrolidine, piperidine, imidazoline, morpholine, piperazine, pyrazine, tetrahydrothiopyran, 1,3-dioxolane, 1,3-dioxane, said the heterocyclic ring can be optionally substituted with 1 to 3 halogen, -$OR^2$, -$CON(R^2)_2$, -$C(O)OR^2$, $C_1$–$C_4$ alkyl, -$S(O)_mR^2$, $(CH_2)_tN(R^2)_2$, $CF_3$ or 1H-tetrazol-5-yl; and in the case where diastereo- or regio- isomers are present, all are included;

$R^7$ and $R^{7a}$ are independently trifluoromethyl or $R^2$;

R8 is selected from the group consisting of hydrogen

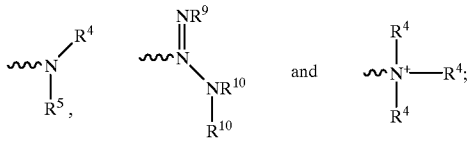

$R^4$ and $R^5$ are independently selected from the group consisting of $R^2$, -$C(=NR^2)N(R^2)_2$, -$C(=NCN)N(R^2)_2$, -$C(=NC(O)R^2)N(R^2)_2$, $C(=NSO_2R^2)N(R^2)_2$, -$C(=S)N(R^2)_2$, -$C(=NNO_2)NR^2$, heteroaryl, -$C(=O)N(R^2)_2$, -$C(=O)R^2$, 2,2,2-trifluoroethyl, 3,3,3-trifluoropropyl, $(CH_2)_t$ cyclopropyl, or $R^4$ and $R^5$ may be taken together to form -$(CH_2)_d$-$L_a$-$(CH_2)_e$- where $L_a$ is -$C(R^2)_2$-, -O-, -$S(O)_m$- or -$N(R^2)$-, d and e are independently 1 to 3, said heteroaryl and $R^2$ optionally substituted with 1–3 groups of $C_{1-6}$ alkyl, 1–7 halo, $N(R^2)_2$, $OR^2$, $N(R^2)C(O)R^2$, $C(O)N(R^2)$, $OC(O)R^2$, $S(O)_mR^2$, $CF_3$, $OCF_3$, $NO_2$, $N(R^2)C(O)(R^2)$, $N(R^2)C(O)N(R^2)_2$, $C(O)OR^2$, $C(O)N(R^2)_2$, $SO_2N(R^2)_2$, $N(R^2)SO_2R^2$, or methylenedioxy; and the heteroaryl is pyridyl, imidazolyl, pyrimidinyl, thiazolyl or pyrazinyl;

E is selected from the group consisting of -$SO_2$-, -$CO(C(R^2)_2)_n$-, -$C(=N-CN)$-, -$C(=N-NO_2)$- and -$C(=N-SO_2N(R^2)_2)$-;

$R^9$ and $R^{10}$ are independently H, $C_{1-8}$ alkyl or may be taken together to form a C5–8 cyclic ring, which can optionally be substituted by 1–5 halogen, $OR^2$ or $S(O)_mR^2$;

B is

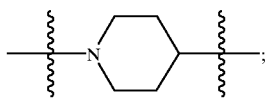

where attachment points are indicated by lines (§) external to the rings which are optionally substituted by $C_1$–$C_6$ alkyl;

G is N;

Y is -C(O)-;

X is -$N(R^{11})$-;

$R^{11}$ is H, $C_1$–$C_8$ alkyl, $CF_3$, $CH_2CF_3$, -$(CH_2)_pOR^2$, -$(CH_2)_p N(R^2)_2$, $(CH2)_pN(R^2)C(O)N(R^2)_2$, -$(CH_2)_pN(R^2)C(O)R^2$, $(CH_2)_2$ heteroaryl, $(CH_2)_pN(R^2)SO_2C_1$–$C_4$ alkyl, -$(CH_2)_pC(O)N(R^2)_2$, or -$(CH_2)_pC(O)OR^2$ where heteroaryl is tetrazole, oxadiazole, imidazole or triazole which are optionally substituted with $R^2$, $OR^2$, $CF_3$ or $N(R^2)_2$ and where p is 0–3;

A is a fused aryl group, said aryl group containing 6 atoms and being optionally substituted with 1–3 groups of $C_1$–$C_6$ alkyl, halogen, -$OR^2$, $N(R^2)_2$, methylenedioxy, -$S(O)_mR^2$, -$CF_3$, -$OCF_3$, nitro, -$N(R^2)C(O)(R^2)$, -$C(O)OR^2$, -$C(O)N(R^2)_2$, -1H-tetrazol-5-yl, -$SO_2N(R^2)_2$, -$N(R^2)SO_2$ phenyl, $N(R^2)C(O)N(R^2)$ or -$N(R^2)SO_2R^2$, and in the case where regioisomers are present, all are included;

k is an integer from 0 to 1, such that when k is 0, Q is attached directly to $Z^2$;

m is an integer from 0 to 2;

n is an integer from 0 to 3;

q is an integer from 0 to 3; and t is an integer from 0 to 3.

14. A compound according to claim 1 represented by structural formula Ic:

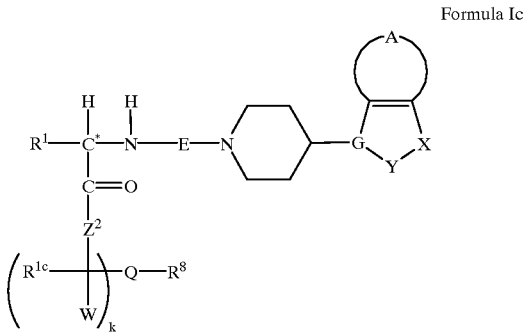

Formula Ic or a pharmaceutically acceptable salt or hydrate thereof, wherein:

$R^1$ is selected from the group consisting of: $C_1$–$C_{10}$ alkyl, aryl, aryl ($C_1$–$C_6$ alkyl), ($C_3$–$C_7$ cycloalkyl)($C_1$–$C_6$ alkyl)-, ($C_1$–$C_5$ alkyl)-O-($C_1$–$C_5$ alkyl), and aryl ($C_0$–$C_5$ alkyl)-O-($C_1$–$C_5$ alkyl)-, where $R^2$ and alkyl may be further substituted by 1 to 5 halogen, $S(O)_m R^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substituent selected from: 1 to 3 of $C_1$–$C_6$ alkyl, 1 to 3 of halogen, 1 to 2 of -$OR^2$, methylenedioxy, -$S(O)_m R^2$, 1 to 2 of -$CF_3$, -$OCF_3$, nitro, -$N(R^2)C(O)(R^2)$, -$C(O)OR^2$, -$C(O)N(R^2)(R^2)$, -1H-tetrazol-5-yl, -$SO_2N(R^2)(R^2)$, -$N(R^2)SO_2$ phenyl, or -$N(R^2)SO_2R^2$;

$R^2$ is selected from: hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl;

$R^{2a}$ is selected from the group consisting of hydrogen and $C_1$–$C_3$ alkyl, said alkyl optionally substituted by hydroxyl;

$Z^2$ is selected from the group consisting of -O-, -CH2-,-CHR$^{2b}$- and -NR$^{2b}$, when $Z^2$ is NR$^{2b}$ it can optionally be linked to $R^{1c}$, Q and/or W to form a C5–8 cyclic ring;

$R^{2b}$ is selected from hydrogen, C1–C8 alkyl, $(CH_2)_t$ aryl, -$(CH_2)_n CO_2 R^2$, -$(CH_2)_n CON(R^2)_2$, -$(CH_2)_n OH$ or -$(CH_2)_n OR^2$;

$R^{1c}$ is selected from the group consisting of hydrogen and $C_1$–$C_8$ alkyl;

W is selected from the group consisting of: hydrogen, $C_1$–$C_8$ alkyl, (CH2)$_t$ aryl, -$(CH_2)_q C(O)OR^2$, -$(CH_2)_q OR^2$, -$(CH_2)_q OC(O)R^2$, -$(CH_2)_q C(O)R^2$, -$(CH_2)_q C(O)(CH_2)_t$ aryl, -$(CH_2)_q C(O)N(R^2)_2$, -$(CH_2)_q N(R^2)C(O)R^2$, -$(CH_2)_q N(R^2)SO_2 R^2$, -$(CH_2)_q N(R^2)C(O)N(R^2)_2$, -$(CH_2)_q OC(O)N(R^2)_2$, -$(CH_2)_q N(R^2)C(O)OR^2$, -$(CH_2)_q N(R^2)SO_2 N(R^2)_2$, -$(CH_2)_q S(O)_m R^2$, and $(CH_2)_t$ heteroaryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ are ptionally substituted with 1 to 2 $C_1$–$C_4$ alkyl, $OR^2$, $C(O)OR^2$, 1–3 halo and said aryl is optionally substituted with 1 to 3 halogen, -$OR^2$, -$CON(R^2)_2$, -$C(O)OR^2$, $C_1$–$C_4$ alkyl, -$S(O)_m R^2$, $N(R^2)_2$, $CF_3$ or 1H-tetrazol-5-yl;

Q is

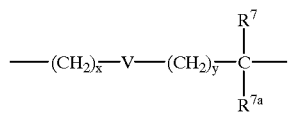

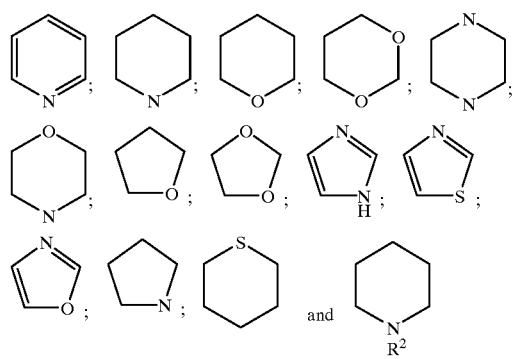

where x and y are independently 0, 1, 2, 3;

V is wherein V can be optionally substituted with 1 to 3 halogen, -$OR^2$, -$CON(R^2)_2$, -$C(O)OR^2$, $C_1$–$C_4$ alkyl, -$S(O)_m R^2$, $N(R^2)_2$, $CF_3$ or 1H-tetrazol-5-yl, and in the case where diastereo- or regio- isomers are present, all are included;

$R^7$ and $R^{7a}$ are independently trifluoromethyl or $R^2$;

$R^8$ is selected from the group consisting of:

-NR$^4$R$^5$,

-C(=NR$^9$)N(R$^{10}$)$_2$ and

-N$^+$(R$^4$)$_3$;

$R^4$ and $R^5$ are independently selected from the group consisting of: $R^2$, -C(=NR$^2$)N(R$^2$)$_2$, -C(=NCN)N(R$^2$)$_2$, -C(=NC(O)R$^2$)N(R$^2$)$_2$, C(=NSO$_2$R$^2$)N(R$^2$)$_2$, -C(=NNO$_2$)NR$^2$, heteroaryl, 2,2,2-trifluoroethyl and 3,3,3-trifluoropropyl or $R^4$ and $R^5$ are taken together and represent

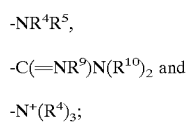

wherein $L_a$ is -C(R$^2$)$_2$-, -O-, -S(O)$_m$- or -N(R$^2$)-, and d and e are independently 1 to 3, and the heteroaryl is pyridyl or imidazolyl;

E is selected from the group consisting of -SO$_2$-, -CO-, -C(=N-CN)-, -C(=N-NO$_2$)- and -C(=N-SO$_2$NH$_2$)-;

$R^9$ & $R^{10}$ are independently H or $C_1$–$C_8$ alkyl;

G is N;

Y is -C(O)-;

X is -N(R$^{11}$)-;

$R^{11}$ is H, $C_1$–$C_8$ alkyl, $CF_3$, $CH_2CF_3$, -$(CH_2)_p OR^2$, -$(CH_2)_p$ N(R$^2$)$_2$, (CH2)$_p$N(R$^2$)C(O)N(R$^2$)$_2$, -$(CH_2)_p$N(R$^2$)C(O)R$^2$, (CH$_2$)$_2$ heteroaryl, (CH$_2$)$_p$N(R$^2$)SO$_2$C$_1$–C$_4$ alkyl, -$(CH_2)_p C(O)N(R^2)_2$, or -$(CH_2)_p C(O)OR^2$ where heteroaryl is tetrazole, oxadiazole, imidazole or triazole which are optionally substituted with $R^2$, $OR^2$, $CF_3$ or $N(R^2)_2$ and where p is 0–3;

A is a fused aryl group, said aryl group containing 6 atoms and being optionally substituted with 1–3 groups of $C_1$–$C_6$ alkyl, halogen, -$OR^2$, $N(R^2)_2$, methylenedioxy, -$S(O)_mR^2$, -$CF_3$, -$OCF_3$, nitro, -$N(R^2)C(O)(R^2)$, -$C(O)OR^2$, -$C(O)N(R^2)_2$, -1H-tetrazol-5-yl, -$SO_2N(R^2)_2$, -$N(R^2)SO_2$ phenyl, $N(R^2)C(O)N(R^2)$ or -$N(R^2)SO_2R^2$, and in the case where regioisomers are present, all are included;

k is an integer from 0 to 1, such that when k is 0, Q is attached directly to $Z^2$;

m is an integer from 0 to 2;

n is an integer from 0 to 3;

q is an integer from 0 to 3; and t is an integer from 0 to 3.

15. A compound according to claim 1 represented by structural formula Id:

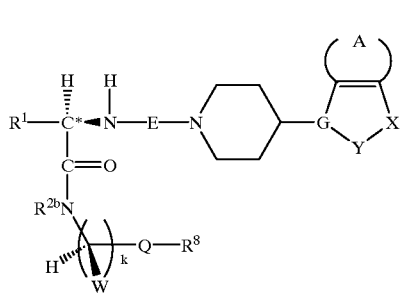

Formula Id or a pharmaceutically acceptable salt or hydrate thereof, wherein:

$R^1$ is selected from the group consisting of:

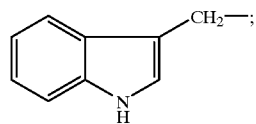

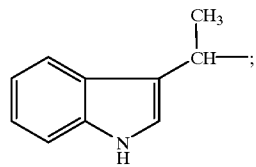

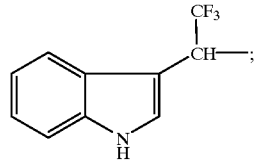

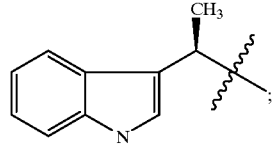

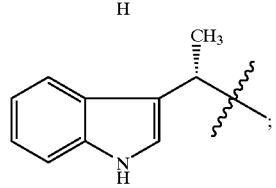

-continued

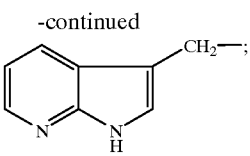

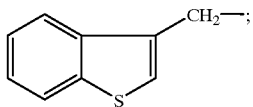

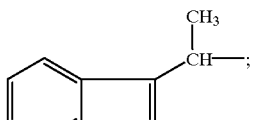

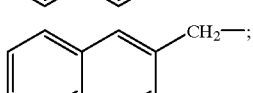

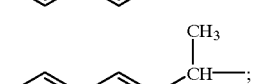

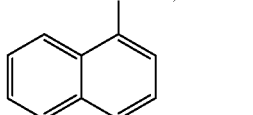

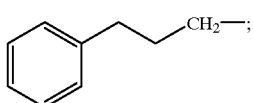

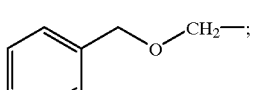

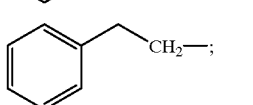

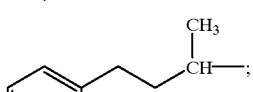

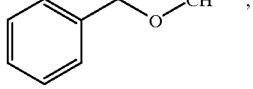

-continued

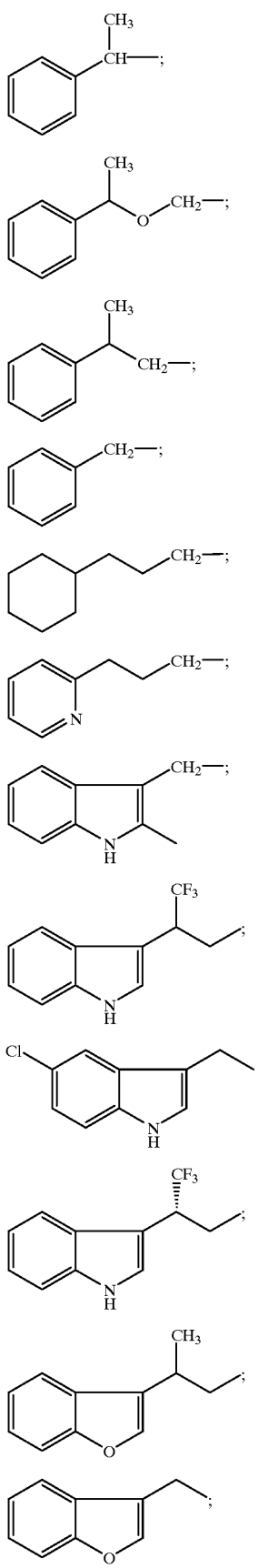

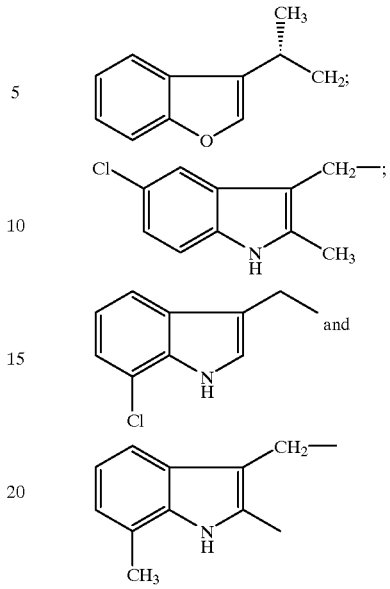

where the aryl is unsubstituted or substituted with a substitutent selected from: 1 to 3 of $C_1$–$C_6$ alkyl, 1 to 3 of halogen, 1 to 2 of -$OR^2$, methylenedioxy, -$S(O)_mR^2$, 1 to 2 of -$CF_3$, -$OCF_3$, nitro, -$N(R^2)C(O)(R^2)$, -$C(O)OR^2$, -$C(O)N(R^2)(R^2)$, -1H-tetrazol-5-yl, -$SO_2N(R^2)(R^2)$, -$N(R^2)SO_2$ phenyl, or -$N(R^2)SO_2R^2$;

$R^2$ is selected from: hydrogen, methyl, ethyl, propyl, isopropyl, butyl, isobutyl and t-butyl;

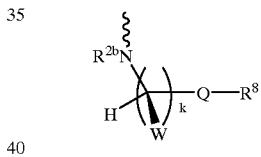

is a member selected from the group consisting of:

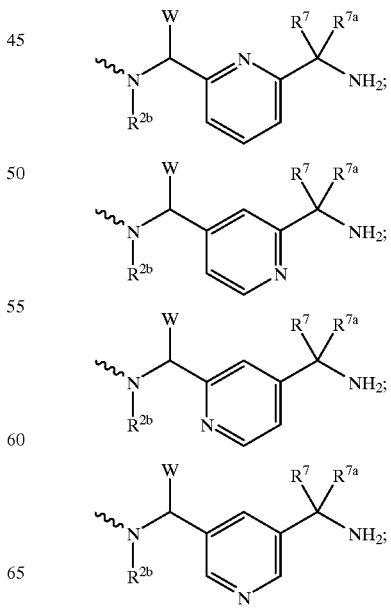

-continued

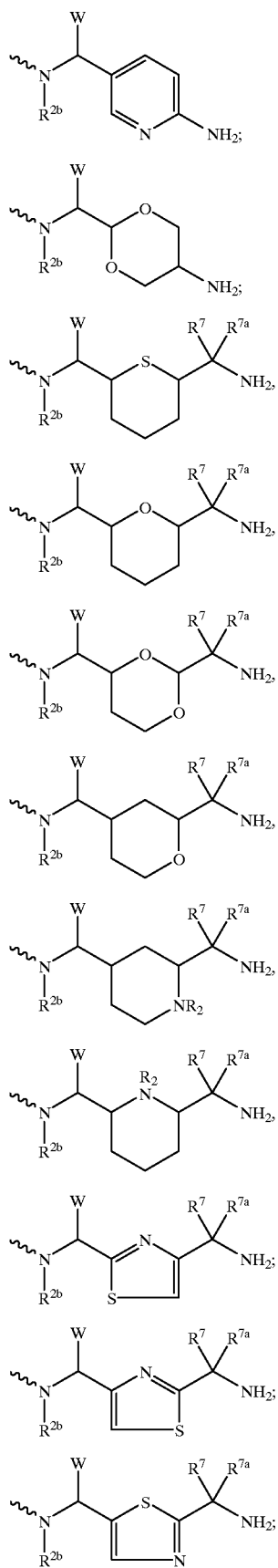

-continued

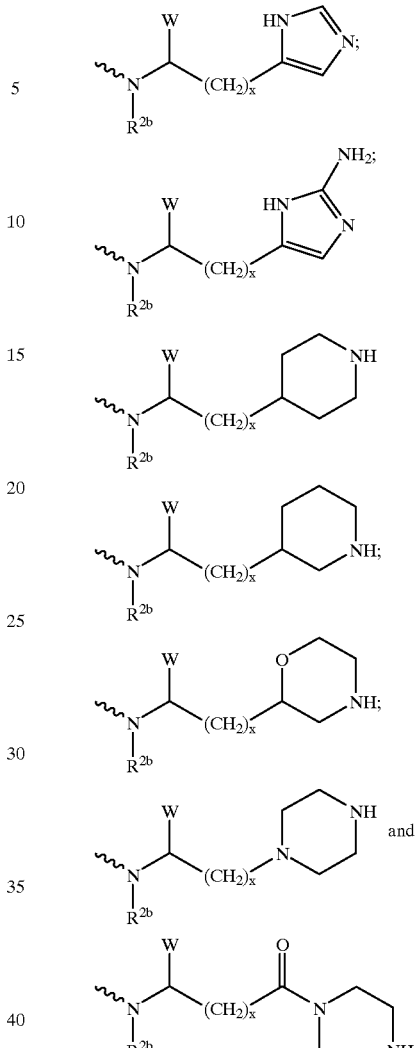

and the aromatic moiety can be optionally substituted with 1 to 2 R2, 1 to 3 halogen, -OR$^2$, -CON(R$^2$)$_2$, -C(O)OR$^2$, C$_1$–C$_4$ alkyl, -S(O)$_m$R$^2$, N(R$^2$)$_2$, CF$_3$; and in the case where diastereo- or regio- isomers are present, all are included; and x is an integer from 0 to 3;

W is selected from the group consisting of: hydrogen, C$_1$–C$_4$ alkyl, (CH$_2$)$_q$C(O)OR$^2$;

R$^7$ and R$^{7a}$ are independently trifluoromethyl or R$^2$;

R$^{2b}$ is selected from hydrogen C$_1$–C$_4$ alkyl;

E is selected from the group consisting of -CO-, -C(=N-CN)-, and -SO$_2$-;

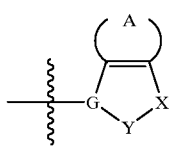

is:

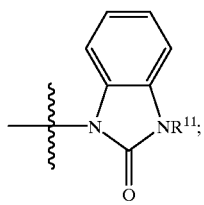

where the aromatic can be optionally substituted with 1–3 groups of $C_1$–$C_6$ alkyl, halogen, -$OR^2$, $N(R^2)_2$, methylenedioxy, -$S(O)_mR^2$, -$CF_3$, -$OCF_3$, nitro, -$N(R^2)C(O)$ ($R^2$), -$C(O)OR^2$, -$C(O)N(R^2)_2$, -1H-tetrazol-5-yl, -$SO_2N(R^2)_2$, -$N(R^2)SO_2$ phenyl, $N(R^2)C(O)N(R^2)$ or -$N(R^2)SO_2R^2$;

$R^{11}$ is H, $C_1$–$C_8$ alkyl, $CF_3$, $CH_2CF_3$, -$(CH_2)_pOR^2$, -$(CH_2)_p N(R^2)_2$, $(CH2)_pN(R^2)C(O)N(R^2)_2$, -$(CH_2)_pN(R^2)C(O)R^2$, $(CH_2)_p$ heteroaryl, $(CH_2)_pN(R^2)SO_2C_1$–$C_4$ alkyl, -$(CH_2)_pC(O)N(R^2)_2$, or -$(CH_2)_pC(O)OR^2$ where heteroaryl is tetrazole, oxadiazole, imidazole or triazole which are optionally substituted with $R^2$, $OR^2$, CF3 or $N(R^2)_2$ and where p is 0–3;

k is an integer 0 or 1, such that when k is 0, Q is directly attached to $NR^{2b}$;

m is an integer from 0 to 2;

n is an integer from 0 to 3; and q is an integer from 0 to 3.

16. A compound according to claim 1 or a pharmaceutically acceptable salt or hydrate thereof, which is selected from the following table:

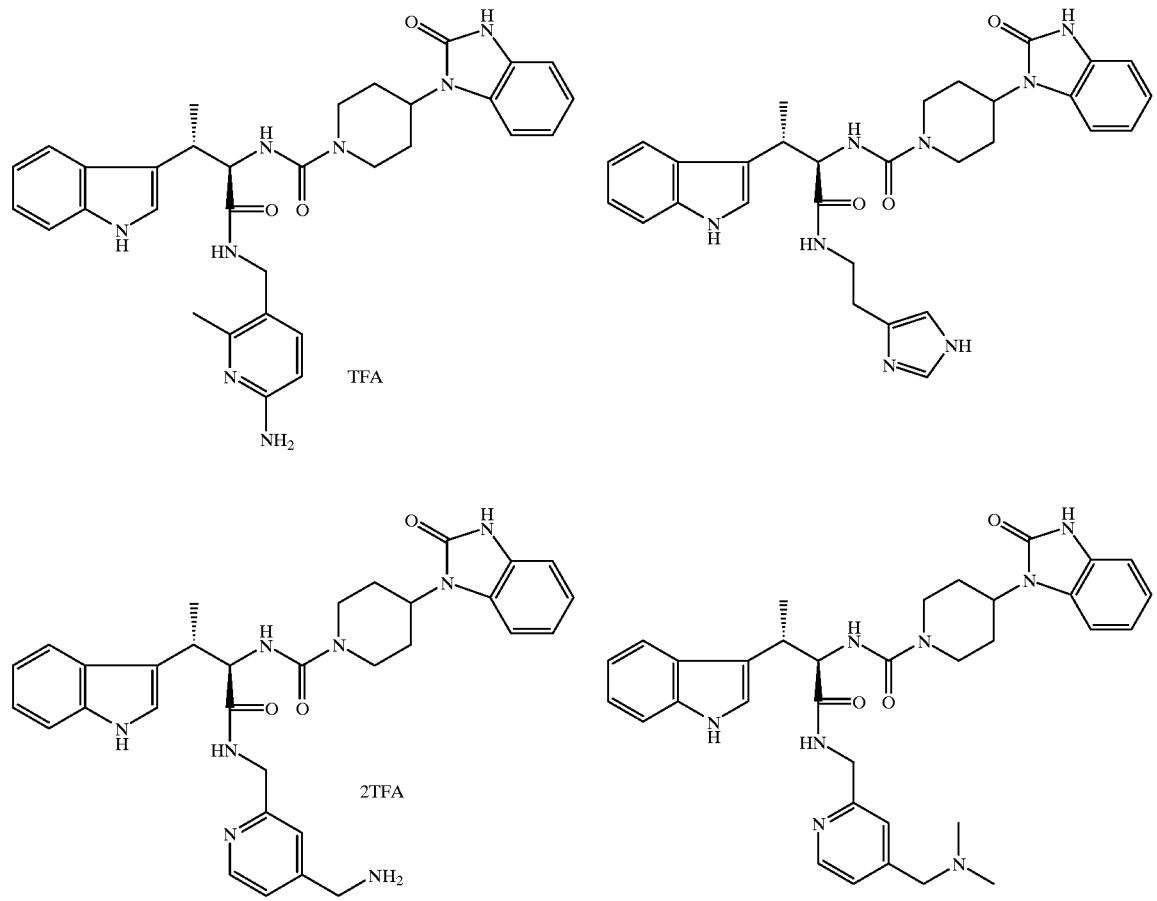

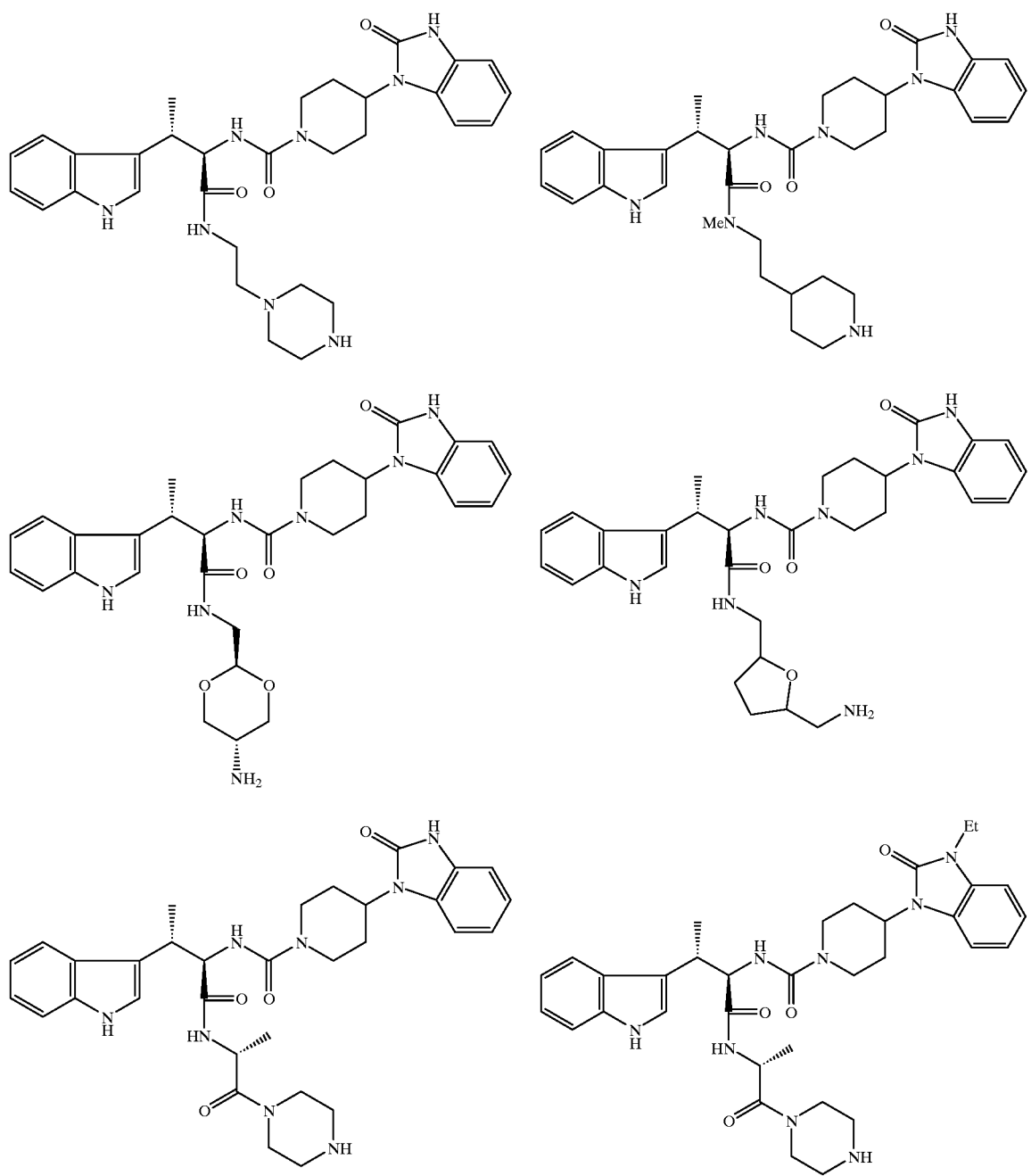

17. A method of treating diabetes disease in a mammal in need of such treatment, which comprises administering to said mammal an effective amount of a somatostatin agonist of claim 1.

18. A method of treating diabetes disease in a mammal in need of such treatment, which comprises administering to said mammal an effective amount of an orally active somatostatin agonist of claim 1.

19. A pharmaceutical composition comprising a therapeutically effective amount of a compound according to claim 1 and a pharmaceutically acceptable carrier.

* * * * *